US011739382B2

(12) United States Patent
Fong et al.

(10) Patent No.: US 11,739,382 B2
(45) Date of Patent: Aug. 29, 2023

(54) COMPOSITIONS AND METHODS FOR AMPLIFICATION AND DETECTION OF HEPATITIS B VIRUS RNA, INCLUDING HBV RNA TRANSCRIBED FROM CCCDNA

(71) Applicant: Roche Molecular Systems, Inc., Pleasanton, CA (US)

(72) Inventors: Jeffery Fong, Lafayette, CA (US); Aaron T. Hamilton, Mountain House, CA (US); Marintha Heil, Danville, CA (US); Igor Kozlov, Danville, CA (US); Ed Gustavo Marins, Brentwood, CA (US); Elizabeth Marie Scott, San Ramon, CA (US); Ling Wang, Dublin, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 636 days.

(21) Appl. No.: 16/798,911

(22) Filed: Feb. 24, 2020

(65) Prior Publication Data
US 2021/0062259 A1    Mar. 4, 2021

Related U.S. Application Data

(60) Provisional application No. 62/892,132, filed on Aug. 27, 2019.

(51) Int. Cl.
*C12Q 1/6876* (2018.01)
*C07H 21/00* (2006.01)
*G01N 33/49* (2006.01)

(52) U.S. Cl.
CPC .......... *C12Q 1/6876* (2013.01); *G01N 33/49* (2013.01); *C12Q 2525/161* (2013.01); *C12Q 2545/114* (2013.01); *C12Q 2600/112* (2013.01)

(58) Field of Classification Search
CPC ................................ C12Q 1/68; C07H 21/00
See application file for complete search history.

(56) References Cited

U.S. PATENT DOCUMENTS

| | | | |
|---|---|---|---|
| 2004/0058314 A1 | 3/2004 | He | |
| 2007/0264646 A1 | 11/2007 | Maki et al. | |
| 2012/0045747 A1 | 2/2012 | Cheung | |
| 2012/0190008 A1* | 7/2012 | Eickhoff | C12Q 1/686 435/6.12 |
| 2015/0275317 A1 | 10/2015 | Sung | |
| 2015/0322502 A1 | 11/2015 | Bodepudi et al. | |
| 2017/0022547 A1* | 1/2017 | Chan | C12Q 1/6816 |
| 2020/0385792 A1* | 12/2020 | Bohannon | B01L 7/525 |

FOREIGN PATENT DOCUMENTS

| | | |
|---|---|---|
| CN | 104388598 B | 8/2016 |
| DE | 4333805 C2 | 3/1995 |
| EP | 1783211 A1 | 9/2007 |
| JP | 3451667 B2 | 3/1995 |
| WO | 2015/049278 A1 | 4/2015 |
| WO | 2021/037399 A1 | 3/2021 |

OTHER PUBLICATIONS

Gibbs et al., Detection of single DNA base differences by competitive oligonucleotide priming. Nucleic Acids Research 17(7):2437. (Year: 1989).*
Jackson et al., The cost-effectiveness of NAT for HIV, HCV, and HBV in whole-blood donations. Transfusion 43:721 (Year: 2003).*
Jose et al., Stability of HCV, HIV-1 and HBV nucleic acids in plasma samples under long-term storage. Biologicals 33:9-16 (Year: 2005).*
Liu et al., J. of Clinical Virology 36(Suppl.1):S33-S44 (Year: 2006).*
Orou et al., Human Mutation 6:163 (Year: 1995).*
Perkin Elmer Cetus GeneAmp DNA amplification Reagent Kit (Year: 1988).*
Zentilin et al., Nature Protocols 2(9) : 2092 (Year: 2007).*
Gao, et al., "A novel one-step quantitative reverse transcription PCR assay for selective amplification of hepatitis B virus pregenomic RNA from a mixture of HBV DNA and RNA in serum," Archives of Virology 164:2683-2690 (2019).
Yeh, et al., "Quantification of hepatitis B virus covalently closed circular DNA by a peptide nucleic acid-clamping PCR method," Journal of Hepatology 68:S489 Abstract FRI-287 (2018).
Butler, et al., "Hepatitis B Virus Serum DNA and RNA Levels in Nucleos(t)ide Analog-Treated or Untreated Patients During Chronic and Acute Infection," Hepatology 68(6):2106-2117 (2018).
Giersch, et al., "Serum HBV pgRNA as a clinical marker for cccDNA activity," Journal of Hepatology 66:460-462 (2017).
Luckenbaugh, et al., "Genome-free hepatitis B virion levels in patient sera as a potential marker to monitor response to antiviral therapy," Journal of Viral Hepatitis 22:561-570 (2014).
Rokuhara, et al., "Hepatitis B virus RNA is measurable in serum and can be a new marker for monitoring lamivudine therapy," Journal of Gastroenterology 41:785-790 (2006).
Sommer, et al., "Genotype-Specific Synthesis and Secretion of Spliced Hepatitis B Virus Genomes in Hepatoma Cells," Virology 271:371-381 (2000).

(Continued)

*Primary Examiner* — Ethan C Whisenant
(74) *Attorney, Agent, or Firm* — Daniel E. Agnew; Eric Grant Lee

(57) ABSTRACT

Methods for the rapid detection of the presence or absence of Hepatitis B Virus (HBV) in a biological or non-biological sample are described. The methods can include performing an amplifying step, a hybridizing step, and a detecting step. Furthermore, primers, competitive blocking oligonucleotides, and probes targeting HBV (in particular HBV RNA, in particular, HBV RNA transcribed from cccDNA, such as pgRNA) and kits are provided that are designed for the detection of HBV (in particular HBV RNA, in particular, HBV RNA transcribed from cccDNA, such as pgRNA).

78 Claims, 9 Drawing Sheets
(6 of 9 Drawing Sheet(s) Filed in Color)
Specification includes a Sequence Listing.

(56) References Cited

OTHER PUBLICATIONS

Wang, et al., "Serum hepatitis B virus RNA is encapsidated pregnome RNA that may be associated with persistence of viral infection and rebound," Journal of Hepatology 65:700-710 (2016).

Wang, et al., "Reply to: "Serum HBV pgRNA as a clinical marker for cccDNA activity" Consistent loss of serum HBV RNA might predict the "para-functional cure" of chronic hepatitis B," Journal of Hepatology 66:454-467 (2017).

Zhang, et al., "Detection of HBV RNA in Serum of Patients," Methods in Molecular Medicine 95:29-40 (2004).

Bayliss, et al., "Hepatitis B virus splicing is enhanced prior to development of hepatocellular carcinoma," Journal of Hepatology 59:1022-1028 (2013).

Kairat, et al., "Truncated Hepatitis B Virus RNA in Human Hepatocellular Carcinoma: Its Representation in Patients with Advancing Age," Intervirology 42:228-237 (1999).

Preiss, et al., "Defective Hepatitis B Virus DNA Is Not Associated with Disease Status But Is Reduced by Polymerase Mutations Associated with Drug Resistance," Hepatology 48(3):741-749 (2008).

Schutz, et al., "Anchored oligo(dT) primed RT/PCR: identification and quantification of related transcripts with distinct 3'-ends," Journal of Virological Methods 86:167-171 (2000).

Van Bommel, et al., "Serum Hepatitis B Virus RNA Levels as an Early Predictor of Hepatitis B Envelope Antigen Seroconversion During Treatment With Polymerase Inhibitors," Hepatology 61(1):66-76 (2015).

International Searching Authority, International Search Report for International Patent Application No. PCT/EP2020/054715 (dated Mar. 4, 2021).

International Searching Authority, Written Opinion of the International Searching Authority for International Patent Application No. PCT/EP2020/054715 (dated Mar. 4, 2021).

International Searching Authority, International Preliminary Report on Patentability for International Patent Application No. PCT/EP2020/054715 (dated Mar. 1, 2022).

Ming Gao, et al., "A novel one-step quantitative reverse transcription PCR assay for selective amplification of hepatitis B virus pregeonomic RNA from a mixture of HBV DNA and RNA in serum," Archives of Virology 164:2683-2690 (2019).

Florian Von Bommel, et al., "Serum Hepatitis B Virus RNA Levels as an Early Predictor of Hepatitis B Envelope Antigen Seroconversion During Treatment With Polymerase Inhibitors," Hepatology 61(1):66-76 (2015).

C.-T. Yeh, et al., "Quantification of hepatitis B virus covalently closed circular DNA by a peptide nucleic acid-clamping PCR method," Journal of Hepatology 68:S489, FRI-287 (2018).

International Searching Authority, Notification of Transmittal of the International Search Report and the Written Opinion of the International Searching Authority, or the Declaration, for International Patent Application No. PCT/EP2020/054715 (dated Apr. 29, 2020).

International Searching Authority, Written Opinion of the International Searching Authority, for International Patent Application No. PCT/EP2020/054715 (dated Apr. 29, 2020).

* cited by examiner

*HBV DNA at polyadenylation site*  
GGGGCATGGACATTGACCCGTATAAAGAATTTGGAGCTTCTGTGGAGTTACTCTCTTTTTGCCTTCTGACTTCTTTCCTTCTATTCGAGATCTCC  SEQ ID NO: 401

(non extensible C3 spacer)- ▯▮▮▯  Competitive blocking oligo designs for HBV DNA binding
Binds to HBV DNA overlapping part of all of the
HBV-binding section of the primer (example—
oligos can vary in length and position)

*HBV pgRNA at polyadenylation site*   SEQ ID NO: 402
GGGGCAUGGACAUUGACCCGUAUAAAGAAUUUGGAGCUUCAAAAAAAAAAAAAAAAAAAAAAAAAA ▮▮TTTTTTTTTTTTTTTT▮▮  RT primer (reverse primer)
SEQ ID NO: 403

FIG. 2

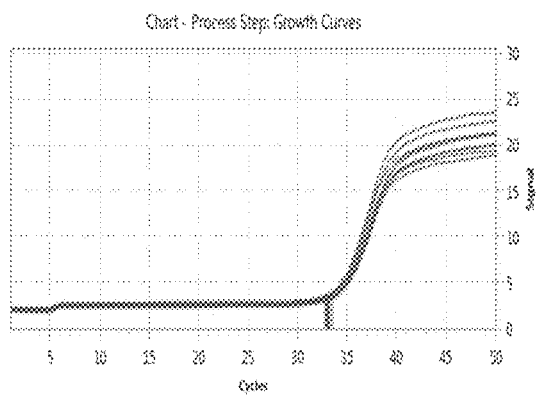
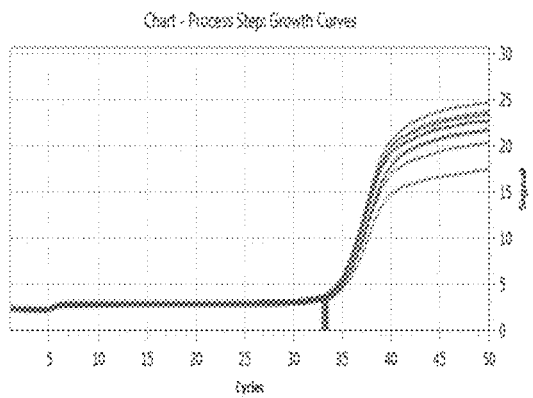
RNA (100 copies/mL)
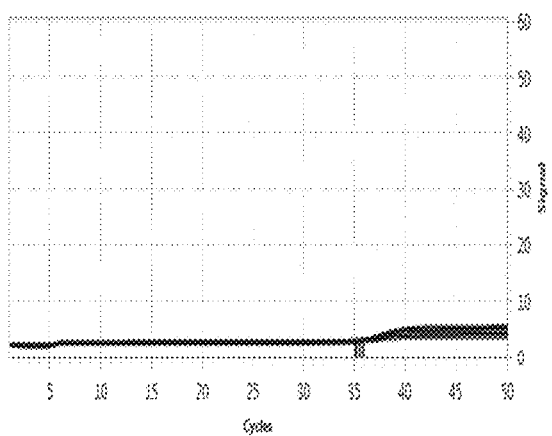
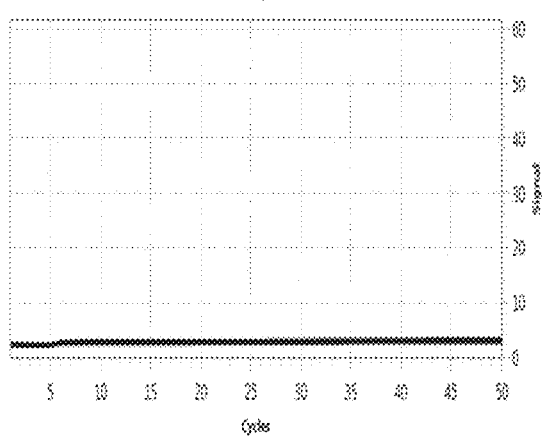
DNA (100,000 IU/mL)
FIG. 7

HBV RNA with and without DNA at 1E7 IU/mL
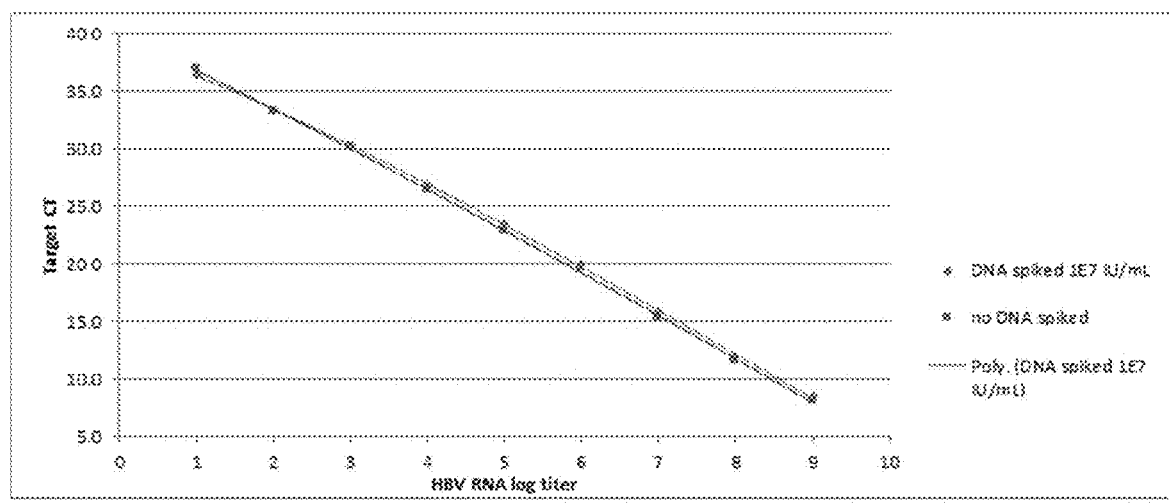
HBV RNA with and without DNA at 1E9 IU/mL
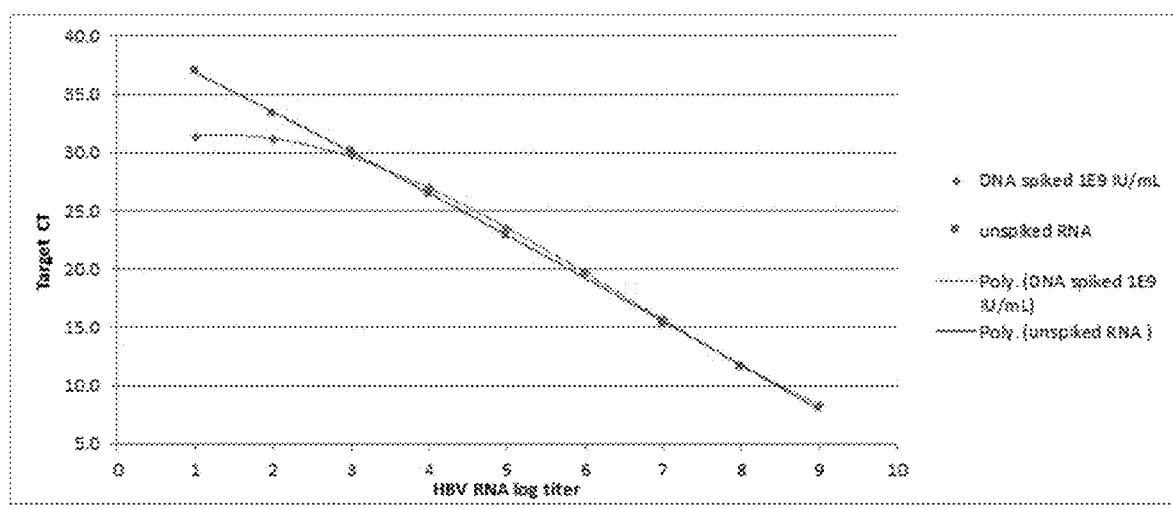
FIG. 9

SEQUENCE LISTING

<160> NUMBER OF SEQ ID NOS: 403

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aactccacag aagctccaaa ttc                                              23

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agagtaactc cacagaagct ccaaattc                                         28

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gagagtaact ccacagaagc tc                                               22

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gagagtaact ccacagaagc                                                  20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gagagtaact ccacagaagc                                                  20

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(14)
<223> OTHER INFORMATION: Inosine

```
<400> SEQUENCE: 6
cagaaggcaa aaangagagt aactccacag aagc                          34

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (9)..(9)
<223> OTHER INFORMATION: Inosine

<400> SEQUENCE: 7
ggcaaaaang agagtaactc cacagaagc                                29

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 8
gagaguaacu ccacagaagc                                          20

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 9
agagtaacuc cacagaagct ccaaautc                                 28

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 10
agaguaacuc cacagaagcu ccaaautc                                 28

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
```

```
<223> OTHER INFORMATION: Description of Combined DNA/RNA Molecule:
      Synthetic primer

<400> SEQUENCE: 11
gagaguaacu ccacagaagc tccaaautc                                      29

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 12
gagaguaacu ccacagaagc uccaaautc                                      29

<210> SEQ ID NO 13
<211> LENGTH: 43
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(14)
<223> OTHER INFORMATION: Inosine

<400> SEQUENCE: 13
cagaaggcaa aaangagagt aactccacag aagctccaaa ttc                      43

<210> SEQ ID NO 14
<211> LENGTH: 49
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (14)..(14)
<223> OTHER INFORMATION: Inosine

<400> SEQUENCE: 14
cagaaggcaa aaangagagt aactccacag aagctccaaa ttctttata               49

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gagagtaact ccacagaagc                                                20

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 16
tttttttttt ttttttttgc tggtg                                          25

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<221> NAME/KEY: misc_feature
<222> LOCATION: (10)..(11)
<223> OTHER INFORMATION: BHQ-2

<400> SEQUENCE: 17
tguacuagga ggctgtaggc ataaattg                                       28

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gatcaacgtg tcaccgccta ttctattttt tttttttttt tttgctggtg               50

<210> SEQ ID NO 19
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aactgctgct taaatcttgc taccctttt tttttttttt tttgctggtg                50

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 20
utgaggcaua ctucaaagac tg                                             22

<210> SEQ ID NO 21
<211> LENGTH: 35
<212> TYPE: DNA
<213> ORGANISM: Artificial Sequence
<220> FEATURE:
<223> OTHER INFORMATION: Description of Artificial Sequence: Synthetic
      blocker sequence
<220> FEATURE:
<221> NAME/KEY: modified_base
<222> LOCATION: (18)..(19)
<223> OTHER INFORMATION: Inosine
```

<400> SEQUENCE: 21
gttgcatggt gctggtgnnc agaccaattt atgcc                                    35

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      blocker sequence
<220> FEATURE:
<221> NAME/KEY: modified_base
<222> LOCATION: (11)..(12)
<223> OTHER INFORMATION: Inosine

<400> SEQUENCE: 22
ggugcuggug nncagaccca auu                                                 23

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
actcttggac tctcagcaat gtc                                                 23

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
actcttggac tctctgtaat gtc                                                 23

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tttttttttt ttttttttgc tggtgaac                                            28

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tttttttttt ttttttttgc tggtgcgc                                            28

<210> SEQ ID NO 27
<211> LENGTH: 53
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 27
gatcaacgtg tcaccgccta ttctatttttt tttttttttt tttgctggtg aac        53

<210> SEQ ID NO 28
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gatcaacgtg tcaccgccta ttctatttttt tttttttttt tttgctggtg cgc        53

<210> SEQ ID NO 29
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aactgctgct taaatcttgc taccctttttt tttttttttt tttgctggtg aac        53

<210> SEQ ID NO 30
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aactgctgct taaatcttgc taccctttttt tttttttttt tttgctggtg cgc        53

<210> SEQ ID NO 31
<211> LENGTH: 41
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (7)..(8)
<223> OTHER INFORMATION: BHQ-2

<400> SEQUENCE: 31
accgaccttg aggcatactt caaagactgt gtgtttaaag a                      41

<210> SEQ ID NO 32
<211> LENGTH: 41
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: misc_feature
<222> LOCATION: (7)..(8)
<223> OTHER INFORMATION: BHQ-2

<400> SEQUENCE: 32
acctggatcg aagaatacat caaagactgt gtatttaagg a                      41
```

<210> SEQ ID NO 33
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
atagaagagc tgtcgtagtc tccgattttt tttttttttt tttgaagctc c          51

<210> SEQ ID NO 34
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gatcaacgtg tcaccgccta ttctattttt tttttttttt tttgaagctc c          51

<210> SEQ ID NO 35
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
aactgctgct taaatcttgc taccctttttt tttttttttt tttgaagctc c          51

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
atagaagagc tgtcgtagtc tccga                                       25

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gatcaacgtg tcaccgccta ttcta                                       25

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
aactgctgct taaatcttgc taccc                                       25

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tttttttttt tttttttga agctcc                                          26

<210> SEQ ID NO 40
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gatcaacgtg tcaccgccta ttctattttt tttttttttt tttgaagctc               50

<210> SEQ ID NO 41
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
aactgctgct taaatcttgc taccctttt tttttttttt tttgaagctc                50

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tttttttttt tttttttga agctc                                           25

<210> SEQ ID NO 43
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gatcaacgtg tcaccgccta ttctattttt tttttttttt tttgaagc                 48

<210> SEQ ID NO 44
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
aactgctgct taaatcttgc taccctttt tttttttttt tttgaagc                  48

```
<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tttttttttt tttttttga agc                                              23

<210> SEQ ID NO 46
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gatcaacgtg tcaccgccta ttctattttt tttttttttt gaagctcc                  48

<210> SEQ ID NO 47
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
aactgctgct taaatcttgc taccctttttt tttttttttt gaagctcc                 48

<210> SEQ ID NO 48
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gatcaacgtg tcaccgccta ttctattttt tttttttgaa gctcc                     45

<210> SEQ ID NO 49
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
aactgctgct taaatcttgc tacccttttt tttttttgaa gctcc                     45

<210> SEQ ID NO 50
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gatcaacgtg tcaccgccta ttctattttt tttttttttt tttgtagctc c              51

<210> SEQ ID NO 51
```

```
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gatcaacgtg tcaccgccta ttctattttt tttttttttt tttgtagc                  48

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tttttttttt ttttttttgt agctcc                                          26

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tttttttttt ttttttttgt agc                                             23

<210> SEQ ID NO 54
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tttttttttt tttttttttt tttttg                                          26

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 55
tttttttttu uutttuuutt tuuutg                                          26

<210> SEQ ID NO 56
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
```

<400> SEQUENCE: 56
ttuuutttuu utttuuutga agctcc					26

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 57
uuuuuuuuuu uuuuuuuga agctcc					26

<210> SEQ ID NO 58
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 58
ttutttuttt utttttttga agctcc					26

<210> SEQ ID NO 59
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 59
ttuuutttuu utttuuutga agctcc					26

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tttttttttt tttttttga agctcc					26

<210> SEQ ID NO 61
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tttttttttt tttttttga agctc					25

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tttttttttt ttttttttga agc                                           23

<210> SEQ ID NO 63
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gatcaacgtg tcaccgccta ttctattttt tttttttttt tttgaagctc c             51

<210> SEQ ID NO 64
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gatcaacgtg tcaccgccta ttctattttt tttttttttt tttgaagc                 48

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tttttttttt ttttttttga agctcc                                        26

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
tttttttttt ttttttttga agctc                                         25

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 67
ttutttuttt uttttttttga agctcc                                              26

<210> SEQ ID NO 68
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 68
ttutttuttt uttttttttga agctc                                               25

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 69
ttutttuttt uttttttttga agc                                                 23

<210> SEQ ID NO 70
<211> LENGTH: 48
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 70
gatcaacgtg tcaccgccta ttctattutt tutttutttu tttgaagc                       48

<210> SEQ ID NO 71
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 71
tttttttttt ttttttttga agcucc                                               26

<210> SEQ ID NO 72
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

```
<220> FEATURE:
<223> OTHER INFORMATION: Description of Combined DNA/RNA Molecule:
      Synthetic primer

<400> SEQUENCE: 72
tttttttttt ttttttttga agcucc                                          26

<210> SEQ ID NO 73
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 73
gatcaacgtg tcaccgccta ttctattttt tttttttttt tttgaagcuc c              51

<210> SEQ ID NO 74
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 74
gatcaacgtg tcaccgccta ttctattttt tttttttttt tttgaagcuc c              51

<210> SEQ ID NO 75
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 75
aactgctgct taaatcttgc tacccttttt tttttttttt tttgaagcuc c              51

<210> SEQ ID NO 76
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 76
aactgctgct taaatcttgc tacccttttt tttttttttt tttgaagcuc c              51

<210> SEQ ID NO 77
<211> LENGTH: 51
<212> TYPE: DNA
<213> ORGANISM: Artificial Sequence
```

```
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 77
gatcaacgtg tcaccgccta ttctattttt tttttttttt tttgaagcuc c        51

<210> SEQ ID NO 78
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gatcaacgtg tcaccgccta ttctattttt tttttttttt tttgtagctc c        51

<210> SEQ ID NO 79
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gatcaacgtg tcaccgccta ttctattttt tttttttttt tttgtagc             48

<210> SEQ ID NO 80
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
tttttttttt tttttttgt agctcc                                      26

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
tttttttttt tttttttgt agc                                         23

<210> SEQ ID NO 82
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tttttttttt tttttttgt agctc                                       25

<210> SEQ ID NO 83
<211> LENGTH: 51
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gatcaacgtg tcaccgccta ttctattttt tttttttttt tttttttttt g           51

<210> SEQ ID NO 84
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 84
gatcaacgtg tcaccgccta ttctattttt ttttuuuttt uuutttuuut g           51

<210> SEQ ID NO 85
<211> LENGTH: 48
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 85
gatcaacgtg tcaccgccta ttctattttt tttttttuu uttgaagc               48

<210> SEQ ID NO 86
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 86
gatcaacgtg tcaccgccta ttctattttt ttuuutttuu uttgaagctc c           51

<210> SEQ ID NO 87
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 87
tttttttttt tttuuuttga agctcc                                      26

<210> SEQ ID NO 88
<211> LENGTH: 48
<212> TYPE: DNA
<213> ORGANISM: Artificial Sequence
```

```
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 88
gatcaacgtg tcaccgccta ttctattttt tutttuttu tttgaagc                  48

<210> SEQ ID NO 89
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 89
gatcaacgtg tcaccgccta ttctattttt tutttuttu tttgaagctc c              51

<210> SEQ ID NO 90
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 90 tttttuttt utttutttga agctcc                                          26

<210> SEQ ID NO 91
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
tttttttttt tttttttga agctcc                                          26

<210> SEQ ID NO 92
<211> LENGTH: 48
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 92
gatcaacgtg tcaccgccta ttctattutu tutuuutttu tutgaagc                 48

<210> SEQ ID NO 93
<211> LENGTH: 26
<212> TYPE: DNA
```

<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

<400> SEQUENCE: 93
ttuuutttuu utttuuutgt agctcc                                         26

<210> SEQ ID NO 94
<211> LENGTH: 48
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

<400> SEQUENCE: 94
gatcaacgtg tcaccgccta ttctattutu tutuuutttu tutgtagc                 48

<210> SEQ ID NO 95
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 95
gatcaacgtg tcaccgccta ttctatttttt ttttttttttt ttgaagc                 47

<210> SEQ ID NO 96
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 96
gatcaacgtg tcaccgccta ttctatttttt ttttttttttt ttgtagc                 47

<210> SEQ ID NO 97
<211> LENGTH: 48
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

<400> SEQUENCE: 97
gatcaacgtg tcaccgccta ttctautuu tutttutttu uutgaagc                  48

<210> SEQ ID NO 98
<211> LENGTH: 48
<212> TYPE: DNA
<213> ORGANISM: Artificial Sequence
<220> FEATURE:
<223> OTHER INFORMATION: Description of Artificial Sequence: Synthetic primer
<220> FEATURE:

<223> OTHER INFORMATION: Description of Combined DNA/RNA Molecule:
        Synthetic primer

<400> SEQUENCE: 98
gatcaacgtg tcaccgccta ttctaututu tutttutttu uutgtagc          48

<210> SEQ ID NO 99
<211> LENGTH: 47
<212> TYPE: DNA
<213> ORGANISM: Artificial Sequence
<220> FEATURE:
<223> OTHER INFORMATION: Description of Artificial Sequence: Synthetic
        primer
<220> FEATURE:
<223> OTHER INFORMATION: Description of Combined DNA/RNA Molecule:
        Synthetic primer

<400> SEQUENCE: 99
gatcaacgtg tcaccgccta ttctatuttt utttutttut utgaagc            47

<210> SEQ ID NO 100
<211> LENGTH: 47
<212> TYPE: DNA
<213> ORGANISM: Artificial Sequence
<220> FEATURE:
<223> OTHER INFORMATION: Description of Artificial Sequence: Synthetic
        primer
<220> FEATURE:
<223> OTHER INFORMATION: Description of Combined DNA/RNA Molecule:
        Synthetic primer

<400> SEQUENCE: 100
gatcaacgtg tcaccgccta ttctatuttt utttutttut utgtagc            47

<210> SEQ ID NO 101
<211> LENGTH: 48
<212> TYPE: DNA
<213> ORGANISM: Artificial Sequence
<220> FEATURE:
<223> OTHER INFORMATION: Description of Artificial Sequence: Synthetic
        primer
<220> FEATURE:
<223> OTHER INFORMATION: Description of Combined DNA/RNA Molecule:
        Synthetic primer

<400> SEQUENCE: 101
gatcaacgtg tcaccgccta ttctattutu tutuuutttu tutgaagc           48

<210> SEQ ID NO 102
<211> LENGTH: 48
<212> TYPE: DNA
<213> ORGANISM: Artificial Sequence
<220> FEATURE:
<223> OTHER INFORMATION: Description of Artificial Sequence: Synthetic
        primer
<220> FEATURE:
<223> OTHER INFORMATION: Description of Combined DNA/RNA Molecule:
        Synthetic primer

<400> SEQUENCE: 102
gatcaacgtg tcaccgccta ttctattutu tutuuutttu tutgtagc           48

<210> SEQ ID NO 103
<211> LENGTH: 47
<212> TYPE: DNA
<213> ORGANISM: Artificial Sequence
<220> FEATURE:
<223> OTHER INFORMATION: Description of Artificial Sequence: Synthetic
        primer -continued

<400> SEQUENCE: 103
gatcaacgtg tcaccgccta ttctattttt tttttttttt ttgaagc    47

<210> SEQ ID NO 104
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gatcaacgtg tcaccgccta ttctattttt tttttttttt ttgtagc    47

<210> SEQ ID NO 105
<211> LENGTH: 42
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 105
cgtgtcaccg cctattctat tutututuuu tttututgaa gc    42

<210> SEQ ID NO 106
<211> LENGTH: 42
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 106
cgtgtcaccg cctattctat tutututuuu tttututgta gc    42

<210> SEQ ID NO 107
<211> LENGTH: 42
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 107
gatcaacgtg tcaccgcctt tutututuuu tttututgaa gc    42

<210> SEQ ID NO 108
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

```
<220> FEATURE:
<223> OTHER INFORMATION: Description of Combined DNA/RNA Molecule:
      Synthetic primer

<400> SEQUENCE: 108
gatcaacgtg tcaccgcctt tutututuuu tttututgta gc                              42

<210> SEQ ID NO 109
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 109
cgtgtcaccg cctattctat tutututuuu tttututgaa gctcc                           45

<210> SEQ ID NO 110
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 110
cgtgtcaccg cctattctat tutututuuu tttututgta gctcc                           45

<210> SEQ ID NO 111
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 111
gatcaacgtg tcaccgcctt tutututuuu tttututgaa gctcc                           45

<210> SEQ ID NO 112
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 112
gatcaacgtg tcaccgcctt tutututuuu tttututgta gctcc                           45

<210> SEQ ID NO 113
<211> LENGTH: 42
<212> TYPE: DNA
```

```
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 113
cgtgtcaccg cctattctat tutututuuu tttututgta gc                       42

<210> SEQ ID NO 114
<211> LENGTH: 48
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 114
gatcaacgtg tcaccgccta ttctattutu tutuuutttu tutgtagc                 48

<210> SEQ ID NO 115
<211> LENGTH: 48
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 115
gatcaacgtg tcaccgccta ttctaututu tuuutttutu tgaagctc                 48

<210> SEQ ID NO 116
<211> LENGTH: 48
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 116
gatcaacgtg tcaccgccta ttctaututu tuuutttutu tgtagctc                 48

<210> SEQ ID NO 117
<211> LENGTH: 48
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 117
gatcaacgtg tcaccgccta ttctatutut utuuutttut utgtagct                 48

<210> SEQ ID NO 118
<211> LENGTH: 48
```

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (47)..(47)
<223> OTHER INFORMATION: Inosine

<400> SEQUENCE: 118
gatcaacgtg tcaccgccta ttctattutu tutuuutttu tutgtanc                    48

<210> SEQ ID NO 119
<211> LENGTH: 46
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 119
gatcaacgtg tcaccgcctt tutututuuu tttututgta gctcca                      46

<210> SEQ ID NO 120
<211> LENGTH: 46
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 120
gatcaacgtg tcaccgcctt tutututuuu tttututgaa gctcca                      46

<210> SEQ ID NO 121
<211> LENGTH: 47
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 121
gatcaacgtg tcaccgcctt tutututuuu tttututgta gctccaa                     47

<210> SEQ ID NO 122
<211> LENGTH: 47
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
```

```
<400> SEQUENCE: 122
gatcaacgtg tcaccgcctt tutututuuu tttututgaa gctccaa              47

<210> SEQ ID NO 123
<211> LENGTH: 48
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 123
gatcaacgtg tcaccgcctt tutututuuu tttututgta gctccaaa             48

<210> SEQ ID NO 124
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 124
gatcaacgtg tcaccgcctt tutututuuu tttututgta gctccaaatt c         51

<210> SEQ ID NO 125
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 125
gatcaacgtg tcaccgcctt tutututuuu tttututgaa gctccaaatt c         51

<210> SEQ ID NO 126
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (41)..(41)
<223> OTHER INFORMATION: Inosine

<400> SEQUENCE: 126
gatcaacgtg tcaccgcctt tutututuuu tttututgta nctcc                45

<210> SEQ ID NO 127
<211> LENGTH: 45
<212> TYPE: DNA
<213> ORGANISM: Artificial Sequence
<220> FEATURE:
```

```
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 127
gatcaacgtg tcaccgcctt tutututuuu tttututgta gctcc              45

<210> SEQ ID NO 128
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 128
gatcaacgtg tcaccgcctt tutututuuu tttututgta gctcc              45

<210> SEQ ID NO 129
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 129
gatcaacgtg tcaccgcctt tutututuuu tttututgta gctcc              45

<210> SEQ ID NO 130
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 130
gatcaacgtg tcaccgcctt tutututuuu tttututgta gctcc              45

<210> SEQ ID NO 131
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<221> NAME/KEY: modified_base
<222> LOCATION: (38)..(38)
<223> OTHER INFORMATION: Inosine
<220> FEATURE:
<221> NAME/KEY: modified_base
<222> LOCATION: (41)..(41)
<223> OTHER INFORMATION: Inosine
```

<400> SEQUENCE: 131
gatcaacgtg tcaccgcctt tutututuuu tttututnta nctcc         45

<210> SEQ ID NO 132
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
gatcaacgtg tcaccgcctt tttttttttt tttttgtag c              41

<210> SEQ ID NO 133
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
gatcaacgtg tcaccgcctt tttttttttt tttttgtag ctc            43

<210> SEQ ID NO 134
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
gatcaacgtg tcaccgcctt tttttttttt tttttgaag ctc            43

<210> SEQ ID NO 135
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
gatcaacgtg tcaccgcctt tttttttttt tttttgtag ctcc           44

<210> SEQ ID NO 136
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
gatcaacgtg tcaccgcctt tttttttttt tttttgaag ctcc           44

<210> SEQ ID NO 137
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 137
gatcaacgtg tcaccgcctt tttttttttt tttttgtag ctcca          45

<210> SEQ ID NO 138
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
gatcaacgtg tcaccgcctt tttttttttt tttttgaag ctcca          45

<210> SEQ ID NO 139
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
gatcaacgtg tcaccgcctt tttttttttt tttttgtag ctccaa         46

<210> SEQ ID NO 140
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
gatcaacgtg tcaccgcctt tttttttttt tttttgaag ctccaa         46

<210> SEQ ID NO 141
<211> LENGTH: 38
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 141
gatcaacgtg tcaccgccuu uuuuuuuuu gaagctcc                  38

<210> SEQ ID NO 142
<211> LENGTH: 38
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 142
gatcaacgtg tcaccgccuu uuuuuuuuu gtagctcc                  38

<210> SEQ ID NO 143
<211> LENGTH: 38
<212> TYPE: DNA
```

<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 143
gatcaacgtg tcaccgccuu uuuuuuuuu gacgctcc                    38

<210> SEQ ID NO 144
<211> LENGTH: 38
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 144
gatcaacgtg tcaccgccuu uuuuuuuuu gaagcgcc                    38

<210> SEQ ID NO 145
<211> LENGTH: 38
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 145
gatcaacgtg tcaccgccuu uuuuuuuuu gacgcgcc                    38

<210> SEQ ID NO 146
<211> LENGTH: 38
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 146
gatcaacgtg tcaccgccuu uuuuuuuuu gcagcgcc                    38

<210> SEQ ID NO 147
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 147
gatcaacgtg tcaccgcctt tutututuuu tttututgac gctcc           45

<210> SEQ ID NO 148
<211> LENGTH: 45

```
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 148
gatcaacgtg tcaccgcctt tutututuuu tttututgaa gcgcc              45

<210> SEQ ID NO 149
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 149
gatcaacgtg tcaccgcctt tutututuuu tttututgac gcgcc              45

<210> SEQ ID NO 150
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 150
gatcaacgtg tcaccgcctt tutututuuu tttututgca gcgcc              45

<210> SEQ ID NO 151
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
gatcaacgtg tcaccgccta ttctattttt tttttttttt ttgtagctc          49

<210> SEQ ID NO 152
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
gatcaacgtg tcaccgccta ttctattttt tttttttttt ttgaagctc          49

<210> SEQ ID NO 153
<211> LENGTH: 49
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 153
gatcaacgtg tcaccgccta ttctattttt tttttttttt tgtagctcc        49

<210> SEQ ID NO 154
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
gatcaacgtg tcaccgccta ttctattttt tttttttttt tgaagctcc        49

<210> SEQ ID NO 155
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
gatcaacgtg tcaccgccta ttctattttt tttttttttt gtagctcca        49

<210> SEQ ID NO 156
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
gatcaacgtg tcaccgccta ttctattttt tttttttttt gaagctcca        49

<210> SEQ ID NO 157
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
gatcaacgtg tcaccgccta ttctattttt tttttttttg tagctccaa        49

<210> SEQ ID NO 158
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
gatcaacgtg tcaccgccta ttctattttt tttttttttg aagctccaa        49

<210> SEQ ID NO 159
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 159
gatcaacgtg tcaccgccta ttctattttt ttttttttt ttgtagctc                49

<210> SEQ ID NO 160
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
gatcaacgtg tcaccgccta ttctattttt ttttttttt ttgaagctc                49

<210> SEQ ID NO 161
<211> LENGTH: 39
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 161
gatcaacgtg tcaccgccuu uuuuuuuuu gaagctcca                           39

<210> SEQ ID NO 162
<211> LENGTH: 39
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 162
gatcaacgtg tcaccgccuu uuuuuuuuu gtagctcca                           39

<210> SEQ ID NO 163
<211> LENGTH: 40
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 163
gatcaacgtg tcaccgccuu uuuuuuuuu gaagctccaa                          40

<210> SEQ ID NO 164
<211> LENGTH: 40
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
```

<400> SEQUENCE: 164
gatcaacgtg tcaccgccuu uuuuuuuuuu gtagctccaa           40

<210> SEQ ID NO 165
<211> LENGTH: 46
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 165
gatcaacgtg tcaccgcctt tutututuuu tttututgta gctcca           46

<210> SEQ ID NO 166
<211> LENGTH: 47
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 166
gatcaacgtg tcaccgcctt tutututuuu tttututgta gctccaa           47

<210> SEQ ID NO 167
<211> LENGTH: 48
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 167
gatcaacgtg tcaccgcctt tutututuuu tttututgta gctccaaa           48

<210> SEQ ID NO 168
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
gatcaacgtg tcaccgccta ttctattttt ttttttttt ttgtagctcc           50

<210> SEQ ID NO 169
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
gatcaacgtg tcaccgccta ttctattttt ttttttttt ttgaagctcc           50

<210> SEQ ID NO 170
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
gatcaacgtg tcaccgccta ttctattttt tttttttttt tgtagctcca                    50

<210> SEQ ID NO 171
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
gatcaacgtg tcaccgccta ttctattttt tttttttttt tgaagctcca                    50

<210> SEQ ID NO 172
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
gatcaacgtg tcaccgccta ttctattttt tttttttgta gctcc                         45

<210> SEQ ID NO 173
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
gatcaacgtg tcaccgccta ttctattttt tttttttgaa gctcc                         45

<210> SEQ ID NO 174
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
gatcaacgtg tcaccgccta ttctattttt tttttttgta gctcca                        46

<210> SEQ ID NO 175
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
gatcaacgtg tcaccgccta ttctattttt tttttttgaa gctcca                        46

```
<210> SEQ ID NO 176
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
gatcaacgtg tcaccgcctt ttttttttttt tttttttgtag ctcc                    44

<210> SEQ ID NO 177
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
gatcaacgtg tcaccgcctt tttttttttt tttttgaag ctcc                       44

<210> SEQ ID NO 178
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 178
gatcaacgtg tcaccgcctt tttttttttt tttttgtag ctcca                      45

<210> SEQ ID NO 179
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 179
gatcaacgtg tcaccgcctt tttttttttt tttttgaag ctcca                      45

<210> SEQ ID NO 180
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
gatcaacgtg tcaccgccta ttctattttt tttttttgta gctccaa                   47

<210> SEQ ID NO 181
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 181
gatcaacgtg tcaccgccta ttctattttt tttttttgaa gctccaa                   47

<210> SEQ ID NO 182
```

```
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
gatcaacgtg tcaccgcctt ttttttttt tttttgtag ctccaa                  46

<210> SEQ ID NO 183
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
gatcaacgtg tcaccgcctt ttttttttt tttttgaag ctccaa                  46

<210> SEQ ID NO 184
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 184
gatcaacgtg tcaccgccta ttctattttt tttttttt ttgtagc                 47

<210> SEQ ID NO 185
<211> LENGTH: 37
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 185
gatcaacgtg tcaccgccuu uuuuuuuuu gaagctc                           37

<210> SEQ ID NO 186
<211> LENGTH: 37
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer

<400> SEQUENCE: 186
gatcaacgtg tcaccgccuu uuuuuuuuu gtagctc                           37

<210> SEQ ID NO 187
<211> LENGTH: 44
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 187
gatcaacgtg tcaccgccta ttctattttt tttttttgta gctc          44

<210> SEQ ID NO 188
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
gatcaacgtg tcaccgccta ttctattttt tttttttgaa gctc          44

<210> SEQ ID NO 189
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
gatcaacgtg tcaccgcctt tttttttttt tttttgtag ctc            43

<210> SEQ ID NO 190
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
gatcaacgtg tcaccgcctt tttttttttt tttttgaag ctc            43

<210> SEQ ID NO 191
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
aactccacag aagctccaaa ttc                                 23

<210> SEQ ID NO 192
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
agagtaactc cacagaagct ccaaattc                            28

<210> SEQ ID NO 193
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 193
gagagtaact ccacagaagc tc                                              22

<210> SEQ ID NO 194
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
gagagtaact ccacagaagc                                                 20

<210> SEQ ID NO 195
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
gagagtaact ccacagaagc                                                 20

<210> SEQ ID NO 196
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: a, c, t, g, unknown or other

<400> SEQUENCE: 196
cagaaggcaa aaangagagt aactccacag aagc                                 34

<210> SEQ ID NO 197
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(9)
<223> OTHER INFORMATION: a, c, t, g, unknown or other

<400> SEQUENCE: 197
ggcaaaaang agagtaactc cacagaagc                                       29

<210> SEQ ID NO 198
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
gagagtaact ccacagaagc                                                 20

<210> SEQ ID NO 199
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
agagtaactc cacagaagct ccaaattc                                           28

<210> SEQ ID NO 200
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
agagtaactc cacagaagct ccaaattc                                           28

<210> SEQ ID NO 201
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
gagagtaact ccacagaagc tccaaattc                                          29

<210> SEQ ID NO 202
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
gagagtaact ccacagaagc tccaaattc                                          29

<210> SEQ ID NO 203
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: a, c, t, g, unknown or other

<400> SEQUENCE: 203
cagaaggcaa aaangagagt aactccacag aagctccaaa ttc                          43

<210> SEQ ID NO 204
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(14)
<223> OTHER INFORMATION: a, c, t, g, unknown or other
```

<400> SEQUENCE: 204
cagaaggcaa aaangagagt aactccacag aagctccaaa ttctttata                49

<210> SEQ ID NO 205
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
gagagtaact ccacagaagc                                                20

<210> SEQ ID NO 206
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
tttttttttt ttttttttgc tggtg                                          25

<210> SEQ ID NO 207
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
tgtactagga ggctgtaggc ataaattg                                       28

<210> SEQ ID NO 208
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
gatcaacgtg tcaccgccta ttctattttt tttttttttt tttgctggtg               50

<210> SEQ ID NO 209
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
aactgctgct taaatcttgc tacccttttt tttttttttt tttgctggtg               50

<210> SEQ ID NO 210
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 210
ttgaggcata cttcaaagac tg                                              22

<210> SEQ ID NO 211
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (18)..(19)
<223> OTHER INFORMATION: a, c, t, g, unknown or other

<400> SEQUENCE: 211
gttgcatggt gctggtgnnc agaccaattt atgcc                                35

<210> SEQ ID NO 212
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(12)
<223> OTHER INFORMATION: a, c, t, g, unknown or other

<400> SEQUENCE: 212
ggtgctggtg nncagaccca att                                             23

<210> SEQ ID NO 213
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
actcttggac tctcagcaat gtc                                             23

<210> SEQ ID NO 214
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
actcttggac tctctgtaat gtc                                             23

<210> SEQ ID NO 215
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
tttttttttt tttttttgc tggtgaac                                         28

<210> SEQ ID NO 216
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216 ttttttttttt ttttttttgc tggtgcgc                                      28

<210> SEQ ID NO 217
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
gatcaacgtg tcaccgccta ttctattttt tttttttttt tttgctggtg aac           53

<210> SEQ ID NO 218
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
gatcaacgtg tcaccgccta ttctattttt tttttttttt tttgctggtg cgc           53

<210> SEQ ID NO 219
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
aactgctgct taaatcttgc taccctttttt tttttttttt tttgctggtg aac          53

<210> SEQ ID NO 220
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
aactgctgct taaatcttgc taccctttttt tttttttttt tttgctggtg cgc          53

<210> SEQ ID NO 221
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
accgaccttg aggcatactt caaagactgt gtgtttaaag a                        41

<210> SEQ ID NO 222
<211> LENGTH: 41
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
acctggatcg aagaatacat caaagactgt gtatttaagg a                41

<210> SEQ ID NO 223
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
atagaagagc tgtcgtagtc tccgattttt tttttttttt tttgaagctc c      51

<210> SEQ ID NO 224
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224
gatcaacgtg tcaccgccta ttctattttt tttttttttt tttgaagctc c      51

<210> SEQ ID NO 225
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225
aactgctgct taaatcttgc tacccttttt tttttttttt tttgaagctc c      51

<210> SEQ ID NO 226
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226
atagaagagc tgtcgtagtc tccga                                   25

<210> SEQ ID NO 227
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227
gatcaacgtg tcaccgccta ttcta                                   25

<210> SEQ ID NO 228
<211> LENGTH: 25
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 228
aactgctgct taaatcttgc taccc                                               25

<210> SEQ ID NO 229
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 229
tttttttttt tttttttga agctcc                                               26

<210> SEQ ID NO 230
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 230
gatcaacgtg tcaccgccta ttctattttt tttttttttt tttgaagctc                    50

<210> SEQ ID NO 231
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 231
aactgctgct taaatcttgc taccctttt tttttttttt tttgaagctc                     50

<210> SEQ ID NO 232
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 232
tttttttttt tttttttga agctc                                                25

<210> SEQ ID NO 233
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 233
gatcaacgtg tcaccgccta ttctattttt tttttttttt tttgaagc                      48

<210> SEQ ID NO 234
<211> LENGTH: 48
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 234
aactgctgct taaatcttgc tacccttttt tttttttttt tttgaagc                         48

<210> SEQ ID NO 235
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 235
tttttttttt ttttttttga agc                                                   23

<210> SEQ ID NO 236
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 236
gatcaacgtg tcaccgccta ttctattttt tttttttttt gaagctcc                        48

<210> SEQ ID NO 237
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 237
aactgctgct taaatcttgc tacccttttt tttttttttt gaagctcc                         48

<210> SEQ ID NO 238
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 238
gatcaacgtg tcaccgccta ttctattttt tttttttgaa gctcc                           45

<210> SEQ ID NO 239
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 239
aactgctgct taaatcttgc tacccttttt tttttttgaa gctcc                           45

<210> SEQ ID NO 240
<211> LENGTH: 51
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 240
gatcaacgtg tcaccgccta ttctattttt tttttttttt tttgtagctc c        51

<210> SEQ ID NO 241
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 241
gatcaacgtg tcaccgccta ttctattttt tttttttttt tttgtagc             48

<210> SEQ ID NO 242
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 242
tttttttttt tttttttgt agctcc                                      26

<210> SEQ ID NO 243
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 243
tttttttttt tttttttgt agc                                         23

<210> SEQ ID NO 244
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 244
tttttttttt tttttttttt tttttg                                     26

<210> SEQ ID NO 245
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 245
gatcaacgtg tcaccgccta ttctattttt tttttttttt tttttttttt g         51

<210> SEQ ID NO 246
<211> LENGTH: 26
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 246
tttttttttt tttttttga agctcc                                                26

<210> SEQ ID NO 247
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
tttttttttt tttttttga agctcc                                                26

<210> SEQ ID NO 248
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 248
tttttttttt tttttttga agctcc                                                26

<210> SEQ ID NO 249
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 249
tttttttttt tttttttga agctcc                                                26

<210> SEQ ID NO 250
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 250
tttttttttt tttttttga agctcc                                                26

<210> SEQ ID NO 251
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
tttttttttt tttttttga agctc                                                 25

<210> SEQ ID NO 252
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 252
tttttttttt tttttttga agc                                              23

<210> SEQ ID NO 253
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 253
gatcaacgtg tcaccgccta ttctattttt tttttttttt tttgaagctc c              51

<210> SEQ ID NO 254
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 254
gatcaacgtg tcaccgccta ttctattttt tttttttttt tttgaagc                  48

<210> SEQ ID NO 255
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 255
tttttttttt tttttttga agctcc                                           26

<210> SEQ ID NO 256
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 256
tttttttttt tttttttga agctc                                            25

<210> SEQ ID NO 257
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 257
tttttttttt tttttttga agctcc                                           26

<210> SEQ ID NO 258
<211> LENGTH: 25
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 258
tttttttttt ttttttttga agctc                                        25

<210> SEQ ID NO 259
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
tttttttttt ttttttttga agc                                          23

<210> SEQ ID NO 260
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
gatcaacgtg tcaccgccta ttctattttt tttttttttt tttgaagc               48

<210> SEQ ID NO 261
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
tttttttttt ttttttttga agctcc                                       26

<210> SEQ ID NO 262
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
tttttttttt ttttttttga agctcc                                       26

<210> SEQ ID NO 263
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
gatcaacgtg tcaccgccta ttctattttt tttttttttt tttgaagctc c           51

<210> SEQ ID NO 264
<211> LENGTH: 51
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 264
gatcaacgtg tcaccgccta ttctattttt tttttttttt tttgaagctc c          51

<210> SEQ ID NO 265
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
aactgctgct taaatcttgc tacccttttt tttttttttt tttgaagctc c          51

<210> SEQ ID NO 266
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
aactgctgct taaatcttgc tacccttttt tttttttttt tttgaagctc c          51

<210> SEQ ID NO 267
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
gatcaacgtg tcaccgccta ttctattttt tttttttttt tttgaagctc c          51

<210> SEQ ID NO 268
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
gatcaacgtg tcaccgccta ttctattttt tttttttttt tttgtagctc c          51

<210> SEQ ID NO 269
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
gatcaacgtg tcaccgccta ttctattttt tttttttttt tttgtagc             48

<210> SEQ ID NO 270
<211> LENGTH: 26
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 270
tttttttttt tttttttgt agctcc                                              26

<210> SEQ ID NO 271
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
tttttttttt tttttttgt agc                                                 23

<210> SEQ ID NO 272
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
tttttttttt tttttttgt agctc                                               25

<210> SEQ ID NO 273
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
gatcaacgtg tcaccgccta ttctattttt tttttttttt tttttttttt g                 51

<210> SEQ ID NO 274
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
gatcaacgtg tcaccgccta ttctattttt tttttttttt tttttttttt g                 51

<210> SEQ ID NO 275
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
gatcaacgtg tcaccgccta ttctattttt tttttttttt tttgaagc                     48

<210> SEQ ID NO 276
<211> LENGTH: 51
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 276
gatcaacgtg tcaccgccta ttctattttt tttttttttt tttgaagctc c           51

<210> SEQ ID NO 277
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 277
tttttttttt tttttttga agctcc                                        26

<210> SEQ ID NO 278
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 278
gatcaacgtg tcaccgccta ttctattttt tttttttttt tttgaagc               48

<210> SEQ ID NO 279
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 279
gatcaacgtg tcaccgccta ttctattttt tttttttttt tttgaagctc c           51

<210> SEQ ID NO 280
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 280
tttttttttt tttttttga agctcc                                        26

<210> SEQ ID NO 281
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 281
tttttttttt tttttttga agctcc                                        26

<210> SEQ ID NO 282
<211> LENGTH: 48
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 282
gatcaacgtg tcaccgccta ttctattttt tttttttttt tttgaagc                48

<210> SEQ ID NO 283
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 283 ttttttttt ttttttttgt agctcc                                          26

<210> SEQ ID NO 284
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 284
gatcaacgtg tcaccgccta ttctattttt tttttttttt tttgtagc                48

<210> SEQ ID NO 285
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 285
gatcaacgtg tcaccgccta ttctattttt tttttttttt ttgaagc                 47

<210> SEQ ID NO 286
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 286
gatcaacgtg tcaccgccta ttctattttt tttttttttt ttgtagc                 47

<210> SEQ ID NO 287
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 287
gatcaacgtg tcaccgccta ttctattttt tttttttttt tttgaagc                48

<210> SEQ ID NO 288
<211> LENGTH: 48
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 288
gatcaacgtg tcaccgccta ttctattttt tttttttttt tttgtagc                48

<210> SEQ ID NO 289
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 289
gatcaacgtg tcaccgccta ttctattttt tttttttttt ttgaagc                 47

<210> SEQ ID NO 290
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 290
gatcaacgtg tcaccgccta ttctattttt tttttttttt ttgtagc                 47

<210> SEQ ID NO 291
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 291
gatcaacgtg tcaccgccta ttctattttt tttttttttt tttgaagc                48

<210> SEQ ID NO 292
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 292
gatcaacgtg tcaccgccta ttctattttt tttttttttt tttgtagc                48

<210> SEQ ID NO 293
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 293
gatcaacgtg tcaccgccta ttctattttt tttttttttt ttgaagc                 47

<210> SEQ ID NO 294
<211> LENGTH: 47
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 294
gatcaacgtg tcaccgccta ttctattttt ttttttttt ttgtagc                    47

<210> SEQ ID NO 295
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 295
cgtgtcaccg cctattctat tttttttttt tttttttgaa gc                        42

<210> SEQ ID NO 296
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 296
cgtgtcaccg cctattctat tttttttttt tttttttgta gc                        42

<210> SEQ ID NO 297
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 297
gatcaacgtg tcaccgcctt tttttttttt tttttttgaa gc                        42

<210> SEQ ID NO 298
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 298
gatcaacgtg tcaccgcctt tttttttttt tttttttgta gc                        42

<210> SEQ ID NO 299
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 299
cgtgtcaccg cctattctat tttttttttt tttttttgaa gctcc                     45

<210> SEQ ID NO 300
<211> LENGTH: 45
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 300
cgtgtcaccg cctattctat tttttttttt tttttttgta gctcc            45

<210> SEQ ID NO 301
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301
gatcaacgtg tcaccgcctt tttttttttt tttttttgaa gctcc            45

<210> SEQ ID NO 302
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302
gatcaacgtg tcaccgcctt tttttttttt tttttttgta gctcc            45

<210> SEQ ID NO 303
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303
cgtgtcaccg cctattctat tttttttttt tttttttgta gc               42

<210> SEQ ID NO 304
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304
gatcaacgtg tcaccgccta ttctattttt tttttttttt tttgtagc         48

<210> SEQ ID NO 305
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305
gatcaacgtg tcaccgccta ttctattttt tttttttttt tgaagctc         48

<210> SEQ ID NO 306
<211> LENGTH: 48
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 306
gatcaacgtg tcaccgccta ttctattttt tttttttttt tgtagctc                    48

<210> SEQ ID NO 307
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
gatcaacgtg tcaccgccta ttctattttt tttttttttt ttgtagct                    48

<210> SEQ ID NO 308
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
gatcaacgtg tcaccgccta ttctattttt tttttttttt tttgtagc                    48

<210> SEQ ID NO 309
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
gatcaacgtg tcaccgcctt tttttttttt tttttttgta gctcca                      46

<210> SEQ ID NO 310
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 310
gatcaacgtg tcaccgcctt tttttttttt tttttttgaa gctcca                      46

<210> SEQ ID NO 311
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 311
gatcaacgtg tcaccgcctt tttttttttt tttttttgta gctccaa                     47

<210> SEQ ID NO 312
<211> LENGTH: 47
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 312
gatcaacgtg tcaccgcctt tttttttttt tttttttgaa gctccaa                47

<210> SEQ ID NO 313
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
gatcaacgtg tcaccgcctt tttttttttt tttttttgta gctccaaa               48

<210> SEQ ID NO 314
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
gatcaacgtg tcaccgcctt tttttttttt tttttttgta gctccaaatt c           51

<210> SEQ ID NO 315
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
gatcaacgtg tcaccgcctt tttttttttt tttttttgaa gctccaaatt c           51

<210> SEQ ID NO 316
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
gatcaacgtg tcaccgcctt tttttttttt tttttttgta gctcc                  45

<210> SEQ ID NO 317
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
gatcaacgtg tcaccgcctt tttttttttt tttttttgta gctcc                  45

<210> SEQ ID NO 318
<211> LENGTH: 45
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 318
gatcaacgtg tcaccgcctt tttttttttt tttttttgta gctcc            45

<210> SEQ ID NO 319
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319
gatcaacgtg tcaccgcctt tttttttttt tttttttgta gctcc            45

<210> SEQ ID NO 320
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320
gatcaacgtg tcaccgcctt tttttttttt tttttttgta gctcc            45

<210> SEQ ID NO 321
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321
gatcaacgtg tcaccgcctt tttttttttt tttttttgta gctcc            45

<210> SEQ ID NO 322
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322
gatcaacgtg tcaccgcctt tttttttttt tttttgtag c                 41

<210> SEQ ID NO 323
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323
gatcaacgtg tcaccgcctt tttttttttt tttttgtag ctc               43

<210> SEQ ID NO 324
<211> LENGTH: 43
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 324
gatcaacgtg tcaccgcctt tttttttttt tttttttgaag ctc                    43

<210> SEQ ID NO 325
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
gatcaacgtg tcaccgcctt tttttttttt tttttgtag ctcc                     44

<210> SEQ ID NO 326
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
gatcaacgtg tcaccgcctt tttttttttt tttttgaag ctcc                     44

<210> SEQ ID NO 327
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
gatcaacgtg tcaccgcctt tttttttttt tttttgtag ctcca                    45

<210> SEQ ID NO 328
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
gatcaacgtg tcaccgcctt tttttttttt tttttgaag ctcca                    45

<210> SEQ ID NO 329
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
gatcaacgtg tcaccgcctt tttttttttt tttttgtag ctccaa                   46

<210> SEQ ID NO 330
<211> LENGTH: 46
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 330
gatcaacgtg tcaccgcctt tttttttttt tttttttgaag ctccaa                    46

<210> SEQ ID NO 331
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 331
gatcaacgtg tcaccgcctt tttttttttt gaagctcc                              38

<210> SEQ ID NO 332
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 332
gatcaacgtg tcaccgcctt tttttttttt gtagctcc                              38

<210> SEQ ID NO 333
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 333
gatcaacgtg tcaccgcctt tttttttttt gacgctcc                              38

<210> SEQ ID NO 334
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334
gatcaacgtg tcaccgcctt tttttttttt gaagcgcc                              38

<210> SEQ ID NO 335
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335
gatcaacgtg tcaccgcctt tttttttttt gacgcgcc                              38

<210> SEQ ID NO 336
<211> LENGTH: 38
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 336
gatcaacgtg tcaccgcctt ttttttttt gcagcgcc                          38

<210> SEQ ID NO 337
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 337
gatcaacgtg tcaccgcctt tttttttttt tttttttgac gctcc                 45

<210> SEQ ID NO 338
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
gatcaacgtg tcaccgcctt tttttttttt tttttttgaa gcgcc                 45

<210> SEQ ID NO 339
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
gatcaacgtg tcaccgcctt tttttttttt tttttttgac gcgcc                 45

<210> SEQ ID NO 340
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
gatcaacgtg tcaccgcctt tttttttttt tttttttgca gcgcc                 45

<210> SEQ ID NO 341
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
gatcaacgtg tcaccgccta ttctattttt tttttttttt ttgtagctc             49

<210> SEQ ID NO 342
<211> LENGTH: 49
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 342
gatcaacgtg tcaccgccta ttctattttt tttttttttt ttgaagctc                49

<210> SEQ ID NO 343
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
gatcaacgtg tcaccgccta ttctattttt tttttttttt tgtagctcc                49

<210> SEQ ID NO 344
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
gatcaacgtg tcaccgccta ttctattttt tttttttttt tgaagctcc                49

<210> SEQ ID NO 345
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 345
gatcaacgtg tcaccgccta ttctattttt tttttttttt gtagctcca                49

<210> SEQ ID NO 346
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 346
gatcaacgtg tcaccgccta ttctattttt tttttttttt gaagctcca                49

<210> SEQ ID NO 347
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 347
gatcaacgtg tcaccgccta ttctattttt tttttttttg tagctccaa                49

<210> SEQ ID NO 348
<211> LENGTH: 49
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 348
gatcaacgtg tcaccgccta ttctattttt tttttttttg aagctccaa         49

<210> SEQ ID NO 349
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 349
gatcaacgtg tcaccgccta ttctattttt tttttttttt ttgtagctc         49

<210> SEQ ID NO 350
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 350
gatcaacgtg tcaccgccta ttctattttt tttttttttt ttgaagctc         49

<210> SEQ ID NO 351
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 351
gatcaacgtg tcaccgcctt tttttttttt gaagctcca         39

<210> SEQ ID NO 352
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 352
gatcaacgtg tcaccgcctt tttttttttt gtagctcca         39

<210> SEQ ID NO 353
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 353
gatcaacgtg tcaccgcctt tttttttttt gaagctccaa         40

<210> SEQ ID NO 354
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
gatcaacgtg tcaccgcctt tttttttttt gtagctccaa                           40

<210> SEQ ID NO 355
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 355
gatcaacgtg tcaccgcctt tttttttttt tttttttgta gctcca                    46

<210> SEQ ID NO 356
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 356
gatcaacgtg tcaccgcctt tttttttttt tttttttgta gctccaa                   47

<210> SEQ ID NO 357
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 357
gatcaacgtg tcaccgcctt tttttttttt tttttttgta gctccaaa                  48

<210> SEQ ID NO 358
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 358
gatcaacgtg tcaccgccta ttctatttttt tttttttttt ttgtagctcc               50

<210> SEQ ID NO 359
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 359
gatcaacgtg tcaccgccta ttctatttttt tttttttttt ttgaagctcc               50

<210> SEQ ID NO 360
<211> LENGTH: 50
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 360
gatcaacgtg tcaccgccta ttctattttt tttttttttt tgtagctcca                    50

<210> SEQ ID NO 361
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 361
gatcaacgtg tcaccgccta ttctattttt tttttttttt tgaagctcca                    50

<210> SEQ ID NO 362
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 362
gatcaacgtg tcaccgccta ttctattttt tttttttgta gctcc                         45

<210> SEQ ID NO 363
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 363
gatcaacgtg tcaccgccta ttctattttt tttttttgaa gctcc                         45

<210> SEQ ID NO 364
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 364
gatcaacgtg tcaccgccta ttctattttt tttttttgta gctcca                        46

<210> SEQ ID NO 365
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 365
gatcaacgtg tcaccgccta ttctattttt tttttttgaa gctcca                        46

<210> SEQ ID NO 366
<211> LENGTH: 44
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 366
gatcaacgtg tcaccgcctt tttttttttt tttttgtag ctcc                        44

<210> SEQ ID NO 367
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 367
gatcaacgtg tcaccgcctt tttttttttt tttttgaag ctcc                        44

<210> SEQ ID NO 368
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 368
gatcaacgtg tcaccgcctt tttttttttt tttttgtag ctcca                       45

<210> SEQ ID NO 369
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 369
gatcaacgtg tcaccgcctt tttttttttt tttttgaag ctcca                       45

<210> SEQ ID NO 370
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 370
gatcaacgtg tcaccgccta ttctattttt tttttttgta gctccaa                    47

<210> SEQ ID NO 371
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 371
gatcaacgtg tcaccgccta ttctattttt tttttttgaa gctccaa                    47

<210> SEQ ID NO 372
<211> LENGTH: 46
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 372
gatcaacgtg tcaccgcctt tttttttttt tttttgtag ctccaa                    46

<210> SEQ ID NO 373
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 373
gatcaacgtg tcaccgcctt tttttttttt tttttgaag ctccaa                    46

<210> SEQ ID NO 374
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 374
gatcaacgtg tcaccgccta ttctattttt tttttttttt ttgtagc                  47

<210> SEQ ID NO 375
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 375
gatcaacgtg tcaccgcctt tttttttttt gaagctc                             37

<210> SEQ ID NO 376
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 376
gatcaacgtg tcaccgcctt tttttttttt gtagctc                             37

<210> SEQ ID NO 377
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 377
gatcaacgtg tcaccgccta ttctattttt tttttttgta gctc                     44

<210> SEQ ID NO 378
<211> LENGTH: 44
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 378
gatcaacgtg tcaccgccta ttctattttt ttttttgaa gctc                    44

<210> SEQ ID NO 379
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 379
gatcaacgtg tcaccgcctt tttttttttt tttttgtag ctc                     43

<210> SEQ ID NO 380
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 380
gatcaacgtg tcaccgcctt tttttttttt tttttgaag ctc                     43

<210> SEQ ID NO 381
<211> LENGTH: 10
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 381
tguacuagga                                                         10

<210> SEQ ID NO 382
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 382
ggctgtaggc ataaattg                                                18

<210> SEQ ID NO 383
<211> LENGTH: 7
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 383 accgacc                                                             7

<210> SEQ ID NO 384
```

```
<210> SEQ ID NO 384
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 384
ttgaggcata cttcaaagac tgtgtgttta aaga                                34

<210> SEQ ID NO 385
<211> LENGTH: 7
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 385 acctgga                                                               7

<210> SEQ ID NO 386
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 386
tcgaagaata catcaaagac tgtgtattta agga                                34

<210> SEQ ID NO 387
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 387
catgcaactt tttcacctct gccta                                          25

<210> SEQ ID NO 388
<211> LENGTH: 33
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe
<220> FEATURE:
<221> NAME/KEY: misc_feature
<222> LOCATION: (16)..(17)
<223> OTHER INFORMATION: BHQ-2

<400> SEQUENCE: 388
ccaagctgtg ccttgggtgg cuugggggca ugg                                 33

<210> SEQ ID NO 389
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 389
catgcaactt tttcacctct gccta                                          25

<210> SEQ ID NO 390
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 390
ccaagctgtg ccttgggtgg ctttggggca tgg                                 33

<210> SEQ ID NO 391
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 391
ccaagctgtg ccttgg                                                    16

<210> SEQ ID NO 392
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: Description of Combined DNA/RNA Molecule:
      Synthetic probe

<400> SEQUENCE: 392
gtggcuuugg ggcaugg                                                   17

<210> SEQ ID NO 393
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 393
gatcaacgtg tcaccgccta ttctattttt tttttttttt ttgatgctc                49

<210> SEQ ID NO 394
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 394
gatcaacgtg tcaccgccta ttctattttt tttttttttt ttttagctc                49

<210> SEQ ID NO 395
<211> LENGTH: 49

```
<210> SEQ ID NO 395
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 395
gatcaacgtg tcaccgccta ttctattttt tttttttttt ttgaagcgc            49

<210> SEQ ID NO 396
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 396
gatcaacgtg tcaccgccta ttctattttt tttttttttt ttgaggctc            49

<210> SEQ ID NO 397
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 397
gatcaacgtg tcaccgccta ttctattttt tttttttttt ttgatgctc            49

<210> SEQ ID NO 398
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 398
gatcaacgtg tcaccgccta ttctattttt tttttttttt ttttagctc            49

<210> SEQ ID NO 399
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 399
gatcaacgtg tcaccgccta ttctattttt tttttttttt ttgaagcgc            49

<210> SEQ ID NO 400
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 400
gatcaacgtg tcaccgccta ttctattttt tttttttttt ttgaggctc            49

<210> SEQ ID NO 401
<211> LENGTH: 97
<212> TYPE: DNA
```

```
<213> ORGANISM: Hepatitis B virus
<220> FEATURE:
<221> NAME/KEY: misc_feature
<223> OTHER INFORMATION: HBV DNA at polyadenylation site

<400> SEQUENCE: 401
ggggcatgga cattgacccg tataaagaat ttggagcttc tgtggagtta ctctcttttt      60
tgcccttctg acttctttcc ttctattcga gatctcc                              97

<210> SEQ ID NO 402
<211> LENGTH: 65
<212> TYPE: RNA
<213> ORGANISM: Hepatitis B virus
<220> FEATURE:
<221> NAME/KEY: misc_feature
<223> OTHER INFORMATION: HBV pgRNA at polyadenylation site

<400> SEQUENCE: 402
ggggcaugga cauugacccg uauaaagaau uuggagcuuc aaaaaaaaaa aaaaaaaaa      60 aaaaa                                                                 65

<210> SEQ ID NO 403
<211> LENGTH: 18
<212> TYPE: DNA
<213> ORGANISM: Artificial Sequence
<220> FEATURE:
<223> OTHER INFORMATION: Reverse Primer poly-T section

<400> SEQUENCE: 403
tttttttttt tttttttt                                                   18
```

COMPOSITIONS AND METHODS FOR AMPLIFICATION AND DETECTION OF HEPATITIS B VIRUS RNA, INCLUDING HBV RNA TRANSCRIBED FROM CCCDNA

FIELD OF THE INVENTION

The present disclosure relates to the field of in vitro viral diagnostics. Within this field, the present invention concerns the amplification and detection of a target nucleic acid that may be present in a sample and particularly, the specific amplification and detection of a target nucleic acid comprising sequence variations and/or individual mutations of Hepatitis B Virus (HBV), in particular, HBV RNA (in particular, HBV RNA derived from covalently-closed circular double-stranded DNA (cccDNA) such as HBV pre-genomic RNA (pgRNA)), using at least one reverse transcription (RT) primer and at least one competitive blocking oligonucleotide, to prevent the amplification and detection of homologous genomic HBV DNA. The invention further provides methods of, reaction mixtures for, and kits containing oligonucleotides (such as a reverse transcription (RT) primer and competitive blocking oligonucleotides) for the amplification and detection of circulating HBV RNA.

BACKGROUND OF THE INVENTION

Hepatitis is inflammation of the liver, which may be caused by a family of viral infections that affect the liver, the most common types being Hepatitis A, Hepatitis B, and Hepatitis C. Hepatitis A, Hepatitis B, and Hepatitis C are diseases caused by three different viruses.

Hepatitis B is an infectious disease of the liver caused by the Hepatitis B virus (HBV). HBV can cause both acute and/or chronic infections. During initial infection, many people are asymptomatic, whereas some develop rapid onset of sickness (including vomiting, yellowish skin, tiredness, dark urine and abdominal pain). Chronic hepatitis B preferentially afflicts those infected around the time of birth. Most of those individuals with chronic disease are also asymptomatic, but may eventually develop cirrhosis and liver cancer. These complications result in the death of 15 to 25% of those with chronic disease. HBV is, in general, transmitted by exposure to infectious blood or body fluids, for example, when blood, semen, or another body fluid from a person infected with the HBV enters the body of someone who is not infected. This can happen through sexual contact; sharing needles, syringes, or other drug-injection equipment; or from mother to baby at birth. Infection around the time of birth or from contact with other people's blood during childhood is the most frequent method by which hepatitis B is acquired in areas where the disease is common. In areas where the disease is rare, intravenous drug use and sexual intercourse are the most frequent routes of infection. Other risk factors include working in healthcare, blood transfusions, dialysis, living with an infected person, travel in countries where the infection rate is high, and living in an institution. An HBV infection can be diagnosed 30-60 days after exposure. The diagnosis is then usually confirmed by testing the blood for parts of the HBV virus and for antibodies against the HBV virus.

The HBV infection has been preventable by vaccination since 1982. The World Health Organization (WHO) recommends vaccination in the first day of life, if possible, with subsequent doses needed to ensure longer term protection. For those individuals with chronic hepatitis B diseases, antiviral medication such as tenofovir or interferon may be useful, while liver transplantation is sometimes useful for those with cirrhosis.

There are therapies available to manage the disease, however, the cure rate is low. In the absence of curative therapy, lifelong adherence to anti-viral medications is required. Removal of the therapy often allows for a rebound in HBV titers, due to the inability of current therapies to directly target the reservoir of HBV episomal genomes in the infected cell nuclei.

The virus life cycle for HBV alternates between DNA and RNA forms. The infectious HBV particle contains an incompletely double stranded DNA genome (relaxed-circle DNA or rcDNA). In an infected cell, the HBV DNA replication is completed to form a covalently-closed circular double-stranded DNA (cccDNA) in the nucleus of the host cell. Transcription from this DNA genome generates a variety of messenger RNA forms, which code for the proteins in the structure of the virus (core and surface proteins), the e antigen, the viral polymerase, and the X antigen. One mRNA form, known as the pre-genomic RNA (pgRNA), also serves as the template for the reverse transcription activity of the viral polymerase, which produces new copies of the rcDNA in encapsidated, secreted viral particles. Some evidence shows that some proportion of encapsidated pgRNA is released without being reverse-transcribed, so that the production of an infected cell includes both rcDNA and pgRNA-containing viral particles. In addition, there are multiple spliced RNA variants, some of which are also reverse transcribed into incomplete forms of HBV DNA and secreted. Integration of the HBV genome into a host chromosome is not a part of the replication cycle, as this cannot produce complete pgRNA molecules; however, it is a common occurrence and can result in host cells that produce smaller, truncated, or fusion mRNAs, which contribute to the secretion of surface antigen containing subviral particles.

Below, in Table 1, is list of the HBV RNA forms that are believed to be generated from cccDNA of HBV:

TABLE 1

| HBV RNA forms believed to be generated from cccDNA of HBV Type/Description |
| --- |
| 3.5 kb pregenomic (pg)RNA, which is also the mRNA for core and polymerase proteins |
| 3.5 kb precore mRNA, which is longer than pgRNA at 5' end and produces HBeAg |
| 2.4 kb mRNA, large (preS1) surface proteins |
| 2.1 kb mRNA, two transcription start sites for middle (preS2) and small (HBs) surface proteins |
| 0.7 kb mRNA, HBx regulatory protein |
| Shorter X-gene transcripts (later transcription start sites/5' ends) |
| Truncated HBV mRNAs from a secondary 3' end site in the X gene (upstream of the primary polyA site) might be transcribed from cccDNA but may be predominantly not from cccDNA |
| Spliced mRNAs. Spliced pgRNA can produce encapsidated spliced DNA. Conserved major spliced forms; minor splice types may vary by genotype |
| Possibly two antisense RNA transcripts |
| Novel transcription start sites (TSS) or splice forms may be discovered |

Below, in Table 2, is a list of the forms of HBV RNA that cannot be transcribed from integrated copies (i.e., are exclusively cccDNA in origin).

TABLE 2

Forms of HBV RNA that cannot be transcribed from integrated copies (are exclusively cccDNA in origin)
Type/Description 3.5 kb pregenomic (pg)RNA, which is also the mRNA for core and polymerase proteins
3.5 kb precore mRNA, which is longer than pgRNA at 5' end and produces HBeAg Below, in Table 3, are some forms of HBV RNA that could be transcribed from integrated copies.

TABLE 3

Some forms of HBV RNA that could be transcribed from integrated copies.
Type/Description Shorter mRNAs (not pgRNA or precore mRNAs) - depending on the cut site in the genome of the integrated HBV copy, the integrated copy may or may not be capable of producing one or more of the shorter mRNAs (such as the 2.4 kb, 2.1 kb, 0.7 kb or other variants described)
Truncated HBV mRNAs from integrated HBV copies from a secondary 3' end site in the X gene (upstream of the primary polyA site) - the primary polyA site used in cccDNA may not be intact or used in integrated copies
Fusion RNA products of HBV and host sequences from integrated HBV copies (variable structures depending on integration site with the human genome and promoter availability - it is possible either the 5' end or 3' end of such a transcript may contain human sequence)

Markers for HBV include the detection of DNA, e antigen (from the precore mRNA), core antigen (or combinations of antigens including e and core), and s antigen, as well as the subject's/patient's production of antibodies for these antigens. Suppression of the s antigen is the marker for a functional cure. However, the s antigen can be produced by integrated, non-replicating copies of HBV and therefore quantitation of HBsAg levels are unlikely to accurately reflect the pool of transcriptionally active cccDNA. DNA titer is monitored as a sensitive test to detect HBV infection and the decline in HBV is an indicator of treatment response. However, the current nucleoside analog therapies for HBV (which suppress reverse transcription) do not affect the transcription of pgRNA or other mRNAs, only the generation of new rcDNA copies. The decrease in DNA titers in the patient's blood (plasma or serum sample types) do not always correspond with the decline of HBV RNA, which may lag or even temporarily increase as encapsidated pgRNA (and spliced RNA) can be secreted by infected cells retaining transcriptionally active cccDNA. Because of this, HBV RNA has been explored as a separate marker for monitoring HBV disease state and therapy effectiveness. Studies have shown that HBV RNA levels can be predictive of outcomes such as e-antigen loss, viral relapse, or "flare" events after the discontinuation of treatment, and the biomarker is potentially critical in timing the end of treatment for HBV patients.

Discrimination between HBV RNA structures and variants, and distinguishing RNA from the homologous DNA counterparts is important to understanding the disease state. The state-of-art assays target the poly-A tail with a two-stage (RT and PCR) RACE method (van Bommel, et al., Hepatology 61:66-76 (2015); Zhang, et al., Methods Mol Med 95:29-44 (2004); Kairat, et al., Intervirology 42:228-237 (1999), Schutz et al, Journal of Virological Methods, 86(2): 167-171 (2000). Additional assays target the region of the genome between the transcription start sites of the pre-core mRNA and the pgRNA, to distinguish these forms (Wang, et al., Journal of Hepatology 65:700-710 (2016). Similar targeting of the 5' end length differences of the mRNAs can also be used to discriminate between the pgRNA and the smaller viral mRNAs that produce the s antigen and X antigen (Butler E. K. et al., Hepatology. 2018 68(6):2106-2117). Other assays can target the spliced RNA (or DNA) variants (Bayliss, et al., J. Hepatol. 59:1022-1028 (2013); Preiss, et al., Hepatology 48:741-749 (2008). All assays, except some of the poly-A targeted RACE assays, require the use of a DNA-removal method (such as DNase treatment, or a sample preparation method that favors RNA or depletes DNA) for discrimination of HBV RNA from DNA, which limits the sensitivity of the assay and potential use in qPCR without a DNAse inactivation step or other cleanup steps, and which may leave residual DNA or have an effect on RNA amount or integrity due to the additional steps involved. The polyA targeted RACE assays and most others require manual sample preparation, which limits the throughput of tests that can be run in a day. Thus, the existing assays in the art simply are not sensitive enough. Thus, there is a need in the art for a method of detecting HBV RNA in a background of homologous DNA without requirement for manual sample preparation, and with the capability to omit DNAse treatment.

In the field of molecular diagnostics, the amplification and detection of nucleic acids is of considerable significance. Such methods can be employed to detect any number of microorganisms, such as viruses and bacteria. The most prominent and widely-used amplification technique is the Polymerase Chain Reaction (PCR). Other amplification techniques include Ligase Chain Reaction, Polymerase Ligase Chain Reaction, Gap-LCR, Repair Chain Reaction, 3 SR, NASBA, Strand Displacement Amplification (SDA), Transcription Mediated Amplification (TMA), and Qβ-amplification.

Automated systems for PCR-based analysis often make use of a real-time detection of product amplification during the PCR process in the same reaction vessel. Key to such methods is the use of modified oligonucleotides carrying reporter groups or labels.

HBV infection is widespread, with about a third of the world population infected at one point in their lives, including 343 million who have chronic infections. Over 750,000 people die of hepatitis B each year, with about 300,000 of those deaths attributed to liver cancer. Despite the widespread infectivity of HBV, many of those infected are unaware, as the infection is largely asymptomatic. Moreover, current diagnostic methods focus on detection of HBV antigen, antibodies to HBV antigens, or HBV DNA. Studies indicate that a decrease in HBV antigen or HBV DNA titers in blood do not always correspond to a decline in HBV RNA. As such, there is a need in the art for a quick, reliable, and sensitive method of detecting HBV RNA, for monitoring HBV disease state and therapeutic efficacy. This invention described here enables the detection of HBV RNA in a background of homologous DNA without the requirements for manual sample preparation or for DNAse treatment.

SUMMARY OF THE INVENTION

The instant patent application contains a Sequence Listing, which has been submitted electronically in ASCII format and is hereby incorporated by reference in its entirety. The ASCII copy, created Feb. 7, 2020, is named "35679-US1_SL," and is 101,760 bytes in size.

Certain embodiments in the present disclosure relate to methods for the rapid detection of the presence or absence of HBV RNA in a biological or non-biological sample, for monitoring HBV disease state and therapeutic efficacy, for example, detection of HBV by a polymerase chain reaction (PCR) in a single test tube. Embodiments include methods of detection of HBV comprising performing at least one cycling step, which may include an amplifying step and a hybridizing step. Furthermore, embodiments include oligonucleotides (including a reverse transcription primer (which can also be a PCR primer), blocking oligonucleotide, conventional primers and probes), and kits that are designed for the detection of HBV in a single tube.

The use of the competitive blocking oligonucleotide improves detection and quantitation of RNA in the presence of homologous DNA. In HBV patients the DNA-containing virus and RNA are both circulating in the bloodstream, and in untreated patients the DNA level is typically higher than the RNA level. Both forms would also be found together in other sample types. Conventional PCR techniques cannot distinguish the HBV RNA (pgRNA and other unspliced mRNAs) from the DNA because there is a common sequence (only a subset of HBV RNA forms are spliced). DNA removal techniques (for instance DNases, or other sample processing methods that may favor RNA or deplete DNA) may also impact the RNA titer, may not be completely effective, or have variable effectiveness, and have stability, contamination, or other disadvantages preventing their use in automated or high-throughput workflows.

The competitive blocking oligonucleotide of the present disclosure will hybridize to homologous HBV DNA, for example, the HBV DNA genome. The competitive blocking oligonucleotides of the present disclosure hybridizes or binds to HBV DNA that overlaps part or all of the HBV-binding section of the primer(s). By binding to the homologous HBV DNA, the competitive blocking oligonucleotide blocks the binding site on the HBV DNA, thereby preventing the primers of the present disclosure (which hybridize to HBV RNA) from hybridizing to the homologous HBV DNA. The effect of this is that any homologous HBV DNA will not be amplified (except when it is at a concentration in great excess of the HBV RNA in the sample), because the primers will not hybridize efficiently to the homologous HBV DNA due to the competition at the binding site with the stronger-binding blocking oligonucleotide. As such, the assay of the present disclosure, which selectively detects and amplifies HBV RNA, will not inadvertently detect and amplify contaminating and unwanted HBV DNA except when it is at a concentration in great excess of the HBV RNA. The competitive blocking oligonucleotide of the present disclosure is a single stranded and can be of a variety of lengths, ranging from 20 to 70 bases. For example, the competitive blocking oligonucleotides of the present disclosure range from 24 bases to 61 bases long (SEQ ID NOs: 1-15). The competitive blocking oligonucleotides of the present disclosure may contain modified bases to improve performance, such as clamps or stabilizing modifications (such as pdU and locked nucleic acid (LNA)). For example, such modified stabilizing bases may be included in order to increase the Tm and binding strength. Indeed, the competitive blocking oligonucleotides of the present disclosure (SEQ ID NOs:1-15) contain such modifications. Additionally, the competitive blocking oligonucleotides of the present disclosure may also contain modifications that prevent extension of the 3' ends. Non-extensible ends can be facilitated by a C3 spacer, phosphate, a dideoxy nucleotide, attaching the 3'-end of a second oligonucleotide to the 3-end of an oligonucleotide, and the like. Indeed, the competitive blocking oligonucleotides of the present disclosure (SEQ ID NOs:1-15) are modified by adding a non-extensible C3 spacer at the 3' end so as to prevent extension (see, FIG. 2). In this way, the competitive blocking oligonucleotides of the present disclosure can be in the presence of polymerase and the polymerase will only extend hybridized primers (e.g., the HBV RNA-specific primers). The use of competitive blocking oligonucleotides is an improvement over conventional DNA removal techniques. Moreover, the use of competitive blocking oligonucleotides effectively allows for an HBV RNA assay that is able to distinguish between HBV RNA and DNA.

One sequence difference between HBV DNA and RNA is the polyA tail of the pgRNA and other mRNAs; however, methods that use oligo d(T) primers can detect non-target RNAs or other sequences with polyA stretches. "Anchored" polyT-containing oligonucleotides can provide some measure of specificity against non-target binding and extension however this is a tradeoff strategy which will result in some binding to the HBV DNA. The method in this disclosure includes a competitive blocking oligonucleotide matching the DNA sequence at a target where the RNA sequence has a polyA tail junction, as a method for improving the performance (sensitivity and specificity) of an assay targeting RNA in the presence of DNA. The binding of the competitive blocking oligonucleotide to the homologous genomic HBV DNA prevents binding of the primer (e.g., RT primer), and therefore reduces the unwanted amplification of the homologous genomic HBV DNA. Modified stabilizing bases can be incorporated into the assay oligonucleotides or blocker oligonucleotides in order to further improve the discrimination capabilities of the method.

Primers and probes can be provided that target the polyA tail of HBV RNA (in particular, HBV RNA transcribed from cccDNA, which has a standard polyA tail position for transcripts, such as pgRNA but also including other mRNAs and spliced RNAs). Competitive blocking oligonucleotides can be provided that increase specificity for RNA in the presence of HBV DNA. Additional primers and probes can be provided for that target other polyA sites, such as the secondary or truncated polyA site for HBV transcripts that can originate from integrated HBV copies. Competitive blocking oligonucleotides can be provided that increase specificity for RNA with these specific polyA sites in the presence of the homologous DNA.

One embodiment of the disclosure is directed to a method for detecting one or more target nucleic acids of Hepatitis B Virus (HBV) RNA in a sample, the method comprising: (a) providing a sample; (b) performing an amplification step comprising contacting the sample with one or more competitive blocking oligonucleotides and one or more set of primers, wherein the one or more set of primers comprises at least one forward primer and at least one reverse transcription (RT) primer that also functions as a reverse primer, to produce an amplification product, if the one or more target nucleic acids of HBV RNA is present in the sample; (c) performing a hybridization step, comprising contacting the amplification product, if the one or more target nucleic acids of HBV RNA is present in the sample, with one or more probes; and (d) performing a detection step, comprising detecting the presence or absence of the amplification product, wherein the presence of the amplification product is indicative of the presence of the one or more target nucleic acids of HBV RNA in the sample, and wherein the absence of the amplification product is indicative of the absence of the one or more target nucleic acids of HBV RNA in the sample. In another embodiment, the one or more competitive blocking oligonucleotides hybridizes to any homologous HBV DNA that may be present in the sample, thereby preventing the binding of the one or more set of primers to any homologous HBV DNA that may be present in the sample. In another embodiment, the one or more target nucleic acids of HBV RNA is derived from covalently-closed circular double-stranded DNA (cccDNA). In another embodiment, the cccDNA is HBV pre-genomic RNA (pgRNA). In another embodiment, the one or more target nucleic acids of HBV RNA comprises a poly-A tail. In another embodiment, the at least one reverse transcription (RT) primer that also functions as a reverse primer comprises a poly-T section to bind to the poly-A tail of the one or more target nucleic acids of HBV RNA. In another embodiment, the sample is a biological sample. In another embodiment, the biological sample is plasma. In another embodiment, the biological sample is blood. In another embodiment, (i) the at least one forward primer comprises a nucleic acid sequence of SEQ ID NO:387, or a complement thereof; (ii) the at least one reverse transcription (RT) primer that also functions as a reverse primer comprises a nucleic acid sequence of one or more of a group selected from SEQ ID NOs:96, 116, 117, 151, and 152, or a complement thereof; (iii) the one or more probes comprises a nucleic acid sequence of SEQ ID NO:388, or a complement thereof; and (iv) the one or more competitive blocking oligonucleotides comprises a nucleic acid sequence of SEQ ID NO:11, or a complement thereof.

Another embodiment of the present disclosure is directed to a method for detecting one or more target nucleic acids of Hepatitis B Virus (HBV) RNA in a sample, the method comprising: (a) providing a sample; (b) performing an amplification step comprising contacting the sample with one or more competitive blocking oligonucleotides and one or more set of primers, wherein the one or more set of primers comprises at least one forward primer and at least one reverse transcription (RT) primer that also functions as a reverse primer, to produce an amplification product, if the one or more target nucleic acids of HBV RNA is present in the sample; (c) performing a hybridization step, comprising contacting the amplification product, if the one or more target nucleic acids of HBV RNA is present in the sample, with one or more probes; and (d) performing a detection step, comprising detecting the presence or absence of the amplification product, wherein the presence of the amplification product is indicative of the presence of the one or more target nucleic acids of HBV RNA in the sample, and wherein the absence of the amplification product is indicative of the absence of the one or more target nucleic acids of HBV RNA in the sample, and wherein: the one or more set of primers comprises at least one forward primer and at least one reverse transcription (RT) primer that also functions as a reverse primer, and wherein: (i) the at least one forward primer comprises a nucleic acid sequence of SEQ ID NO:387, or a complement thereof; (ii) the at least one reverse transcription (RT) primer that also functions as a reverse primer comprises a poly-T section, and comprises a nucleic acid sequence of one or more of a group selected from SEQ ID NOs:96, 116, 117, 151, and 152, or a complement thereof; (iii) the one or more probes comprises a nucleic acid sequence of SEQ ID NO:388, or a complement thereof; and (iv) the one or more competitive blocking oligonucleotides comprises a nucleic acid sequence of SEQ ID NO:11, or a complement thereof. In another embodiment, the one or more competitive blocking oligonucleotides hybridizes to any homologous HBV DNA that may be present in the sample, thereby preventing the binding of the one or more set of primers to any homologous HBV DNA that may be present in the sample. In another embodiment, the one or more target nucleic acids of HBV RNA is derived from covalently-closed circular double-stranded DNA (cccDNA). In another embodiment, the cccDNA is HBV pre-genomic RNA (pgRNA). In another embodiment, the one or more target nucleic acids of HBV RNA comprises a poly-A tail. In another embodiment, the at least one reverse transcription (RT) primer that also functions as a reverse primer comprises a poly-T section to bind to the poly-A tail of the one or more target nucleic acids of HBV RNA. In another embodiment, the sample is a biological sample. In another embodiment, the biological sample is plasma. In another embodiment, the biological sample is blood.

Another embodiment of the present disclosure is directed to a kit for detecting one or more target nucleic acids of Hepatitis B Virus (HBV) RNA that may be present in a sample, the kit comprising amplification reagents comprising: (a) a nucleic acid polymerase; (b) nucleotide monomers; (c) one or more set of primers, wherein the one or more set of primers comprises at least one forward primer and at least one reverse transcription (RT) primer that also functions as a reverse primer; and (d) one or more probes, and (e) one or more competitive blocking oligonucleotides. In another embodiment, the one or more competitive blocking oligonucleotides hybridizes to any homologous HBV DNA that may be present in the sample, thereby preventing the binding of the one or more set of primers to any homologous HBV DNA that may be present in the sample. In another embodiment, the one or more target nucleic acids of HBV RNA is derived from covalently-closed circular double-stranded DNA (cccDNA). In another embodiment, the cccDNA is HBV pre-genomic RNA (pgRNA). In another embodiment, the one or more target nucleic acids of HBV RNA comprises a poly-A tail. In another embodiment, the at least one reverse transcription (RT) primer that also functions as a reverse primer comprises a poly-T section to bind to the poly-A tail of the one or more target nucleic acids of HBV RNA. In another embodiment, the sample is a biological sample, such as plasma or blood. In another embodiment, (i) the at least one forward primer comprises a nucleic acid sequence of SEQ ID NO:387, or a complement thereof; (ii) the at least one reverse transcription (RT) primer that also functions as a reverse primer comprises a nucleic acid sequence of one or more of a group selected from SEQ ID NOs:96, 116, 117, 151, and 152, or a complement thereof; (iii) the one or more probes comprises a nucleic acid sequence of SEQ ID NO:388, or a complement thereof; and (iv) the one or more competitive blocking oligonucleotides comprises a nucleic acid sequence of SEQ ID NO:11, or a complement thereof.

Another embodiment of the disclosure is directed to a kit for detecting Hepatitis B Virus (HBV) RNA in a sample, the method comprising: (a) a nucleic acid polymerase; (b) nucleotide monomers; (c) one or more set of primers, wherein the one or more set of primers comprises at least one forward primer and at least one reverse transcription (RT) primer that also functions as a reverse primer; (d) one or more probes; and (e) one or more competitive blocking oligonucleotides; and wherein: (i) the at least one forward primer comprises a nucleic acid sequence of SEQ ID NO:387, or a complement thereof; (ii) the at least one reverse transcription (RT) primer that also functions as a reverse primer comprises a poly-T section, and wherein the at least one reverse transcription primer that also functions as a reverse primer comprises a nucleic acid sequence of one or more of a group selected from SEQ ID NOs:96, 116, 117, 151, and 152, or a complement thereof; (iii) the one or more probes comprises a nucleic acid sequence of SEQ ID NO:388, or a complement thereof; and (iv) the one or more competitive blocking oligonucleotides comprises a nucleic acid sequence of SEQ ID NO:11, or a complement thereof. In another embodiment, the one or more competitive blocking oligonucleotides hybridizes to any homologous HBV DNA that may be present in the sample, thereby preventing the binding of the one or more set of primers to any homologous HBV DNA that may be present in the sample. In another embodiment, the one or more target nucleic acids of HBV RNA is derived from covalently-closed circular double-stranded DNA (cccDNA). In another embodiment, the cccDNA is HBV pre-genomic RNA (pgRNA). In another embodiment, the one or more target nucleic acids of HBV RNA comprises a poly-A tail. In another embodiment, the at least one reverse transcription (RT) primer that also functions as a reverse primer comprises a poly-T section to bind to the poly-A tail of the one or more target nucleic acids of HBV RNA. In another embodiment, the sample is a biological sample. In another embodiment, the biological sample is plasma. In another embodiment, the biological sample is blood.

One embodiment of the present disclosure is directed to a method for detecting one or more target nucleic acids of Hepatitis B Virus (HBV) RNA in a sample, the method comprising: (a) providing a sample; (b) performing an amplification step comprising contacting the sample with one or more competitive blocking oligonucleotides and one or more set of primers, wherein the one or more set of primers comprises one or more forward primer and one or more reverse transcription (RT) primer that also functions as a reverse primer, to produce an amplification product, if the one or more target nucleic acids of HBV RNA is present in the sample; (c) performing a hybridization step, comprising contacting the amplification product, if the one or more target nucleic acids of HBV RNA is present in the sample, with one or more probes; and (d) performing a detection step, comprising detecting the presence or absence of the amplification product, wherein the presence of the amplification product is indicative of the presence of the one or more target nucleic acids of HBV RNA in the sample, and wherein the absence of the amplification product is indicative of the absence of the one or more target nucleic acids of HBV RNA in the sample. In another embodiment, the one or more competitive blocking oligonucleotides hybridizes to any homologous HBV DNA that may be present in the sample, thereby preventing the binding of the one or more set of primers to any homologous HBV DNA that may be present in the sample. In another embodiment, the one or more target nucleic acids of HBV RNA is derived from covalently-closed circular double-stranded DNA (cccDNA). In another embodiment, the cccDNA is HBV pre-genomic RNA (pgRNA). In another embodiment, the one or more target nucleic acids of HBV RNA comprises a poly-A tail. In another embodiment, the one or more reverse transcription (RT) primer that also functions as a reverse primer comprises a poly-T section to bind to the poly-A tail of the one or more target nucleic acids of HBV RNA. In another embodiment, the sample is a biological sample, such as plasma and/or blood. In another embodiment, (i) the one or more forward primer comprises a nucleic acid sequence of SEQ ID NO:387, or a complement thereof; (ii) the one or more reverse transcription (RT) primer that also functions as a reverse primer comprises one or more nucleic acid sequences of a group selected from SEQ ID NOs:34, 35, 43, 94, 96, 112, 116, 117, 119, 121, 123, 124, 141, 142, 151, 152, 153, 154, 155, 157, 161, 162, 163, 164, 165, 166, 167, 168, 169, 170, 171, 172, 173, 174, 175, 176, 177, 178, 179, 180, 181, 182, 183, 184, 185, 186, 187, 188, 189, and 190, or a complement thereof; (iii) the one or more probes comprises a nucleic acid sequence of SEQ ID NO:388, or a complement thereof; and (iv) the one or more competitive blocking oligonucleotides comprises a nucleic acid sequence of a group selected from SEQ ID NOs:1, 2, 3, 4, 5, 9, 10, 11, 14, and 15, or a complement thereof. In another embodiment, the one or more reverse transcription (RT) primer that also functions as a reverse comprises two nucleic sequences, wherein the two nucleic acid sequences comprise the nucleic acid sequences of SEQ ID NOs:151 and 152, or complements thereof; and the one or more competitive blocking oligonucleotides comprise one sequence comprising the nucleic acid sequence of SEQ ID NO:11, or a complement thereof. In another embodiment, the one or more reverse transcription (RT) primer that also functions as a reverse comprises the nucleic acid sequences of SEQ ID NO:96, or a complement thereof; and the one or more competitive blocking oligonucleotides comprise one sequence comprising the nucleic acid sequence of SEQ ID NO:11, or a complement thereof. In another embodiment, the one or more reverse transcription (RT) primer that also functions as a reverse comprises the nucleic acid sequences of SEQ ID NO:43, or a complement thereof; and the one or more competitive blocking oligonucleotides comprise one sequence comprising the nucleic acid sequence of SEQ ID NO:2, or a complement thereof. In another embodiment, the one or more reverse transcription (RT) primer that also functions as a reverse primer comprises one or more nucleic acid sequences of a group selected from SEQ ID NOs:96, 112, 116, and 117, or a complement thereof; and the one or more competitive blocking oligonucleotides comprise one sequence comprising the nucleic acid sequence of SEQ ID NO:2, or a complement thereof. In another embodiment, the one or more reverse transcription (RT) primer that also functions as a reverse primer comprises one or more nucleic acid sequences of a group selected from SEQ ID NOs:94, 96, 116, 117, 119, 121, 123, 124, 151, 153, 155, and 157, or a complement thereof; and the one or more competitive blocking oligonucleotides comprise one sequence comprising the nucleic acid sequence of SEQ ID NO:11, or a complement thereof. In another embodiment, the one or more reverse transcription (RT) primer that also functions as a reverse primer comprises one or more nucleic acid sequences of a group selected from SEQ ID NOs:142, 161, 162, 163, 164, 165, 166, 167, 168, 169, 171, 172, 173, 174, 175, 176, 177, 178, 179, 180, 181, 182, 183, 184, 185, 186, 187, 188, 189, and 190, or a complement thereof and the one or more competitive blocking oligonucleotides comprise one sequence comprising the nucleic acid sequence of SEQ ID NO:11, or a complement thereof. In another embodiment, the one or more reverse transcription (RT) primer that also functions as a reverse primer comprises one or more nucleic acid sequences of a group selected from SEQ ID NOs:141, 153, 157, 161, 163, 169, 171, 173, 175, 177, 179, 181, 183, 185, 188, and 190, or a complement thereof; and the one or more competitive blocking oligonucleotides comprise one sequence comprising the nucleic acid sequence of SEQ ID NO:11, or a complement thereof. In another embodiment, the one or more reverse transcription (RT) primer that also functions as a reverse comprises the nucleic acid sequence of SEQ ID NO:35, or a complement thereof; and the one or more competitive blocking oligonucleotides comprises one or more nucleic acid sequences of a group selected from SEQ ID NOs:1, 2, 3, 4, and 5, or a complement thereof. In another embodiment, the one or more reverse transcription (RT) primer that also functions as a reverse comprises the nucleic acid sequence of SEQ ID NO:34, or a complement thereof; and the one or more competitive blocking oligonucleotides comprises one or more nucleic acid sequences of a group selected from SEQ ID NOs:2, 9, 10, 11, and 14, or a complement thereof. In another embodiment, the one or more reverse transcription (RT) primer that also functions as a reverse comprises the nucleic acid sequence of SEQ ID NO:151, or a complement thereof; and the one or more competitive blocking oligonucleotides comprises one or more nucleic acid sequences of a group selected from SEQ ID NOs:2, 10, 11, and 15, or a complement thereof.

Another embodiment of the present disclosure is directed to a method for detecting one or more target nucleic acids of Hepatitis B Virus (HBV) RNA in a sample, the method comprising: (a) providing a sample; (b) performing an amplification step comprising contacting the sample with one or more competitive blocking oligonucleotides and one or more set of primers, wherein the one or more set of primers comprises one or more forward primer and one or more one reverse transcription (RT) primer that also functions as a reverse primer, to produce an amplification product, if the one or more target nucleic acids of HBV RNA is present in the sample; (c) performing a hybridization step, comprising contacting the amplification product, if the one or more target nucleic acids of HBV RNA is present in the sample, with one or more probes; and (d) performing a detection step, comprising detecting the presence or absence of the amplification product, wherein the presence of the amplification product is indicative of the presence of the one or more target nucleic acids of HBV RNA in the sample, and wherein the absence of the amplification product is indicative of the absence of the one or more target nucleic acids of HBV RNA in the sample, and wherein: the one or more set of primers comprises one or more one forward primer and one or more one reverse transcription (RT) primer that also functions as a reverse primer, and wherein: (i) the one or more one forward primer comprises a nucleic acid sequence of SEQ ID NO:387, or a complement thereof; (ii) the one or more one reverse transcription (RT) primer that also functions as a reverse primer comprises a poly-T section, and comprises one or more nucleic acid sequences of a group selected from SEQ ID NOs: 34, 35, 43, 94, 96, 112, 116, 117, 119, 121, 123, 124, 141, 142, 151, 152, 153, 154, 155, 157, 161, 162, 163, 164, 165, 166, 167, 168, 169, 170, 171, 172, 173, 174, 175, 176, 177, 178, 179, 180, 181, 182, 183, 184, 185, 186, 187, 188, 189, and 190, or a complement thereof; (iii) the one or more probes comprises a nucleic acid sequence of SEQ ID NO:388, or a complement thereof; and (iv) the one or more competitive blocking oligonucleotides comprises a nucleic acid of a group selected from SEQ ID NOs:1, 2, 3, 4, 5, 9, 10, 11, 14, and 15, or a complement thereof. In another embodiment, the one or more reverse transcription (RT) primer that also functions as a reverse comprises two nucleic sequences, wherein the two nucleic acid sequences comprise the nucleic acid sequences of SEQ ID NOs:151 and 152, or complements thereof; and the one or more competitive blocking oligonucleotides comprise one sequence comprising the nucleic acid sequence of SEQ ID NO:11, or a complement thereof. In another embodiment, the one or more reverse transcription (RT) primer that also functions as a reverse comprises the nucleic acid sequences of SEQ ID NO:96, or a complement thereof; and the one or more competitive blocking oligonucleotides comprises one sequence comprising the nucleic acid sequence of SEQ ID NO:11, or a complement thereof. In another embodiment, the one or more reverse transcription (RT) primer that also functions as a reverse comprises the nucleic acid sequences of SEQ ID NO:43, or a complement thereof; and the one or more competitive blocking oligonucleotides comprise one sequence comprising the nucleic acid sequence of SEQ ID NO:2, or a complement thereof. In another embodiment, the one or more reverse transcription (RT) primer that also functions as a reverse primer comprises one or more nucleic acid sequences of a group selected from SEQ ID NOs:96, 112, 116, and 117, or a complement thereof; and the one or more competitive blocking oligonucleotides comprise one sequence comprising the nucleic acid sequence of SEQ ID NO:2, or a complement thereof. In another embodiment, the one or more reverse transcription (RT) primer that also functions as a reverse primer comprises one or more nucleic acid sequences of a group selected from SEQ ID NOs:94, 96, 116, 117, 119, 121, 123, 124, 151, 153, 155, and 157, or a complement thereof; and the one or more competitive blocking oligonucleotides comprise one sequence comprising the nucleic acid sequence of SEQ ID NO:11, or a complement thereof. In another embodiment, the one or more reverse transcription (RT) primer that also functions as a reverse primer comprises one or more nucleic acid sequences of a group selected from SEQ ID NOs:142, 161, 162, 163, 164, 165, 166, 167, 168, 169, 171, 172, 173, 174, 175, 176, 177, 178, 179, 180, 181, 182, 183, 184, 185, 186, 187, 188, 189, and 190, or a complement thereof; and the one or more competitive blocking oligonucleotides comprise one sequence comprising the nucleic acid sequence of SEQ ID NO:11, or a complement thereof. In another embodiment, the one or more reverse transcription (RT) primer that also functions as a reverse primer comprises one or more nucleic acid sequences of a group selected from SEQ ID NOs:141, 153, 157, 161, 163, 169, 171, 173, 175, 177, 179, 181, 183, 185, 188, and 190, or a complement thereof; and the one or more competitive blocking oligonucleotides comprise one sequence comprising the nucleic acid sequence of SEQ ID NO:11, or a complement thereof. In another embodiment, the one or more reverse transcription (RT) primer that also functions as a reverse comprises the nucleic acid sequence of SEQ ID NO:35, or a complement thereof; and the one or more competitive blocking oligonucleotides comprises one or more nucleic acid sequences of a group selected from SEQ ID NOs:1, 2, 3, 4, and 5, or a complement thereof. In another embodiment, the one or more reverse transcription (RT) primer that also functions as a reverse comprises the nucleic acid sequence of SEQ ID NO:34, or a complement thereof; and the one or more competitive blocking oligonucleotides comprises one or more nucleic acid sequences of a group selected from SEQ ID NOs:2, 9, 10, 11, and 14, or a complement thereof. In another embodiment, the one or more reverse transcription (RT) primer that also functions as a reverse comprises the nucleic acid sequence of SEQ ID NO:151, or a complement thereof; and the one or more competitive blocking oligonucleotides comprises one or more nucleic acid sequences of a group selected from SEQ ID NOs:2, 10, 11, and 15, or a complement thereof. In another embodiment, the one or more competitive blocking oligonucleotides hybridizes to any homologous HBV DNA that may be present in the sample, thereby preventing the binding of the one or more set of primers to any homologous HBV DNA that may be present in the sample. In another embodiment, the one or more target nucleic acids of HBV RNA is derived from covalently-closed circular double-stranded DNA (cccDNA). In another embodiment, the cccDNA is HBV pre-genomic RNA (pgRNA). In another embodiment, the one or more target nucleic acids of HBV RNA comprises a poly-A tail. In another embodiment, the one or more reverse transcription (RT) primer that also functions as a reverse primer comprises a poly-T section to bind to the poly-A tail of the one or more target nucleic acids of HBV RNA. In another embodiment, the sample is a biological sample. In another embodiment, the biological sample is plasma. In another embodiment, the biological sample is blood.

Another embodiment of the present disclosure is directed to a kit for detecting one or more target nucleic acids of Hepatitis B Virus (HBV) RNA that may be present in a sample, the kit comprising amplification reagents comprising: (a) a nucleic acid polymerase; (b) nucleotide monomers; (c) one or more set of primers, wherein the one or more set of primers comprises one or more forward primer and one or more reverse transcription (RT) primer that also functions as a reverse primer; and (d) one or more probes, and (e) one or more competitive blocking oligonucleotides. In another embodiment, the one or more competitive blocking oligonucleotides hybridizes to any homologous HBV DNA that may be present in the sample, thereby preventing the binding of the one or more set of primers to any homologous HBV DNA that may be present in the sample. In another embodiment, the one or more target nucleic acids of HBV RNA is derived from covalently-closed circular double-stranded DNA (cccDNA). In another embodiment, the cccDNA is HBV pre-genomic RNA (pgRNA). In another embodiment, the one or more target nucleic acids of HBV RNA comprises a poly-A tail. In another embodiment, the one or more reverse transcription (RT) primer that also functions as a reverse primer comprises a poly-T section to bind to the poly-A tail of the one or more target nucleic acids of HBV RNA. In another embodiment, the sample is a biological sample. In another embodiment, the biological sample is plasma. In another embodiment, the biological sample is blood. In another embodiment, (i) the one or more forward primer comprises a nucleic acid sequence of SEQ ID NO:387, or a complement thereof (ii) the one or more reverse transcription (RT) primer that also functions as a reverse primer comprises one or more nucleic acid sequences of a group selected from SEQ ID NOs: 34, 35, 43, 94, 96, 112, 116, 117, 119, 121, 123, 124, 141, 142, 151, 152, 153, 154, 155, 157, 161, 162, 163, 164, 165, 166, 167, 168, 169, 170, 171, 172, 173, 174, 175, 176, 177, 178, 179, 180, 181, 182, 183, 184, 185, 186, 187, 188, 189, and 190, or a complement thereof; (iii) the one or more probes comprises a nucleic acid sequence of SEQ ID NO:388, or a complement thereof and (iv) the one or more competitive blocking oligonucleotides comprises a nucleic acid of a group selected from SEQ ID NOs:1, 2, 3, 4, 5, 9, 10, 11, 14, and 15, or a complement thereof. In another embodiment, the one or more reverse transcription (RT) primer that also functions as a reverse comprises two nucleic sequences, wherein the two nucleic acid sequences comprise the nucleic acid sequences of SEQ ID NOs:151 and 152, or complements thereof; and the one or more competitive blocking oligonucleotides comprise one sequence comprising the nucleic acid sequence of SEQ ID NO:11, or a complement thereof. In another embodiment, the one or more reverse transcription (RT) primer that also functions as a reverse comprises the nucleic acid sequences of SEQ ID NO:96, or a complement thereof; and the one or more competitive blocking oligonucleotides comprise one sequence comprising the nucleic acid sequence of SEQ ID NO:11, or a complement thereof. In another embodiment, the one or more reverse transcription (RT) primer that also functions as a reverse comprises the nucleic acid sequences of SEQ ID NO:43, or a complement thereof; and the one or more competitive blocking oligonucleotides comprise one sequence comprising the nucleic acid sequence of SEQ ID NO:2, or a complement thereof. In another embodiment, the one or more reverse transcription (RT) primer that also functions as a reverse primer comprises one or more nucleic acid sequences of a group selected from SEQ ID NOs:96, 112, 116, and 117, or a complement thereof; and the one or more competitive blocking oligonucleotides comprise one sequence comprising the nucleic acid sequence of SEQ ID NO:2, or a complement thereof. In another embodiment, the one or more reverse transcription (RT) primer that also functions as a reverse primer comprises one or more nucleic acid sequences of a group selected from SEQ ID NOs:94, 96, 116, 117, 119, 121, 123, 124, 151, 153, 155, and 157, or a complement thereof; and the one or more competitive blocking oligonucleotides comprise one sequence comprising the nucleic acid sequence of SEQ ID NO:11, or a complement thereof. In another embodiment, the one or more reverse transcription (RT) primer that also functions as a reverse primer comprises one or more nucleic acid sequences of a group selected from SEQ ID NOs:142, 161, 162, 163, 164, 165, 166, 167, 168, 169, 171, 172, 173, 174, 175, 176, 177, 178, 179, 180, 181, 182, 183, 184, 185, 186, 187, 188, 189, and 190, or a complement thereof; and the one or more competitive blocking oligonucleotides comprise one sequence comprising the nucleic acid sequence of SEQ ID NO:11, or a complement thereof. In another embodiment, the one or more reverse transcription (RT) primer that also functions as a reverse primer comprises one or more nucleic acid sequences of a group selected from SEQ ID NOs:141, 153, 157, 161, 163, 169, 171, 173, 175, 177, 179, 181, 183, 185, 188, and 190, or a complement thereof; and the one or more competitive blocking oligonucleotides comprise one sequence comprising the nucleic acid sequence of SEQ ID NO:11, or a complement thereof. In another embodiment, the one or more reverse transcription (RT) primer that also functions as a reverse comprises the nucleic acid sequence of SEQ ID NO:35, or a complement thereof; and the one or more competitive blocking oligonucleotides comprises one or more nucleic acid sequences of a group selected from SEQ ID NOs:1, 2, 3, 4, and 5, or a complement thereof. In another embodiment, the one or more reverse transcription (RT) primer that also functions as a reverse comprises the nucleic acid sequence of SEQ ID NO:34, or a complement thereof; and the one or more competitive blocking oligonucleotides comprises one or more nucleic acid sequences of a group selected from SEQ ID NOs:2, 9, 10, 11, and 14, or a complement thereof. In another embodiment, the one or more reverse transcription (RT) primer that also functions as a reverse comprises the nucleic acid sequence of SEQ ID NO:151, or a complement thereof; and the one or more competitive blocking oligonucleotides comprises one or more nucleic acid sequences of a group selected from SEQ ID NOs:2, 10, 11, and 15, or a complement thereof Another embodiment of the present disclosure is directed to a kit for detecting Hepatitis B Virus (HBV) RNA in a sample, the method comprising: (a) a nucleic acid polymerase; (b) nucleotide monomers; (c) one or more set of primers, wherein the one or more set of primers comprises one or more forward primer and one or more reverse transcription (RT) primer that also functions as a reverse primer; (d) one or more probes; and (e) one or more competitive blocking oligonucleotides; and wherein: (i) the one or more forward primer comprises a nucleic acid sequence of SEQ ID NO:387, or a complement thereof; (ii)

the one or more reverse transcription (RT) primer that also functions as a reverse primer comprises a poly-T section, and wherein the one or more reverse transcription primer that also functions as a reverse primer comprises one or more nucleic acid sequences of a group selected from SEQ ID NOs: 34, 35, 43, 94, 96, 112, 116, 117, 119, 121, 123, 124, 141, 142, 151, 152, 153, 154, 155, 157, 161, 162, 163, 164, 165, 166, 167, 168, 169, 170, 171, 172, 173, 174, 175, 176, 177, 178, 179, 180, 181, 182, 183, 184, 185, 186, 187, 188, 189, and 190, or a complement thereof; (iii) the one or more probes comprises a nucleic acid sequence of SEQ ID NO:388, or a complement thereof; and (iv) the one or more competitive blocking oligonucleotides comprises a nucleic acid of a group selected from SEQ ID NOs:1, 2, 3, 4, 5, 9, 10, 11, 14, and 15, or a complement thereof. In another embodiment, the one or more reverse transcription (RT) primer that also functions as a reverse comprises two nucleic sequences, wherein the two nucleic acid sequences comprise the nucleic acid sequences of SEQ ID NOs:151 and 152, or complements thereof; and the one or more competitive blocking oligonucleotides comprise one sequence comprising the nucleic acid sequence of SEQ ID NO:11, or a complement thereof. In another embodiment, the one or more reverse transcription (RT) primer that also functions as a reverse comprises the nucleic acid sequences of SEQ ID NO:96, or a complement thereof; and the one or more competitive blocking oligonucleotides comprise one sequence comprising the nucleic acid sequence of SEQ ID NO:11, or a complement thereof. In another embodiment, the one or more reverse transcription (RT) primer that also functions as a reverse comprises the nucleic acid sequences of SEQ ID NO:43, or a complement thereof; and the one or more competitive blocking oligonucleotides comprise one sequence comprising the nucleic acid sequence of SEQ ID NO:2, or a complement thereof. In another embodiment, the one or more reverse transcription (RT) primer that also functions as a reverse primer comprises one or more nucleic acid sequences of a group selected from of SEQ ID NOs:96, 112, 116, and 117, or a complement thereof; and the one or more competitive blocking oligonucleotides comprise one sequence comprising the nucleic acid sequence of SEQ ID NO:2, or a complement thereof. In another embodiment, the one or more reverse transcription (RT) primer that also functions as a reverse primer comprises one or more nucleic acid sequences of a group selected from SEQ ID NOs:94, 96, 116, 117, 119, 121, 123, 124, 151, 153, 155, and 157, or a complement thereof; and the one or more competitive blocking oligonucleotides comprise one sequence comprising the nucleic acid sequence of SEQ ID NO:11, or a complement thereof. In another embodiment, the one or more reverse transcription (RT) primer that also functions as a reverse primer comprises one or more nucleic acid sequences of a group selected from SEQ ID NOs:142, 161, 162, 163, 164, 165, 166, 167, 168, 169, 171, 172, 173, 174, 175, 176, 177, 178, 179, 180, 181, 182, 183, 184, 185, 186, 187, 188, 189, and 190, or a complement thereof and the one or more competitive blocking oligonucleotides comprise one sequence comprising the nucleic acid sequence of SEQ ID NO:11, or a complement thereof. In another embodiment, the one or more reverse transcription (RT) primer that also functions as a reverse primer comprises one or more nucleic acid sequences of a group selected from SEQ ID NOs:141, 153, 157, 161, 163, 169, 171, 173, 175, 177, 179, 181, 183, 185, 188, and 190, or a complement thereof; and the one or more competitive blocking oligonucleotides comprise one sequence comprising the nucleic acid sequence of SEQ ID NO:11, or a complement thereof. In another embodiment, the one or more reverse transcription (RT) primer that also functions as a reverse comprises the nucleic acid sequence of SEQ ID NO:35, or a complement thereof; and the one or more competitive blocking oligonucleotides comprises one or more nucleic acid sequences of a group selected from SEQ ID NOs:1, 2, 3, 4, and 5, or a complement thereof. In another embodiment, the one or more reverse transcription (RT) primer that also functions as a reverse comprises the nucleic acid sequence of SEQ ID NO:34, or a complement thereof; and the one or more competitive blocking oligonucleotides comprises one or more nucleic acid sequences of a group selected from SEQ ID NOs:2, 9, 10, 11, and 14, or a complement thereof. In another embodiment, the one or more reverse transcription (RT) primer that also functions as a reverse comprises the nucleic acid sequence of SEQ ID NO:151, or a complement thereof; and the one or more competitive blocking oligonucleotides comprises one or more nucleic acid sequences of a group selected from SEQ ID NOs:2, 10, 11, and 15, or a complement thereof. In another embodiment, the one or more competitive blocking oligonucleotides hybridizes to any homologous HBV DNA that may be present in the sample, thereby preventing the binding of the one or more set of primers to any homologous HBV DNA that may be present in the sample. In another embodiment, the one or more target nucleic acids of HBV RNA is derived from covalently-closed circular double-stranded DNA (cccDNA). In another embodiment, the cccDNA is HBV pre-genomic RNA (pgRNA). In another embodiment, the one or more target nucleic acids of HBV RNA comprises a poly-A tail. In another embodiment, the one or more reverse transcription (RT) primer that also functions as a reverse primer comprises a poly-T section to bind to the poly-A tail of the one or more target nucleic acids of HBV RNA. In another embodiment, the sample is a biological sample, such as plasma and/or blood.

Other embodiments provide an oligonucleotide comprising or consisting of a sequence of nucleotides selected from SEQ ID NOs:1-400, or complements thereof, which oligonucleotide has 100 or fewer nucleotides. In another embodiment, the present disclosure provides an oligonucleotide that includes a nucleic acid having at least 70% sequence identity (e.g., at least 75%, 80%, 85%, 90% or 95%, etc.) to one of SEQ ID NOs:1-400, or complements thereof, which oligonucleotide has 100 or fewer nucleotides. Generally, these oligonucleotides may be primer nucleic acids, RT primer nucleic acids, competitive blocking nucleic acids, probe nucleic acids, or the like in these embodiments. In certain of these embodiments, the oligonucleotides have 40 or fewer nucleotides (e.g., 35 or fewer nucleotides, 30 or fewer nucleotides, 25 or fewer nucleotides, 20 or fewer nucleotides, 15 or fewer nucleotides, etc.) In some embodiments, the oligonucleotides comprise at least one modified nucleotide, e.g., to alter nucleic acid hybridization stability relative to unmodified nucleotides. Optionally, the oligonucleotides comprise at least one label and optionally at least one quencher moiety. In some embodiments, the oligonucleotides include at least one conservatively modified variation. "Conservatively modified variations" or, simply, "conservative variations" of a particular nucleic acid sequence refers to those nucleic acids, which encode identical or essentially identical amino acid sequences, or, where the nucleic acid does not encode an amino acid sequence, to essentially identical sequences, or which contain identical or essentially identical nucleic acid sequences that may serve the same function and/or may have additional functionalities, such as hybridizing to slightly modified targets (i.e. target genetic diversity). One of skill in the art will recognize that individual substitutions, deletions or additions which alter, add or delete a single nucleotide or a small percentage of nucleotides (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid.

In one aspect, amplification can employ a polymerase enzyme having 5' to 3' nuclease activity. Thus, the donor fluorescent moiety and the acceptor moiety, e.g., a quencher, may be within no more than 5 to 20 nucleotides (e.g., within 8 or 10 nucleotides) of each other along the length of the probe. In another aspect, the probe includes a nucleic acid sequence that permits secondary structure formation. Such secondary structure formation may result in spatial proximity between the first and second fluorescent moiety. According to this method, the second fluorescent moiety on the probe can be a quencher.

The present disclosure also provides for methods of detecting the presence or absence of HBV nucleic acid, in particular HBV RNA, in a biological sample from an individual. These methods can be employed to detect the presence or absence of HBV RNA (in particular, HBV RNA transcribed from cccDNA, such as pgRNA) in plasma, for use in blood screening and diagnostic testing. Additionally, the same test may be used by someone experienced in the art to assess urine and other sample types to detect and/or quantitate HBV or HBV RNA (in particular, HBV RNA transcribed from cccDNA, such as pgRNA). Such sample types can include any such sample, where HBV nucleic acids, such as HBV RNA, may be found, including whole blood, serum, biopsy samples, cell cultures, hepatocytes, etc. Also, such methods generally include performing at least one cycling step, which includes an amplifying step and a dye-binding step. Typically, the amplifying step includes contacting the sample with one or more pairs of oligonucleotide primers to produce one or more amplification products if a nucleic acid molecule is present in the sample, and the dye-binding step includes contacting the amplification product with a double-stranded DNA binding dye. Such methods also include detecting the presence or absence of binding of the double-stranded DNA binding dye into the amplification product, wherein the presence of binding is indicative of the presence of HBV or HBV RNA (in particular, HBV RNA transcribed from cccDNA, such as pgRNA) in the sample, and wherein the absence of binding is indicative of the absence of HBV or HBV RNA (in particular, HBV RNA transcribed from cccDNA, such as pgRNA) in the sample. A representative double-stranded DNA binding dye is ethidium bromide. Other nucleic acid-binding dyes include DAPI, Hoechst dyes, PicoGreen®, RiboGreen®, OliGreen®, and cyanine dyes such as YO-YO® and SYBR® Green. In addition, such methods also can include determining the melting temperature between the amplification product and the double-stranded DNA binding dye, wherein the melting temperature confirms the presence or absence of HBV or HBV RNA (in particular, HBV RNA transcribed from cccDNA, such as pgRNA).

In a further embodiment, a kit for detecting and/or quantitating one or more nucleic acids of HBV, including HBV RNA (in particular, HBV RNA transcribed from cccDNA, such as pgRNA). The kit can include one or more primers or sets of primers specific for amplification of the gene target; one or more competitive blocking oligonucleotides, and one or more detectable oligonucleotide probes specific for detection of the amplification products. The primers, probes, or blocking oligonucleotides may contain modified bases to improve performance, for instance clamps or stabilizing modifications (such as pdU and locked nucleic acid (LNA)) or modifications that prevent extension of the 3' ends of probes and blocking oligonucleotides.

In one aspect, the kit can include probes already labeled with donor and corresponding acceptor moieties, e.g., another fluorescent moiety or a dark quencher, or can include fluorophoric moieties for labeling the probes. The kit can also include nucleoside triphosphates, nucleic acid polymerase, and buffers necessary for the function of the nucleic acid polymerase. The kit can also include a package insert and instructions for using the primers, probes, and fluorophoric moieties to detect the presence or absence of HBV or HBV RNA (in particular, HBV pgRNA) in a sample.

Unless otherwise defined, all technical and scientific terms used herein have the same meaning as commonly understood by one of ordinary skill in the art to which this invention belongs. Although methods and materials similar or equivalent to those described herein can be used in the practice or testing of the present subject matter, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2 shows the HBV poly-A target assay design, depicting the RT oligonucleotide, which can also act as a reverse primer and which has a poly-T section (shown as SEQ ID NO: 403) to bind to the poly-A tail of the target HBV pgRNA, at the polyadenylation site (SEQ ID NO: 402), along with a competitive blocking oligonucleotide. Corresponding HBV DNA at the polyadenylation site (SEQ ID NO: 401) is shown on the top.

FIG. 7 shows real time PCR growth curves of an HBV RNA poly-A target assay with: (top row) 100/copies mL RNA target in serum, showing amplicon production in the presence of an RT primer without any blocker, and no change in the presence of an RT primer and a competitive blocking oligonucleotide. (bottom row) no RNA target but in the presence of 100,000 IU/mL of HBV DNA in serum, showing low-signal amplicon production (off-target DNA amplification) in the presence of an RT primer without any blocker, and no amplicon production in the presence of an RT primer and a competitive blocking oligonucleotide.

FIG. 9 shows CT values of an HBV RNA poly-A target assay with a competitive blocking oligonucleotide, showing tolerance of high HBV DNA input under conditions of mixed DNA+RNA samples. Without DNA added, the assay shows linearity from $1 \times 10^9$ to 10 copies/mL HBV RNA. With DNA added at the high level of $1 \times 10^9$ IU/mL, the RNA assay is unaffected except at 100 and 10 copies/mL RNA.

DETAILED DESCRIPTION OF THE INVENTION

Figure 1:
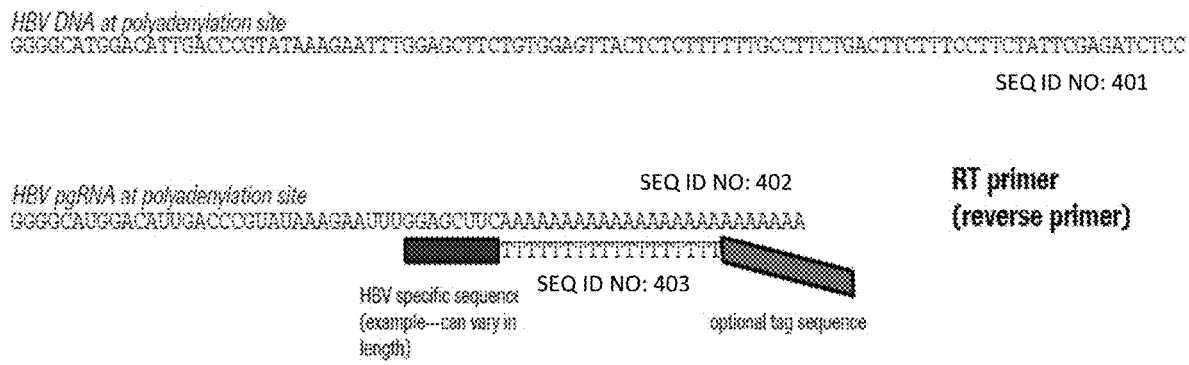
FIG. 1 shows the HBV poly-A target assay design, depicting the RT oligonucleotide, which can also act as a reverse primer and which has a poly-T section (shown as SEQ ID NO: 403) to bind to the poly-A tail of the target HBV pgRNA at the polyadenylation site (SEQ ID NO: 402), without a competitive blocking oligonucleotide. Corresponding HBV DNA at the polyadenylation site (SEQ ID NO: 401) is shown on the top.

Diagnosis of HBV infection by nucleic acid amplification provides a method for rapidly, accurately, reliably, specifically, and sensitively detecting and/or quantitating the viral infection. A real-time PCR assay for detecting HBV RNA (in particular, HBV RNA transcribed from cccDNA, such as pgRNA) in the presence of homologous HBV DNA in a non-biological or biological samples is described herein. Primers (including RT primers), competitive blocking oligonucleotides, and probes for detecting and/or quantitating HBV are provided, as are articles of manufacture or kits containing such primers, competitive blocking oligonucleotides, and probes. The increased specificity and sensitivity of real-time PCR for detection of HBV RNA (in particular, HBV RNA transcribed from cccDNA, such as pgRNA) compared to other methods, as well as the improved features of real-time PCR including sample containment and real-time detection and quantitating of the amplified product, make feasible the implementation of this technology for routine diagnosis of HBV infections and therapeutic efficacy, in the clinical laboratory. Moreover, this real-time PCR assay for detection of HBV RNA (in particular, HBV RNA transcribed from cccDNA, such as pgRNA) may provide important information regarding patient status (e.g., functional cure, sterilizing cure, and/or partial cure). As an example, a patient may have DNA viral titer depleted by a nucleoside analog treatment but retain high circulating HBV RNA levels indicative of continued presence and transcriptional activity of cccDNA in the infected liver cells, so that removal of treatment would cause a rebound in HBV. An another example, a patient on treatment may have both DNA and RNA markers suppressed, an indication that cccDNA has been depleted in the liver, however still have HbsAg produced from cells with integrated copies of HBV, which however cannot produce pgRNA and replicating virus.

Additionally, this technology may be employed for blood screening as well as for prognosis. This HBV RNA detection assay may also be multiplexed with other assays for the detection of other nucleic acids, e.g., other viruses, including, but not limited to, HIV, HCV and other hepatitis viruses, such as HAV, HEV, and/or HDV, in parallel.

The present disclosure includes oligonucleotide primers (including RT primers), competitive blocking oligonucleotides, and fluorescent labeled hydrolysis probes that hybridize to the HBV nucleic acids, in particular HBV RNA (in particular, HBV RNA transcribed from cccDNA, such as pgRNA), in order to specifically identify HBV RNA using, e.g., TaqMan® amplification and detection technology.

The disclosed methods may include performing at least one cycling step that includes amplifying one or more portions of the nucleic acid molecule gene target from a sample using one or more pairs of primers. "HBV primer(s)" or "HBV RT primer(s)" as used herein refer to oligonucleotide primers that specifically anneal to nucleic acid sequences found in HBV or HBV RNA (such as HBV pgRNA), and initiate reverse transcription and/or DNA synthesis therefrom under appropriate conditions producing the respective amplification products. An example of a nucleic acid sequences found in HBV that is suitable for targeting include HBV pgRNA. Each of the discussed HBV primers (including RT primers) anneals to a target such that at least a portion of each amplification product contains nucleic acid sequence corresponding to the target. The one or more amplification products are produced provided that one or more nucleic acid is present in the sample, thus the presence of the one or more amplification products is indicative of the presence of HBV and/or HBV RNA (in particular, HBV RNA transcribed from cccDNA, such as pgRNA) in the sample. The amplification product should contain the nucleic acid sequences that are complementary to one or more detectable probes for HBV and/or HBV RNA (in particular, HBV RNA transcribed from cccDNA, such as pgRNA). "HBV probe(s)" as used herein refer to oligonucleotide probes that specifically anneal to nucleic acid sequences found in the HBV target nucleic acid (e.g., HBV RNA, or HBV pgRNA). Each cycling step includes an amplification step, a hybridization step, and a detection step, in which the sample is contacted with the one or more detectable HBV or HBV RNA (in particular, HBV RNA transcribed from cccDNA, such as pgRNA) probes for detection of the presence or absence of HBV and/or HBV RNA (in particular, HBV RNA transcribed from cccDNA, such as pgRNA) in the sample. The term "blocking oligonucleotide" (or "competitive blocking oligonucleotide", or "blocker") as used herein refer to non-extensible oligonucleotides that specifically anneal to complement DNA and inhibit reverse transcription and DNA polymerization. In the presence of a blocking oligonucleotide any HBV DNA that may be present in the sample will hybridize to the blocking oligonucleotide, thereby rendering the HBV DNA unable to bind to primers targeting the polyA junction of HBV RNA, which may include short sequences matching both HBV DNA and HBV RNA. Thus, the blocking oligonucleotide prevents primer binding to homologous HBV DNA that might be in the sample.

As used herein, the term "amplifying" refers to the process of synthesizing nucleic acid molecules that are complementary to one or both strands of a template nucleic acid molecule (e.g., nucleic acid molecules from the HBV and/or HBV RNA (in particular, HBV RNA transcribed from cccDNA, such as pgRNA)). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

The term "primer" as used herein is known to those skilled in the art and refers to oligomeric compounds, primarily to oligonucleotides but also to modified oligonucleotides that are able to "prime" DNA synthesis by a template-dependent DNA polymerase, i.e., the 3'-end of the oligonucleotide provides a free 3'-OH group where further "nucleotides" may be attached by a template-dependent DNA polymerase establishing 3' to 5' phosphodiester linkage whereby deoxynucleoside triphosphates are used and whereby pyrophosphate is released. In some embodiments, the primer is also a reverse transcription (RT) primer (RT primer). There are several types of RT primers known in the art, including oligo(dT)N primers, anchored oligo(dT)N primers, random hexamer primers, and sequence specific primers. In some embodiments, the RT primer will anneal to RNA (e.g., HBV RNA, in particular, HBV RNA transcribed from cccDNA, such as pgRNA), and extend to generate a DNA complement (i.e., reverse transcription of the target). In some embodiments, the RT primer targets poly-A-containing HBV RNA, and therefore the RT primer is a poly-T containing oligonucleotide.

The term "hybridizing" refers to the annealing of one or more probes to an amplification product. "Hybridization conditions" typically include a temperature that is below the melting temperature of the probes but that avoids non-specific hybridization of the probes.

The term "5' to 3' nuclease activity" refers to an activity of a nucleic acid polymerase, typically associated with the nucleic acid strand synthesis, whereby nucleotides are removed from the 5' end of nucleic acid strand.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus,* and *Methanothermus fervidus*. Nonetheless, polymerases that are not thermostable also can be employed in PCR assays provided the enzyme is replenished, if necessary.

The term "complement thereof" refers to nucleic acid that is both the same length as, and exactly complementary to, a given nucleic acid.

The term "extension" or "elongation" when used with respect to nucleic acids refers to when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

The terms "identical" or percent "identity" in the context of two or more nucleic acid sequences, refer to two or more sequences or subsequences that are the same or have a specified percentage of nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-410, Gish et al. (1993) "Identification of protein coding regions by database similarity search" *Nature Genet.* 3:266-272, Madden et al. (1996) "Applications of network BLAST server" *Meth. Enzymol.* 266:131-141, Altschul et al. (1997) "Gapped BLAST and PSI-BLAST: a new generation of protein database search programs" *Nucleic Acids Res.* 25:3389-3402, and Zhang et al. (1997) "PowerBLAST: A new network BLAST application for interactive or automated sequence analysis and annotation" *Genome Res.* 7:649-656, which are each incorporated herein by reference.

A "modified nucleotide" in the context of an oligonucleotide refers to an alteration in which at least one nucleotide of the oligonucleotide sequence is replaced by a different nucleotide that provides a desired property to the oligonucleotide. Exemplary modified nucleotides that can be substituted in the oligonucleotides described herein include, e.g., a t-butyl benzyl, a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-O-methyl ribo-U, 2'-O-methyl ribo-C, an N4-ethyl-dC, an N6-methyl-dA, an N6-benzyl-dA, a 5-propynyl dU, a 5-propynyl dC, and the like. Another example of a modified nucleotide includes locked nucleic acid (LNA). An LNA (also known as inaccessible RNA) is a modified RNA nucleotide in which the ribose moiety is modified with an extra bridge connecting the 2' oxygen and the 4' carbon. This bridge locks the ribose in the 3'-endo (North) confirmation, which is often found in the A-form duplexes. The effect of LNA is that the locked ribose conformation enhances base stacking and backbone pre-organization, which significantly increases the hybridization properties (melting temperature) of oligonucleotides. Many other modified nucleotides that can be substituted in the oligonucleotides are referred to herein or are otherwise known in the art. In certain embodiments, modified nucleotide substitutions modify melting temperatures ($T_m$) of the oligonucleotides relative to the melting temperatures of corresponding unmodified oligonucleotides. To further illustrate, certain modified nucleotide substitutions can reduce non-specific nucleic acid amplification (e.g., minimize primer dimer formation or the like), increase the yield of an intended target amplicon, and/or the like in some embodiments. Examples of these types of nucleic acid modifications are described in, e.g., U.S. Pat. No. 6,001,611, which is incorporated herein by reference. Other modified nucleotide substitutions may alter the stability of the oligonucleotide, or provide other desirable features. For instance, some modifications can make an oligonucleotide non-extensible, which is useful for probes and for the competitive blocking oligonucleotides. Non-extensible ends can be facilitated by, in addition to a phosphate, a C3 spacer, a dideoxy nucleotide, attaching the 3'-end of a second oligonucleotide to the 3-end of an oligonucleotide, and the like.

Detection of HBV Target Nucleic Acid

The present disclosure provides methods to detect HBV RNA (in particular, HBV RNA transcribed from cccDNA, such as pgRNA) by amplifying, for example, a portion of the HBV nucleic acid sequence that is adjacent to a poly-A tail (e.g., HBV RNA transcribed from cccDNA, such as pgRNA). Specifically, primers, competitive blocking oligonucleotides, and probes used to amplify and detect HBV nucleic acid molecule targets are provided by the embodiments in the present disclosure.

For detection of HBV RNA (in particular, HBV RNA transcribed from cccDNA, for example pgRNA), primers, competitive blocking oligonucleotides, and probes to amplify HBV target nucleic acid, such as HBV RNA (in particular, HBV RNA transcribed from cccDNA, such as pgRNA) are provided. HBV nucleic acids other than those exemplified herein can also be used to detect HBV RNA (in particular, HBV RNA transcribed from cccDNA, such as pgRNA) in a sample. For example, functional variants can be evaluated for specificity and/or sensitivity by those of skill in the art using routine methods. Representative functional variants can include, e.g., one or more deletions, insertions, and/or substitutions in the HBV nucleic acids disclosed herein.

More specifically, embodiments of the oligonucleotides each include a nucleic acid with a sequence selected from SEQ ID NOs:1-392, a substantially identical variant thereof in which the variant has at least, e.g., 80%, 90%, or 95% sequence identity to one of SEQ ID NOs:1-392, or a complement SEQ ID NOs:1-192 and the variant. For instance, the number of Ts in the polyT stretch of the polyA binding primers can vary (8, 10, 12, 15, 17, 18 and so on), the presence and length of the HBV-binding or other anchor at the junction of the polyA tail can vary (being 5,7,8 bp long and so on), and the presence, type, number, and locations of modified bases in the primer can be varied.

In one embodiment, the above described sets of HBV primers, competitive blocking oligonucleotides, and probes are used in order to provide for detection of HBV RNA (in particular, HBV RNA transcribed from cccDNA, such as pgRNA) in a biological sample suspected of containing HBV (sequence listing, where N is meant to refer to any nucleotide). The sets of primers, competitive blocking oligonucleotides, and probes may comprise or consist of the primers, competitive blocking oligonucleotides, and probes specific for HBV nucleic acid sequences (e.g., HBV RNA, such as HBV RNA transcribed from cccDNA, such as pgRNA), comprising or consisting of the nucleic acid sequences of SEQ ID NOs:1-392. In another embodiment, the primers, competitive blocking oligonucleotides, and probes for the HBV target (including HBV RNA, such as HBV RNA transcribed from cccDNA (e.g., HBV pgRNA) comprise or consist of a functionally active variant of any of the primers, competitive blocking oligonucleotides, and probes of SEQ ID NOs: 1-392.

A functionally active variant of any of the primers (including RT primers), competitive blocking oligonucleotides, and/or probes of SEQ ID NOs: 1-392 may be identified by using the primers (including RT primers), competitive blocking oligonucleotides, and/or probes in the disclosed methods. A functionally active variant of a primer, competitive blocking oligonucleotide, and/or probe of any of the SEQ ID NOs: 1-392 pertains to a primer, competitive blocking oligonucleotide, and/or probe which provide a similar or higher specificity and sensitivity in the described method or kit as compared to the respective sequence of SEQ ID NOs: 1-392.

The variant may, e.g., vary from the sequence of SEQ ID NOs: 1-392 by one or more nucleotide additions, deletions or substitutions such as one or more nucleotide additions, deletions or substitutions at the 5' end and/or the 3' end of the respective sequence of SEQ ID NOs: 1-392. As detailed above, a primer (including RT primer), competitive blocking oligonucleotide, and/or probe may be chemically modified, i.e., a primer, competitive blocking oligonucleotide, and/or probe may comprise a modified nucleotide or a non-nucleotide compound. A primer, competitive blocking oligonucleotide, and/or probe is then a modified oligonucleotide. "Modified nucleotides" (or "nucleotide analogs"), as described previously, differ from a natural "nucleotide" by some modification but still consist of a base or base-like compound, a pentofuranosyl sugar or a pentofuranosyl sugar-like compound, a phosphate portion or phosphate-like portion, or combinations thereof. For example, a "label" may be attached to the base portion of a "nucleotide" whereby a "modified nucleotide" is obtained. A natural base in a "nucleotide" may also be replaced by, e.g., a 7-desazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

Oligonucleotides including modified oligonucleotides and oligonucleotide analogs that amplify a nucleic acid molecule encoding the HBV target, e.g., nucleic acids encoding alternative portions of HBV can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 8, 10, 12, 14, 16, 18, 20, 22, 24, 26, 28, 30, 32, 34, 36, 38, 40, 42, 44, 46, 48, or 50 nucleotides in length).

In the assay, a "competitive blocking oligonucleotide," "competitive blocking nucleotides," "competitive blocking nucleic acids," "blocking oligonucleotide," "blocking nucleotides", "blocker", and/or "blocking nucleic acids" are employed, and are terms that refer to a competitive blocking oligonucleotides bind to a region in the homologous genomic HBV DNA that is identical to the region targeted by the primer (e.g., RT primer), but that has higher affinity for the DNA than the RT primer does, for instance by not containing the polyA sequence in the RT primer but instead extending into the corresponding genomic sequence. That is, the competitive blocking oligonucleotide competes with the primer for binding to the target region, but the designs can be made in a way (such as differences in length, $T_m$, or position of sequences bound) to allow the RT primer to have greater affinity for the RNA while the competitive blocking oligonucleotide has greater affinity for the DNA. The binding of the competitive blocking oligonucleotide to the homologous genomic HBV DNA prevents binding of the primer (e.g., RT primer), and therefore reduces and/or prevents the unwanted amplification of the homologous genomic HBV DNA.

The set of forward primers for detection of the presence or absence of HBV nucleic acids, such as HBV RNA (such as HBV derived from cccDNA, such as pgRNA), include the sequences of SEQ ID NOs:20, 23, 24, 210, 213, 214, 387, and 389. The set of reverse transcription primers, which can function as reverse primers (e.g., RT/reverse primers) for detection of the presence or absence of HBV nucleic acids, such as HBV RNA (such as HBV derived from cccDNA, such as pgRNA), include the sequences of SEQ ID NOs:16, 18, 19, 25-30, 33-190, 206, 208, 209, 215-220, and 223-380. The set of competitive blocking oligonucleotides for increasing specificity of the detection of the presence or absence of HBV nucleic acids, such as HBV RNA (such as HBV derived from cccDNA, such as pgRNA), include the sequences of SEQ ID NOs:1-15, 21, 22, 191-205, 211, and 212. The set of probes for detection of the presence or absence of HBV nucleic acids, such as HBV RNA (such as HBV derived from cccDNA, such as pgRNA), include the sequences of SEQ ID NOs:17, 31, 32, 207, 221, 222, 381-386, 388, and 390-392.

In addition to a set of primers and competitive blocking oligonucleotides, the methods may use one or more probes in order to detect the presence or absence of HBV nucleic acid, such as HBV RNA (such as HBV derived from cccDNA, such as pgRNA). The term "probe" refers to synthetically or biologically produced nucleic acids (DNA or RNA), which by design or selection, contain specific nucleotide sequences that allow them to hybridize under defined predetermined stringencies specifically (i.e., preferentially) to "target nucleic acids", in the present case to HBV nucleic acids (including HBV RNA, such as HBV RNA transcribed from cccDNA, such as pgRNA) (target) nucleic acid. A "probe" can be referred to as a "detection probe" meaning that it detects the target nucleic acid.

In some embodiments, the described HBV nucleic acid probes (including probes for HBV RNA, such as HBV RNA transcribed from cccDNA, such as pgRNA) can be labeled with at least one fluorescent label. In one embodiment, the HBV nucleic acids probes (including probes for HBV RNA, such as HBV RNA transcribed from cccDNA, such as pgRNA) can be labeled with a donor fluorescent moiety, e.g., a fluorescent dye, and a corresponding acceptor moiety, e.g., a quencher. In one embodiment, the probe comprises or consists of a fluorescent moiety and the nucleic acid sequences comprise or consist of SEQ ID NOs:17, 31, 32, 207, 221, 222, 381-386, 388, and 390-392.

Designing oligonucleotides to be used as probes can be performed in a manner similar to the design of primers. Embodiments may use a single probe or a pair of probes for detection of the amplification product. Depending on the embodiment, the probe(s) used may comprise at least one label and/or at least one quencher moiety. As with the primers, the probes usually have melting temperatures appropriate for the thermal cycling parameters of the amplification method, and the length of each probe must be sufficient for sequence-specific hybridization to occur but not so long that fidelity is reduced during synthesis. Oligonucleotide probes are generally 15 to 40 (e.g., 16, 18, 20, 21, 22, 23, 24, or 25) nucleotides in length.

Constructs can include vectors each containing one or more of the sequences of the primers, competitive blocking oligonucleotides, and probes nucleic acid molecules for HBV (e.g., SEQ ID NOs:1-392). Constructs can be used, for example, as control template nucleic acid molecules. Vectors suitable for use are commercially available and/or produced by recombinant nucleic acid technology methods routine in the art. HBV nucleic acid molecules can be obtained, for example, by chemical synthesis, direct cloning from HBV, or by nucleic acid amplification.

Constructs suitable for use in the methods typically include, in addition to the HBV nucleic acids molecules (e.g., a nucleic acid molecule that contains one or more sequences of SEQ ID NOs:1-392), sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs containing HBV nucleic acids molecules can be propagated in a host cell. As used herein, the term host cell is meant to include prokaryotes and eukaryotes such as yeast, plant and animal cells. Prokaryotic hosts may include *E. coli, Salmonella typhimurium, Serratia marcescens*, and *Bacillus subtilis*. Eukaryotic hosts include yeasts such as *S. cerevisiae, S. pombe, Pichia pastoris*, mammalian cells such as COS cells or Chinese hamster ovary (CHO) cells, insect cells, and plant cells such as *Arabidopsis thaliana* and *Nicotiana tabacum*. A construct can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Constructs (plasmid vectors) can be used to generate RNA molecules, through an in-vitro transcription or other process, producing RNA templates which may also contain the binding sites of primers and probes. RNA template molecules can also be created by synthesis. A type of RNA template that can be created as a control material is an armored RNA (an RNA molecule that is enclosed within a protein coat), involving the production of RNA and a coat protein (such as a viral capsid protein) by a construct (for instance in a bacterial host) and assembly of the coat protein enclosing the RNA molecule. DNA molecules can also be enclosed in a protein coat for use as a control material.

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in some embodiments include oligonucleotides capable of acting as points of initiation of nucleic acid synthesis within the described HBV nucleic acid sequences (e.g., SEQ ID NOs:15, 18-20, 23-30, 33-190, 206, 208-210, 213-220, and 223-380). In some embodiments, the primers are reverse transcription (RT) primers (RT primers). A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 seconds to 4 minutes (e.g., 1 minute to 2 minutes 30 seconds, or 1.5 minutes).

If the double-stranded template nucleic acid is denatured by heat, the reaction mixture is allowed to cool to a temperature that promotes annealing of each primer to its target sequence. The temperature for annealing is usually from about 35° C. to about 65° C. (e.g., about 40° C. to about 60° C.; about 45° C. to about 50° C.). Annealing times can be from about 10 seconds to about 1 minute (e.g., about 20 seconds to about 50 seconds; about 30 seconds to about 40 seconds). If necessary, the reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 seconds to about 5 minutes (e.g., about 30 seconds to about 4 minutes; about 1 minute to about 3 minutes; about 1 minute 30 seconds to about 2 minutes).

The genome of a retrovirus or RNA virus is comprised of a ribonucleic acid, i.e., RNA. HBV is a pararetrovirus, which is a non-retrovirus that still uses reverse transcription in its replication process, requiring RNA made by host enzyme for viral replication. In such case, the template nucleic acid, RNA, must first be transcribed into complementary DNA (cDNA) via the action of the enzyme reverse transcriptase. Reverse transcriptases use an RNA template and a short primer complementary to the 3' end of the RNA to direct synthesis of the first strand cDNA, which can then be used directly as a template for polymerase chain reaction. For general preparation of RNA, primers can also be random, or assay/target-specific, depending on the method.

PCR assays can employ HBV nucleic acid such as RNA (such as HBV pgRNA) or DNA (cDNA). The template nucleic acid need not be purified; it may be a minor fraction of a complex mixture, such as HBV nucleic acid contained in human cells. HBV nucleic acid molecules may be extracted from a biological sample by routine techniques such as those described in *Diagnostic Molecular Microbiology: Principles and Applications* (Persing et al. (eds), 1993, American Society for Microbiology, Washington D.C.). Nucleic acids can be obtained from any number of sources, such as plasmids, or natural sources including bacteria, yeast, viruses, organelles, or higher organisms such as plants or animals.

The oligonucleotide primers (e.g., the forward primers comprising SEQ ID NOs: 20, 23, 24, 210, 213, 214, 387, and 389; and the RT/reverse primers comprising SEQ ID NOs: 16, 18, 19, 25-30, 33-190, 206, 208, 209, 215-220, and 223-380) are combined with PCR reagents under reaction conditions that induce primer extension. For example, chain extension reactions generally include 50 mM KCl, 10 mM Tris-HCl (pH 8.3), 15 mM $MgCl_2$, 0.001% (w/v) gelatin, 0.5-1.0 µg denatured template DNA, 50 pmoles of each oligonucleotide primer, 2.5 U of Taq polymerase, and 10% DMSO). The reactions usually contain 150 to 320 µM each of dATP, dCTP, dTTP, dGTP, or one or more analogs thereof.

The newly-synthesized strands form a double-stranded molecule that can be used in the succeeding steps of the reaction. The steps of strand separation, annealing, and elongation can be repeated as often as needed to produce the desired quantity of amplification products corresponding to the target HBV nucleic acid molecules (including HBV RNA, such as HBV pgRNA). The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. The donor typically transfers the energy to the acceptor when the donor is excited by light radiation with a suitable wavelength. The acceptor typically re-emits the transferred energy in the form of light radiation with a different wavelength. In certain systems, non-fluorescent energy can be transferred between donor and acceptor moieties, by way of biomolecules that include substantially non-fluorescent donor moieties (see, for example, U.S. Pat. No. 7,741,467).

In one example, an oligonucleotide probe can contain a donor fluorescent moiety (e.g., FAM) and a corresponding quencher (e.g., BlackHole Quenchers™ (BHQ) (such as BHQ2)), which may or not be fluorescent, and which dissipates the transferred energy in a form other than light. When the probe is intact, energy transfer typically occurs between the donor and acceptor moieties such that fluorescent emission from the donor fluorescent moiety is quenched the acceptor moiety. During an extension step of a polymerase chain reaction, a probe bound to an amplification product is cleaved by the 5' to 3' nuclease activity of, e.g., a Taq Polymerase such that the fluorescent emission of the donor fluorescent moiety is no longer quenched. Exemplary probes for this purpose are described in, e.g., U.S. Pat. Nos. 5,210,015, 5,994,056, and 6,171,785. Commonly used donor-acceptor pairs include the FAM-TAMRA pair. Commonly used quenchers are DABCYL and TAMRA. Commonly used dark quenchers include BlackHole Quenchers™ (BHQ) (such as BHQ2), (Biosearch Technologies, Inc., Novato, Cal.), Iowa Black™, (Integrated DNA Tech., Inc., Coralville, Iowa), BlackBerry™ Quencher 650 (BBQ-650), (Berry & Assoc., Dexter, Mich.).

In another example, two oligonucleotide probes, each containing a fluorescent moiety, can hybridize to an amplification product at particular positions determined by the complementarity of the oligonucleotide probes to the HBV RNA target nucleic acid sequence (including HBV RNA, such as HBV RNA transcribed from cccDNA, such as pgRNA). Upon hybridization of the oligonucleotide probes to the amplification product nucleic acid at the appropriate positions, a FRET signal is generated. Hybridization temperatures can range from about 35° C. to about 65° C. for about 10 seconds to about 1 minute.

Fluorescent analysis can be carried out using, for example, a photon counting epifluorescent microscope system (containing the appropriate dichroic mirror and filters for monitoring fluorescent emission at the particular range), a photon counting photomultiplier system, or a fluorimeter. Excitation to initiate energy transfer, or to allow direct detection of a fluorophore, can be carried out with an argon ion laser, a high intensity mercury (Hg) arc lamp, a xenon lamp, a fiber optic light source, or other high intensity light source appropriately filtered for excitation in the desired range.

As used herein with respect to donor and corresponding acceptor moieties "corresponding" refers to an acceptor fluorescent moiety or a dark quencher having an absorbance spectrum that overlaps the emission spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Foerster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, helium-cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC Red 640, LC Red 705, Cy5, Cy5.5, Lissamine rhodamine B sulfonyl chloride, tetramethyl rhodamine isothiocyanate, rhodaminexisothiocyanate, erythrosine isothiocyanate, fluorescein, diethylenetriamine pentaacetate, or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm can be the distance in Angstroms (Å) from the nucleotide base to the fluorescent moiety. In general, a linker arm is from about 10 Å to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety, such as an LC Red 640, can be combined with an oligonucleotide that contains an amino linker (e.g., C6-amino phosphoramidites available from ABI (Foster City, Calif.) or Glen Research (Sterling, Va.)) to produce, for example, LC Red 640-labeled oligonucleotide. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as CX-fluorescein-CPG from BioGenex (San Ramon, Calif.)), or 3'-amino-CPGs that require coupling of a fluorescein-NHS-ester after oligonucleotide synthesis.

Detection of Hepatitis B Virus (HBV) Amplified Product (Amplicon)

The present disclosure provides methods for detecting the presence or absence of HBV RNA (such as HBV RNA from transcribed cccDNA, such as HBV pgRNA) in a biological or non-biological sample. Methods provided avoid problems of sample contamination, false negatives, and false positives. The methods include performing at least one cycling step that includes amplifying a portion of HBV target nucleic acid molecules (such as HBV RNA transcribed from cccDNA, including HBV pgRNA) from a sample using one or more pairs of HBV primers, and a FRET detecting step. Multiple cycling steps are performed, preferably in a thermocycler. Methods can be performed using the HBV primers and probes to detect the presence of HBV target nucleic acid molecules (HBV RNA transcribed from cccDNA, including HBV pgRNA), and the detection of HBV target nucleic acid molecules (HBV RNA transcribed from cccDNA, including HBV pgRNA) indicates the presence of HBV target nucleic acid molecules (HBV RNA transcribed from cccDNA, including HBV pgRNA) in the sample.

As described herein, amplification products can be detected using labeled hybridization probes that take advantage of FRET technology. One FRET format utilizes TaqMan® technology to detect the presence or absence of an amplification product, and hence, the presence or absence of HBV virus (in particular, HBV nucleic acids, such as HBV RNA (e.g., HBV pgRNA)). TaqMan® technology utilizes one single-stranded hybridization probe labeled with, e.g., one fluorescent dye (e.g., HEX) and one quencher (e.g., BHQ), which may or may not be fluorescent. When a first fluorescent moiety is excited with light of a suitable wavelength, the absorbed energy is transferred to a second fluorescent moiety or a dark quencher according to the principles of FRET. The second moiety is generally a quencher molecule. During the annealing step of the PCR reaction, the labeled hybridization probe binds to the target DNA (i.e., the amplification product) and is degraded by the 5' to 3' nuclease activity of, e.g., the Taq Polymerase during the subsequent elongation phase. As a result, the fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems) uses TaqMan® technology, and is suitable for performing the methods described herein for detecting the presence or absence of HBV target nucleic acid molecules (HBV RNA RNA transcribed from cccDNA including HBV pgRNA) in the sample.

Molecular beacons in conjunction with FRET can also be used to detect the presence of an amplification product using the real-time PCR methods. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

Another common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LightCycler® Instrument. During FRET, the fluorescein transfers its energy to an acceptor fluorescent moiety such as LightCycler®-Red 640 (LC Red 640) or LightCycler®-Red 705 (LC Red 705). The acceptor fluorescent moiety then emits light of a longer wavelength, which is detected by the optical detection system of the LightCycler® instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target RNA or DNA molecules (e.g., the number of HBV nucleic acids (e.g., number of HBV RNA transcripts, such as HBV pgRNA). If amplification of HBV target nucleic acid (including HBV RNA, such as HBV pgRNA) occurs and an amplification product is produced, the step of hybridizing results in a detectable signal based upon FRET between the members of the pair of probes.

Generally, the presence of FRET indicates the presence of HBV RNA (such as HBV RNA molecules originating from cccDNA (HBV RNA transcribed from cccDNA, including HBV pgRNA) in the sample, and the absence of FRET indicates the absence of HBV RNA molecules (HBV RNA transcribed from cccDNA, including HBV pgRNA) in the sample. Inadequate specimen collection, transportation delays, inappropriate transportation conditions, or use of certain collection swabs (calcium alginate or aluminum shaft) are all conditions that can affect the success and/or accuracy of a test result, however.

Representative biological samples that can be used in practicing the methods include, but are not limited to respiratory specimens, urine, fecal specimens, blood specimens, plasma, serum, dermal swabs, nasal swabs, wound swabs, blood cultures, dried blood spots, skin, and soft tissue infections. Other biological samples may include cell culture and plasma separation cards or dried blood spots. Collection and storage methods of biological samples are known to those of skill in the art. Biological samples can be processed (e.g., by nucleic acid extraction methods and/or kits known in the art) to release HBV RNA (HBV RNA transcribed from cccDNA, including HBV pgRNA) or in some cases, the biological sample can be contacted directly with the PCR reaction components and the appropriate oligonucleotides.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the HBV probes from the HBV amplification products can confirm the presence or absence of HBV in the sample.

Within each thermocycler run, control samples can be cycled as well. Positive control samples can amplify target nucleic acid control template (other than described amplification products of target genes) using, for example, control primers and control probes. Positive control samples can also amplify, for example, a plasmid construct containing the target nucleic acid molecules. Such a plasmid control can be amplified internally (e.g., within the sample) or in a separate sample run side-by-side with the patients' samples using the same primers and probe as used for detection of the intended target. Such controls are indicators of the success or failure of the amplification, hybridization, and/or FRET reaction. Each thermocycler run can also include a negative control that, for example, lacks target template DNA. Negative control can measure contamination. This ensures that the system and reagents would not give rise to a false positive signal. Therefore, control reactions can readily determine, for example, the ability of primers to anneal with sequence-specificity and to initiate elongation, as well as the ability of probes to hybridize with sequence-specificity and for FRET to occur.

In an embodiment, the methods include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next.

Conventional PCR methods in conjunction with FRET technology can be used to practice the methods. In one embodiment, a LightCycler® instrument is used. The following patent applications describe real-time PCR as used in the LightCycler® technology: WO 97/46707, WO 97/46714, and WO 97/46712.

The LightCycler® can be operated using a PC workstation. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

The LightCycler® 480 II Real-Time PCR System can also be operated using a PC workstation. The instrument has a thermal block cycler and heating and cooling is achieved using Peltier elements. Fluorescent signals from the samples are obtained from the 96-well plate using a high-intensity Xenon lamp which emits light across a broad spectrum. Flexible combination of the built-in filters for specific excitation and emission allows the use of a variety of fluorescent dyes and detection formats. The software can display the fluorescence signals and calculate CT values, and the data generated can be stored for further analysis.

As an alternative to FRET, an amplification product can be detected using a double-stranded DNA binding dye such as a fluorescent DNA binding dye (e.g., SYBR® Green or SYBR® Gold (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

One of skill in the art would appreciate that other nucleic acid- or signal-amplification methods may also be employed. Examples of such methods include, without limitation, branched DNA signal amplification, loop-mediated isothermal amplification (LAMP), nucleic acid sequence-based amplification (NASBA), self-sustained sequence replication (3 SR), strand displacement amplification (SDA), or smart amplification process version 2 (SMAP 2).

It is understood that the embodiments of the present disclosure are not limited by the configuration of one or more commercially available instruments.

Articles of Manufacture/Kits

Embodiments of the present disclosure further provide for articles of manufacture or kits to detect HBV RNA (such as HBV RNA transcribed from cccDNA, such as HBV pgRNA). An article of manufacture can include primers and probes used to detect the HBV RNA (such as HBV RNA transcribed from cccDNA, such as HBV pgRNA) target, together with suitable packaging materials. Representative primers and probes for detection of HBV RNA, including HBV RNA transcribed from cccDNA, such as HBV pgRNA are capable of hybridizing to HBV target nucleic acid molecules (including HBV RNA transcribed from cccDNA, such as HBV pgRNA). In addition, the kits may also include suitably packaged reagents and materials needed for DNA immobilization, hybridization, and detection, such solid supports, buffers, enzymes, and DNA standards. Methods of designing primers and probes are disclosed herein, and representative examples of primers and probes that amplify and hybridize to HBV target nucleic acid molecules (HBV RNA, such as HBV RNA transcribed from cccDNA, such as HBV pgRNA) are provided.

Articles of manufacture can also include one or more fluorescent moieties for labeling the probes or, alternatively, the probes supplied with the kit can be labeled. For example, an article of manufacture may include a donor and/or an acceptor fluorescent moiety for labeling the HBV probes (which may include probes that target HBV RNA, such as HBV pgRNA). Examples of suitable FRET donor fluorescent moieties and corresponding acceptor fluorescent moieties are provided above.

Articles of manufacture can also contain a package insert or package label having instructions thereon for using the primers and probes to detect HBV (including HBV RNA, such as HBV pgRNA), in a sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

Embodiments of the present disclosure also provide for a set of primers and one or more detectable probes for the detection of HBV RNA, including HBV RNA transcribed from cccDNA, such as HBV pgRNA in a sample. Additional primers and probes can be provided for that target other polyA sites, such as the secondary or truncated polyA site for HBV transcripts that can originate from integrated HBV copies.

Embodiments of the present disclosure will be further described in the following examples, which do not limit the scope of the invention described in the claims.

EXAMPLES

The following examples and figures are provided to aid the understanding of the subject matter, the true scope of which is set forth in the appended claims. It is understood that modifications can be made in the procedures set forth without departing from the spirit of the invention.

The targeted region of the HBV includes HBV RNA, such as pgRNA. All nucleic acid sequences were aligned and all primers and probes were considered and scored for their predicted inclusivity for all known HBV isolates and other properties.

Example 1

HBV RNA poly-A Target Assay Design

An HBV RNA poly-A target assay was designed using an RT primer (used as a reverse primer) as shown in FIGS. 1 and 2. The target is an HBV RNA (such as HBV RNA originating from HBV cccDNA, which has the standard polyA tail, which includes HBV pgRNA), as shown in FIGS. 1 and 2. The assay can also detect splice variants and other RNAs, including mRNA, containing a poly-A tail. The RT primer, which can also act as a reverse primer, has a poly-T section to bind to the poly-A tail of the target mRNA (for example HBV pgRNA, as depicted in FIGS. 1 and 2). The HBV-specific sequence of the RT primer is designed to provide specificity for HBV and reduce RT/reverse primer binding to human and other poly-A-tailed RNA or stretches of homopolymer in the genome, however the longer the HBV-specific sequence is, the more likely it is to bind to HBV DNA. Indeed, even a short HBV-specific sequence has demonstrated ability to amplify off-target (i.e., unwanted) HBV DNA, when the DNA is at a high concentration. A tag sequence can optionally be added to the RT oligo, so that a different non-HBV sequence reverse primer design can be used for more efficient PCR amplification.

A competitive blocking oligonucleotide concept was incorporated to reduce the amplification of HBV DNA, by preferentially binding to the HBV DNA genome in place of the RT primer/reverse primer of the poly-A detection set (see, FIG. 2). This competitive blocking oligonucleotide is designed to be non-extensible, so it does not act as a primer. This may be accomplished, for example, by adding a C3 spacer on the 3'-end (a phosphate group or other attached group or modification may also be used for the same purpose). In this example, the competitive blocking oligonucleotide addition has been shown to increase the specificity of the assay for its intended target. This concept is applied, in this example, to a poly-A target for HBV RNA, but may be applicable to other poly-A designs for other targets; or other competitive template or interference situations, such as spliced RNA target with a short intron that would allow the DNA genome to also be amplified, situations with paralogous genes, or pseudogenes related to a target, or a sample with mixed genotypes or related organisms where one is targeted and not others.

In all of the examples of the present disclosure, the polymerase employed to detect and amplify HBV RNA was the modified *Thermus* Z05 polymerase known as Z05D. The Z05D modified polymerase has the sequence of wild type *Thermus* Z05 polymerase sequence, but with a D580G modification, as described in U.S. Pat. No. 8,962,293, which is incorporated herein by reference in its entirety. The Z05D polymerase is a nucleic acid polymerase has both reverse transcriptase (RT) and polymerase (DNA amplification) capabilities. The term "nucleic acid polymerase" refers to any polymerase enzyme that can polymerase nucleic acids, which includes DNA polymerases, RNA polymerase, reverse transcriptase (RT), DNA-dependent polymerase, RNA-dependent polymerases, and polymerases that exhibit reverse transcriptase (RT) and polymerase (DNA amplification) capabilities, such as the Z05D polymerase, employed in the examples of the present disclosure. Any polymerase that exhibits reverse transcriptase (RT) and polymerase (DNA amplification) capabilities can be used in the present disclosure to detect and amplify HBV RNA.

3' end construct including a polyA tail sequence. The template was added to negative human plasma at varying concentrations ($1 \times 10^0$ copies/mL, $1 \times 10^1$ copies/mL, $1 \times 10^2$ copies/mL, and so on up to $1 \times 10^9$ copies/mL) and extracted and eluted into the PCR reactions on the Cobas® 6800/8800. Reagents used include Cobas® 6800/8800 generic PCR Master Mix, with the profile and conditions for use with the Cobas® 6800/8800, and using TaqMan® amplification and detection technology.

The oligonucleotides specific for HBV pgRNA used for the real-time PCR assay were the RT/reverse primers HBV_PA-V_5LNA_25_351 (SEQ ID NO:152) and HBV_PA-V_5LNA_25_351_MIX (SEQ ID NO:151), along with a forward primer (SEQ ID NO:387) and probe (SEQ ID NO:388). Two reverse primers are used in this and some other experiments because a common substitution at the 3' end of the HBV RNA sequence may affect the performance of some primer designs. Paired primers with a base change to cover the variant reduce the potential effect of this substitution in samples. Thus, employing two reverse primers, instead of one reverse primer, allows for hybridization to variants with substitutions commonly observed at the 3' end of HBV RNA sequences. That is, employing more than one (i.e., two) reverse primers, instead of just one reverse primer, overcomes the complication of common substitutions at the 3' end of HBV RNA sequences. In general, it can be useful to employ multiple primers to cover multiple variations (including common or rare variations, substitutions, or other mutation types). A competitive blocking oligonucleotide "25-1" (SEQ ID NO:11) was included in the master mix, as were oligonucleotides for an internal control (not shown). These sequences are shown in Table 4, below.

TABLE 4

| Type | SEQ ID NO: | Sequence | Modifications |
|---|---|---|---|
| RT/R Primer | 152 | GATCAACGTGTCACCGCCTATTCTAT<D_LNA_T>TTT<D_LNA_T>TTT<D_LNA_T>TTT<D_LNA_T>TTT<D_LNA_T>T<D_LNA_T>TGAAGCTC | |
| RT/R Primer | 151 | GATCAACGTGTCACCGCCTATTCTAT<D_LNA_T>TTT<D_LNA_T>TTT<D_LNA_T>TTT<D_LNA_T>TTT<D_LNA_T>T<D_LNA_T>TGTAGCTC | |
| F. Primer | 387 | CATGCAACTTTTTCACCTCTGCCTF | Z = N6-benzyl-dA |
| Probe | 388 | ECCAAGCTGTGCCTTGGJGTGGFLLLGGGGFALGGP | E = HEX; J = BHQ-2; F = 5-Methyl dC; L = 5-Propynyl dU; P = P Phosphate |
| Blocking Oligo | 11 | GAGAG<pdU>AA<5_Me_dC><pdU><5_Me_dC><5_Me_dC>A<5_Me_dC>AGAAG<5_Me_dC>T<5_Me_dC>CAAA<pdU>TC<SpC_C3> | |

Example 2

Sensitivity and Linear Range of an HBV RNA poly-A Target Assay with a Competitive Blocking Oligonucleotide The HBV RNA poly-A target assay was designed using an RT primer (used as a reverse primer) as shown in FIGS. 1 and 2, with an HBV pgRNA 3' end poly-A target, in the presence of a competitive blocking oligonucleotide. The sensitivity and linear range of the assay was ascertained (FIG. 3).

Samples used for a real-time PCR assay were copies of an armored RNA containing the sequence for a HBV pgRNA The data show the performance of one example of the poly-A target PCR assay design on HBV pgRNA transcript containing the HBV poly-A site sequence with poly-A tail. The results, shown in FIG. 3, show greater amplicon production with greater amounts of starting HBV pgRNA transcript (in a dose-dependent fashion), reflecting the linear range as well as the sensitivity of the assay.

Figure 3:
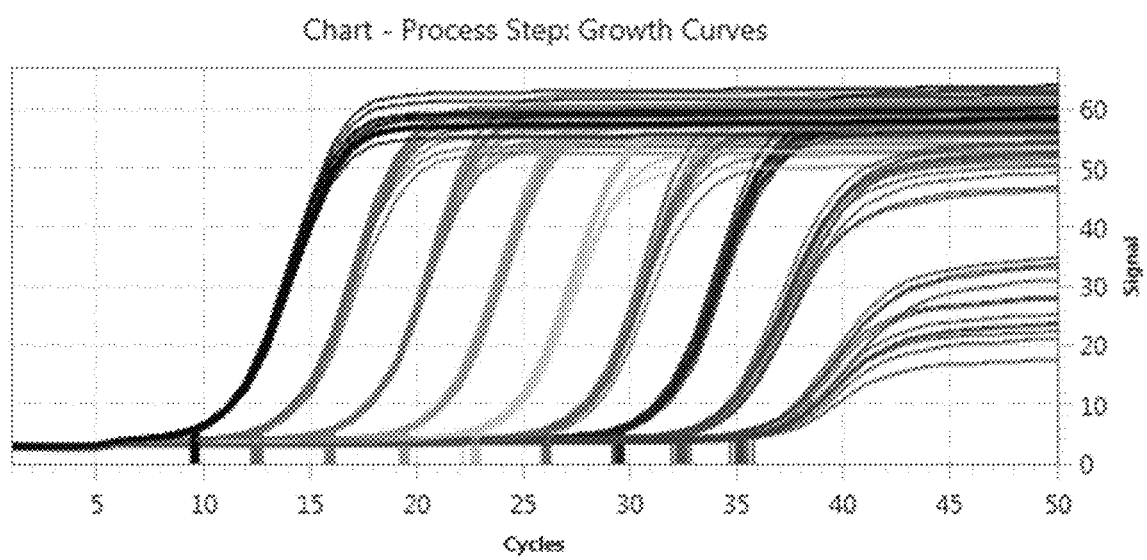
FIG. 3 shows real time PCR growth curves of an HBV RNA poly-A target assay, showing greater amplicon production with greater amount of starting copies of RNA template containing the HBV poly-A site sequence with poly-A tail, in the presence of an RT primer and a competitive blocking oligonucleotide.

Thus, these results, shown in FIG. 3, show real-time singleplex PCR growth curves, which demonstrate that the primers, competitive blocking oligonucleotides, and probes (SEQ ID NOs:11, 151, 152, 387, and 388) detect the presence of HBV pgRNA 3 in a real-time PCR assay.

Example 3

Specificity of HBV RNA Poly-A Target Assay with a Competitive Blocking Oligonucleotide The HBV RNA poly-A target assay was designed using an RT primer (used as a reverse primer) as shown in FIGS. 1 and 2, with an HBV pgRNA target. The specificity of the assay was ascertained, by way of PCR fluorescent signal on samples that were HBV DNA-only samples.

The reaction was run on HBV DNA template (armored DNA) at 250,000 IU/rxn, estimated equivalent to an input of 1 million IU/mL in a sample before extraction and processing steps. The oligonucleotides specific for HBV RNA used for the real-time PCR assay were the RT/reverse primer HBV_PA-Z 5LNA_25_351_MIX (SEQ ID NO:96), along with a HBV-specific forward primer (SEQ ID NO:387) and probe (SEQ ID NO:388). The same master mixes were run with and without the competitive blocking oligonucleotide "25-1" (SEQ ID NO:11). The oligonucleotide sequences are shown in Table 5, below.

samples that were mixed HBV RNA (target) and HBV DNA (non-target) templates, as reflected by CT values.

Figure 5:
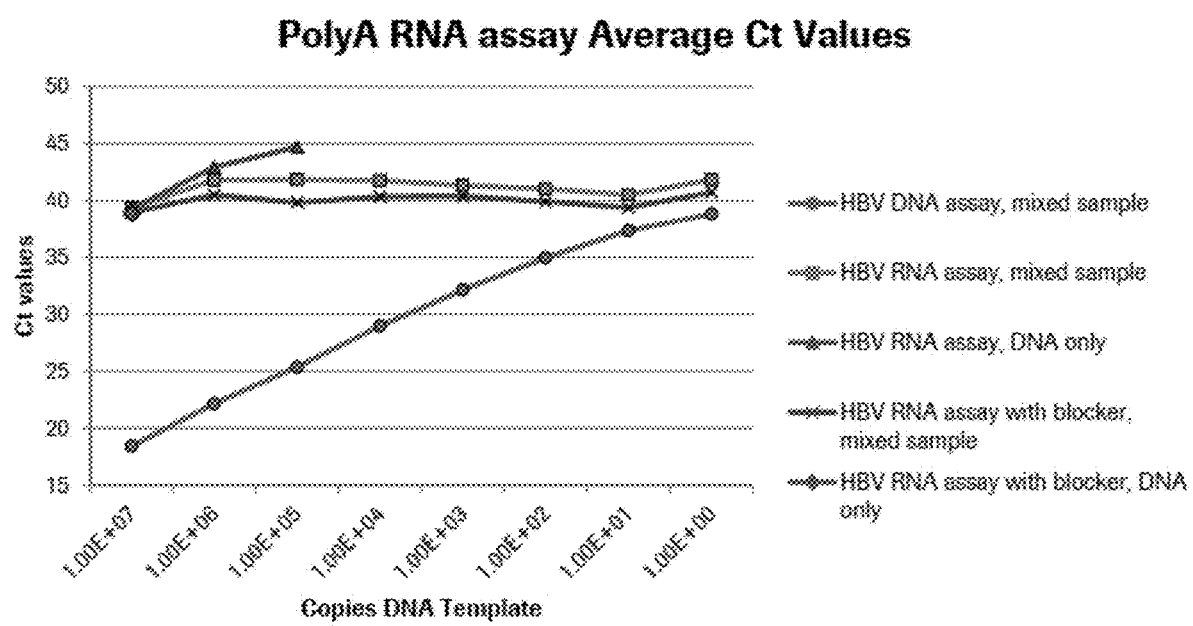
FIG. 5 shows CT values of an HBV RNA poly-A target assay, showing specificity against HBV DNA, under conditions of DNA only samples, mixed DNA+RNA samples, or mixed samples with competitive blocker.

Samples used for a singleplex real-time PCR assay were copies of HBV pgRNA transcript at $1\times10^3$ transcript/rxn and varying levels of HBV DNA construct (as shown on the x-axis of FIG. 5). The RNA assay was designed to detect the poly-A site on the transcript and be resistant to picking up the DNA, and a competitive blocking oligonucleotide is added to the assay in some conditions (where indicated in the legend of FIG. 5), in order to increase the specificity for RNA targets. The oligonucleotides specific for HBV RNA used for the real-time PCR assay were the RT/reverse primer HBV_PA-Z_25_351 (SEQ ID NO:43), along with a HBV-specific forward primer (SEQ ID NO:387) and probe (SEQ ID NO:388). The same master mixes were run with and without the competitive blocking oligonucleotide HBVpA_block2 (SEQ ID NO:2).

CT values for mixed samples and RNA assay (depicted as squares and X-markers, respectively, in FIG. 5) were consistent with RNA-only results, up to $1\times10^6$ copies of DNA (which indicates the signal up to that threshold is only from

TABLE 5

| Type | SEQ ID NO: | Sequence | Modifications |
|---|---|---|---|
| RT/R. Primer | 96 | GATCAACGTGTCACCGCCTATTCTAT\<LNA-T\>TTT\<LNA-T\>TTT\<LNA-T\>TTT\<LNA-T\>T\<LNA-T\>TGTAGC | |
| F. Primer | 387 | CATGCAACTTTTTCACCTCTGCCTF | Z = N6-benzyl-dA |
| Probe | 388 | ECCAAGCTGTGCCTTGGJGTGGFLLLGGGGFALGGP | E = HEX; J = BHQ-2; F = 5-Methyl dC; L = 5-Propynyl dU; P = P Phosphate |
| Blocking Oligo | 11 | GAGAG\<pdU\>AA\<5_Me_dC\>\<pdU\>\<5_Me_dC\>\<5_Me_dC\>A\<5_Me_dC\>AGAAG\<5_Me_dC\>T\<5_Me_dC\>CAAA\<pdU\>TC\<SpC_C3\> | |

The assay comparison was run on an LC480 PCR instrument. Reagents used include Cobas® 6800/8800 generic PCR Master Mix, with the profile and conditions for use with the Cobas® 6800/8800, and using TaqMan® amplification and detection technology. Final concentration of oligonucleotides in the master mix ranged from 150 nM to 300 nM. The results show amplicon production (off-target DNA amplification) in the presence of an RT primer without any blocker, and no amplicon production in the presence of an RT primer and a competitive blocking oligonucleotide.

Figure 4:
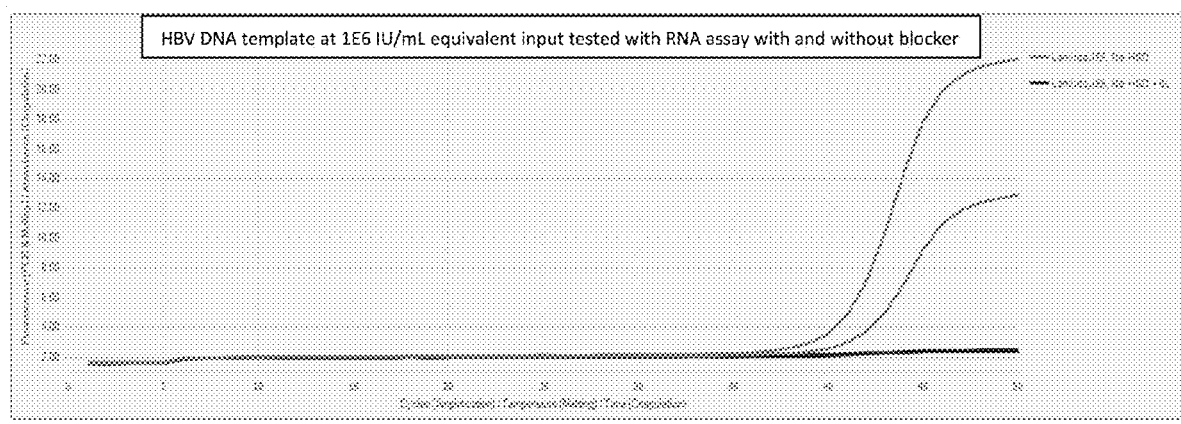
FIG. 4 shows real time PCR growth curves of an HBV RNA poly-A target assay with no RNA target but in the presence of 250,000 IU of HBV DNA (estimated equivalent to 1 million IU/mL in a sample before extraction and processing), showing amplicon production (off-target DNA amplification) in the presence of an RT primer without any blocker, and no amplicon production in the presence of an RT primer and a competitive blocking oligonucleotide.

These results, shown in FIG. 4, demonstrate the specificity against HBV DNA for the HBV RNA poly-A target assay, and the improvement possible including a competitive blocking oligonucleotide in the master mix. Thus, the HBV RNA poly-A target assay is specific for HBV RNA and specific against HBV DNA.

Example 4

Specificity and Mixed Template Results of HBV RNA poly-A Target Assay with a Competitive Blocking Oligonucleotide The HBV RNA poly-A target assay was designed using an RT primer (used as a reverse primer) as shown in FIGS. 1 and 2, with an HBV pgRNA target. The specificity of the assay was ascertained by way of PCR performance on RNA with insignificant contribution from DNA cross-reactivity despite increasing DNA input) (see, FIG. 5). The control used was a DNA assay (circles, in FIG. 5) on mixed samples, and shows earlier CTs with higher DNA input, as expected.

These results, shown in FIG. 5, demonstrate the specificity for HBV RNA (and against HBV DNA) for the HBV RNA poly-A target assay, and the improvement possible including a competitive blocking oligonucleotide in the master mix. Thus, the HBV RNA poly-A target assay is specific for HBV RNA and specific against HBV DNA (up to a certain titer of HBV DNA).

Example 5

Specificity and Mixed Template Fluorescence Results of HBV RNA poly-A Target Assay with a Competitive Blocking Oligonucleotide The HBV RNA poly-A target assay was designed using an RT primer (used as a reverse primer) as shown in FIGS. 1 and 2, with an HBV pgRNA target. The specificity of the assay was ascertained, by way of PCR fluorescent signal on samples that were mixed HBV RNA (target) and HBV DNA (non-target) templates, or HBV DNA-only samples.

Figure 6:
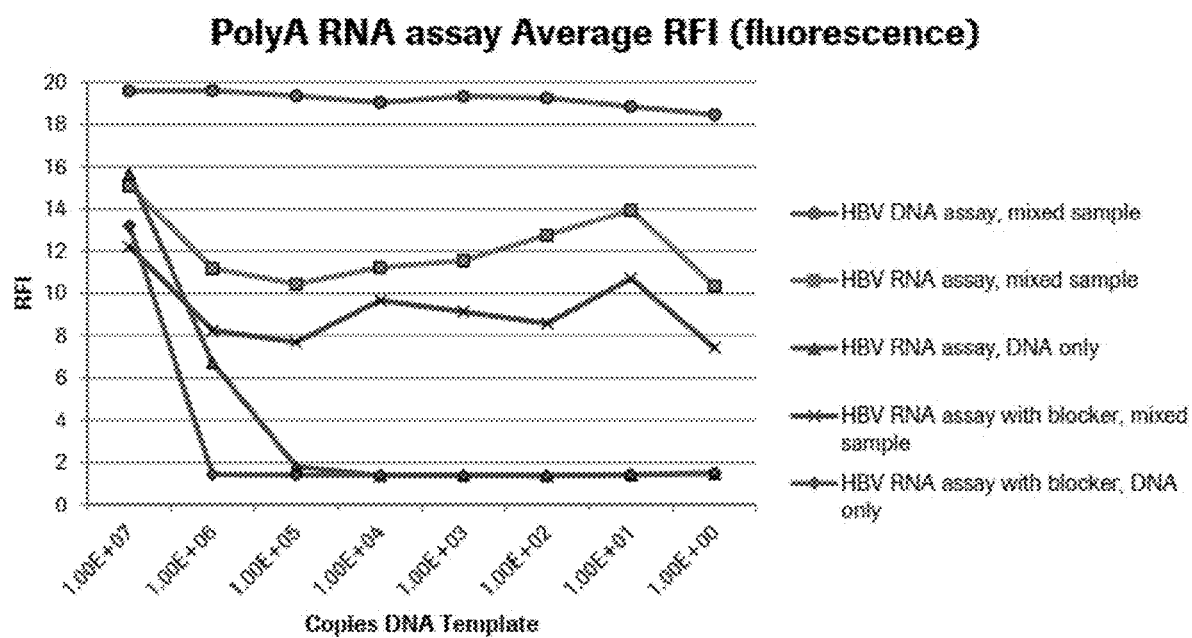
FIG. 6 shows a comparison of relative fluorescence intensity (RFI) of HBV RNA poly-A target assay, showing specificity against HBV DNA, under conditions of DNA only (with or without competitive blocker), and mixed DNA+RNA samples (with or without competitive blocker).

Samples used for a singleplex real-time PCR assay were copies of HBV pgRNA transcript at $1\times10^3$ transcript/rxn and varying levels of a HBV DNA construct (as shown on the x-axis of FIG. 6). The RNA assay was designed to detect the poly-A site on the transcript and be resistant to picking up the DNA, and a competitive blocking oligonucleotide is added in some conditions (where indicated in the legend of FIG. 6), in order to increase the specificity for RNA targets. The oligos used are the same as for Example 4. That is, the oligonucleotides specific for HBV RNA used for the real-time PCR assay were the RT/reverse primer HBV_PA-Z_25_351 (SEQ ID NO:43), along with a HBV-specific forward primer (SEQ ID NO:387) and probe (SEQ ID NO:388). The same master mixes were run with and without the competitive blocking oligonucleotide HBVpA_block2 (SEQ ID NO:2). Relative Fluorescence Intensity (RFI) values for mixed samples and the RNA assay (depicted as squares and X-markers, respectively, in FIG. 6) were consistent up to $1\times10^6$ copies of DNA (which indicates the signal up to that threshold is only from RNA or has insignificant contribution from DNA cross-reactivity) (see, FIG. 6). DNA-only samples (depicted by triangle marker) drop out below $1\times10^5$ copies/rxn DNA indicating that the RNA assay is not cross-reacting below that concentration of DNA (see, FIG. 6). DNA-only detection drops out at or below $1\times10^6$ copies/rxn, when using a competitive blocking oligonucleotide with the RNA assay (depicted by diamond marker, in FIG. 6), demonstrating the increased specificity with the competitive blocking oligonucleotide (see, FIG. 6). The control used was a DNA assay (depicted as circles, in FIG. 6), showing consistent fluorescence across DNA input levels (see, FIG. 6).

These results, shown in FIG. 6, demonstrate the specificity for HBV RNA (and against HBV DNA (up to a certain high titer input) for the HBV RNA poly-A target assay, and the improvement possible including a competitive blocking oligonucleotide in the master mix. Thus, the HBV RNA poly-A target assay is specific for HBV RNA and specific against HBV DNA.

Example 6

Specificity of HBV RNA poly-A Target Assay with a Competitive Blocking Oligonucleotide The HBV RNA poly-A target assay was designed using an RT primer (used as a reverse primer) as shown in FIGS. 1 and 2, with an HBV pgRNA target. The specificity of the assay was ascertained, by way of PCR fluorescent signal on samples that were HBV RNA-only samples and HBV DNA-only samples.

The multiplex (with an internal control (IC) reaction) real-time PCR assay was tested on HBV armored RNA at 100 copies/mL in human serum, extracted and eluted into the PCR reactions on the Cobas® 6800/8800. The assay was tested both without a competitive blocking oligonucleotide and including a competitive blocking oligonucleotide. The oligonucleotides specific for HBV RNA used for the real-time PCR assay were the RT/reverse primers HBV_PA-V_5LNA_25_351 (SEQ ID NO:152) and HBV_PA-V 5LNA_25_351 MIX (SEQ ID NO:151) along with a HBV-specific forward primer (SEQ ID NO:387) and probe (SEQ ID NO:388). A competitive blocking oligonucleotide "25-1" (SEQ ID NO:11) was included in the master mix, as were oligonucleotides for an internal control (not shown). Reagents used include Cobas® 6800/8800 generic PCR Master Mix, with the profile and conditions for use with the Cobas® 6800/8800, and using TaqMan® amplification and detection technology. Final concentration of oligonucleotides in the master mix ranged from 150 nM to 1 µM.

The presence or absence of the competitive blocking oligo did not affect the performance of the assay on the RNA target. Levels of concentration of the competitive blocking oligonucleotide can be adjusted to maximize the specificity against the unintended template or preserve the sensitivity of the assay on its intended target.

The same reaction mixes were run on HBV DNA (armored DNA) at 100,000 IU/mL in human serum, extracted and eluted into the PCR reactions on the Cobas® 6800/8800. This level of DNA had only a low level of fluorescent signal, however to demonstrate an alternative to increasing the Relative Fluorescence Intensity (RFI) cutoff to not call these off-target signals, the reaction was run including the competitive blocking oligo. The signals were eliminated in the presence of the blocker, therefore allowing greater sensitivity of the assay for RNA in the presence of up to 100,000 IU/mL DNA.

These results, shown in FIG. 7, demonstrate the specificity for HBV RNA (and against HBV DNA (up to a certain high titer input) for the HBV RNA poly-A target assay, and the improvement possible including a competitive blocking oligonucleotide in the master mix. Thus, the HBV RNA poly-A target assay is specific for HBV RNA and specific against HBV DNA.

Example 7

Effect of Modifications of Primers in HBV RNA poly-A Target Assay

The HBV RNA poly-A target assay was designed using an RT primer (used as a reverse primer) as shown in FIGS. 1 and 2, with an HBV pgRNA target. The performance of the assay when the RT/reverse primer design was varied was ascertained, by way of PCR fluorescent signal on samples that were HBV RNA samples.

The reaction was run on HBV RNA template (armored RNA) at 25 copies/rxn, estimated equivalent to an input of 100 copies/mL in a sample before extraction and processing steps, in a background of 125 ng/rxn human DNA. The oligonucleotides specific for HBV RNA used for the real-time PCR assay were the RT/reverse primers HBV_PA-W_8pdU_25_351_MIX (SEQ ID NO:117), HBV_PA-V_8pdU_25_351_MIX (SEQ ID NO:116), HBV_PA_8pdU_25_351s2_MIX (SEQ ID NO:112), and HBV_PA-Z_5LNA_25_351_MIX (SEQ ID NO:96), along with a HBV-specific forward primer (SEQ ID NO:387) and probe (SEQ ID NO:388). The oligonucleotide sequences are shown in Table 6, below.

TABLE 6

| Type | SEQ ID NO: | Sequence | Modifications |
|---|---|---|---|
| RT/R. Primer | 117 | GATCAACGTGTCACCGCCTATTCTAT<pdU>T<pdU>T<pdU>T<pdU><pdU><pdU>TTT<pdU>T<pdU>TGTAGCT | |

TABLE 6-continued

| Type | SEQ ID NO: | Sequence | Modifications |
|---|---|---|---|
| RT/R. Primer | 116 | GATCAACGTGTCACCGCCTATTCTA<pdU>T<pdU>T<pdU>T<pdU><pdU><pdU>TTT<pdU>T<pdU>TGTAGCTC | |
| RT/R. Primer | 112 | GATCAACGTGTCACCGCCTTT<pdU>T<pdU>T<pdU>T<pdU><pdU><pdU>TTT<pdU>T<pdU>TGTAGCTCC | |
| RT/R. Primer | 96 | GATCAACGTGTCACCGCCTATTCTAT<LNA-T>TTT<LNA-T>TTT<LNA-T>TTT<LNA-T>T<LNA-T>TGTAGC | |
| F. Primer | 387 | CATGCAACTTTTTCACCTCTGCCTF | F = 5-Methyl dC |
| Probe | 388 | ECCAAGCTGTGCCTTGGJGTGGFLLLGGGGFALGGP | E = HEX; J = BHQ-2; F = 5-Methyl dC; L = 5-Propynyl dU; P = P Phosphate |

The assay comparison (with an internal control (IC) reaction) was run on an LC480 PCR instrument. Reagents used include Cobas® 6800/8800 generic PCR Master Mix, with the profile and conditions for use with the Cobas® 6800/8800, and using TaqMan® amplification and detection technology. Final concentration of oligonucleotides in the master mix ranged from 150 nM to 300 nM. The results show amplicon production and fluorescent signal for all assays, but the assays with longer HBV-overlapping sequences at the polyA junction, with pdU modified bases in the polyT stretch of the primer, had greater signal. The assay with the LNA-T modified bases in the polyT stretch of the primer also had greater signal, even without a longer HBV-overlapping sequence at the polyA junction.

Figure 8:
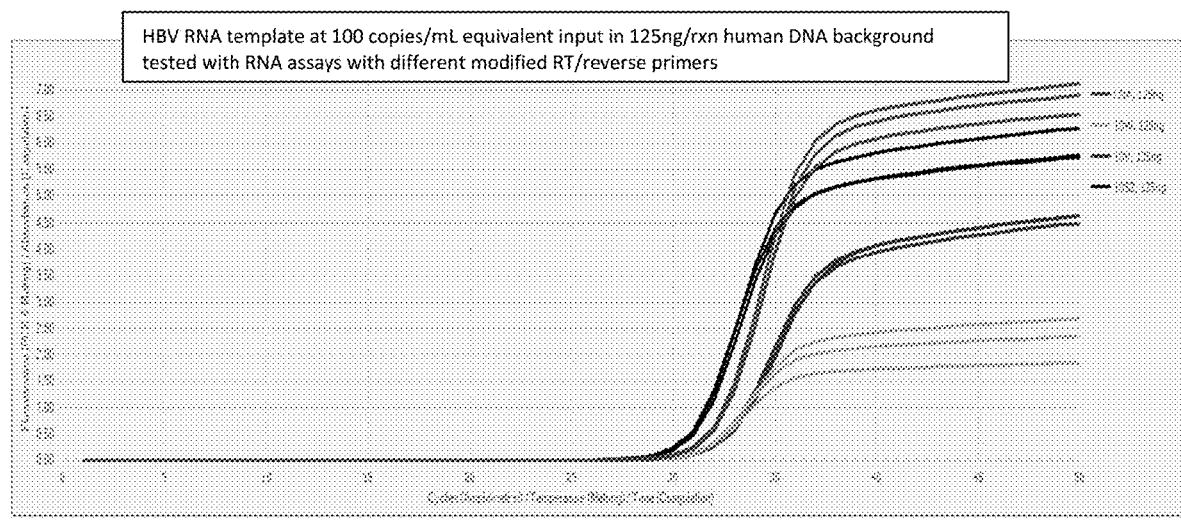
FIG. 8 shows real time PCR growth curves of an HBV RNA poly-A target assays with an RNA input level estimated to be equivalent of 100 copies/mL RNA template in a sample before extraction and processing, where the sample contains 125 ng/rxn human DNA background. Four different RT/reverse primers were tested, with different designs and modified bases, showing the performance improvements that can be seen with the adjustment of the oligo design and chemical modifications.

These results, shown in FIG. 8, demonstrate the performance effects of adjusting the design of the RT/reverse primer and the inclusion of different chemical modifications in the primer.

Example 8

Effect of HBV DNA on HBV RNA Quantitation with a Competitive Blocking Oligonucleotide The HBV RNA poly-A target assay was designed using an RT primer (used as a reverse primer) as shown in FIGS. 1 and 2, with an HBV pgRNA target. The performance of the assay was ascertained, by way of PCR fluorescent signal on samples that were HBV RNA samples.

The reaction was run on HBV RNA template (armored RNA) in a dilution series from $1\times10^9$ to 10 copies/mL HBV RNA in negative human plasma. The oligonucleotides specific for HBV RNA used for the real-time PCR assay were the RT/reverse primers HBV_PA-V_5LNA_25_351 (SEQ ID NO:152) and HBV_PA-V 5LNA_25_351 MIX (SEQ ID NO:151) along with a HBV-specific forward primer (SEQ ID NO:387) and probe (SEQ ID NO:388). A competitive blocking oligonucleotide "25-1" (SEQ ID NO:11) was included in the master mix, as were oligonucleotides for an internal control (not shown).

The multiplex (with an internal control (IC) reaction) real-time PCR assay was tested on HBV armored RNA in human plasma, extracted and eluted into the PCR reactions on the Cobas® 6800/8800. The assay was tested including a competitive blocking oligonucleotide. Ten replicates were tested per mixed concentration node. Reagents used include Cobas® 6800/8800 generic PCR Master Mix, with the profile and conditions for use with the Cobas® 6800/8800, and using TaqMan® amplification and detection technology. Final concentration of oligonucleotides in the master mix ranged from 333 nM to 1 µM.

The results, shown in FIG. 9, show tolerance of high HBV DNA input under conditions of mixed DNA+RNA samples. Without DNA added, the assay shows linearity from $1\times10^9$ to 10 copies/mL HBV RNA. With HBV DNA added at the high level of $1\times10^9$ IU/mL, the RNA assay is unaffected except at 100 and 10 copies/mL, where the DNA to RNA ratio is greater than 6.0 log (1 IU/mL HBV DNA is equivalent to >5 copies/mL of the DNA template).

In a parallel experiment $1\times10^7$ IU/mL of HBV DNA was shown to not affect accuracy of HBV RNA quantitation at 100 copies/mL and only a small effect at 10 copies/mL, confirming that the assay tolerates DNA input as long as the ratio between HBV DNA and HBV RNA is within 6 logs or less.

Thus, Example 8 demonstrates the high tolerance of the HBV RNA assay for DNA input. These data demonstrate that the HBV RNA assay, including the competitive blocking oligonucleotide, is very specific for HBV RNA, even in the presence of large amounts of potentially interfering/competing DNA.

Example 9

Effect of Reverse Primer Length and Modifications on Amplification of RNA and DNA The HBV RNA poly-A target assay was designed using an RT primer (used as a reverse primer) as shown in FIGS. 1 and 2, with an HBV pgRNA target. The performance of the assay when the RT/reverse primer design was varied was ascertained, by way of PCR fluorescent signal on samples that were HBV RNA samples. The RT/revers primers used were SEQ ID NOs:94, 96, 116, 117, 119, 121, 123, 124, 151, 153, 155, and 157; the forward primer used was SEQ ID NO:387; the probe used was SEQ ID NO:388; and the blocking oligonucleotide used was SEQ ID NO:11.

The reactions were run on HBV RNA template (armored RNA) at 25 copies/rxn, in a background of 12.5 ng/rxn human DNA. The reaction was also run on HBV DNA template at 250,000 IU/rxn. Assays were run including a competitive blocking oligonucleotide.

The assay comparisons were run on an LC480 PCR instrument. Reagents used include Cobas® 6800/8800 generic PCR Master Mix, with the profile and conditions for use with the Cobas® 6800/8800, and using TaqMan® amplification and detection technology. An internal control was also run. The results show amplicon production and fluorescent signal for all assays on RNA, but the assays with longer HBV-overlapping sequences at the polyA junction, with either pdU modified bases in the polyT stretch or LNA-T modified bases in the polyT stretch of the primer, tended to have slightly earlier Ct values on the RNA template but also relatively earlier Ct values on the DNA template.

These results, shown in the table below, demonstrate the performance effects of adjusting the design of the RT/reverse primer and the inclusion of different chemical modifications in the primer. In the table, the ranges of Ct values obtained for each primer design were as follows:

A is Ct of 25-30
B is Ct of 30-32
C is Ct of 32-35
D is Ct>35
E is no reaction

TABLE 7

| PRIMER | SEQUENCE | SEQ ID NO: | HBV RNA Ct at 25 copies/rxn (12.5ng hgDNA) | HBV DNA Ct at 250,000 IU/rxn with blocker |
|---|---|---|---|---|
| HBV_PA_Z_5LNA_25_351_MIX | GATCAACGTGTCACCGCCTATTCTAT<LNA_T>TTT<LNA_T>TTT<LNA_T>T<LNA_T>TGTAGC | 96 | C | E |
| HBV_PA_V_5LNA_25_351_MIX | GATCAACGTGTCACCGCCTATTCTCA<D_LNA_T>TTT<D_LNA_T>TTT<D_LNA_T>T<D_LNA_T>TGTAGCTC | 151 | B | D |
| HBV_PA_5LNA_25_351_MIX | GATCAACGTGTCACCGCCTATTCTA<D_LNA_T>TTT<D_LNA_T>TTT<D_LNA_T>T<D_LNA_T>TGTAGCTCC | 153 | B | C |
| HBV_PA9_5LNA_25_351_MIX | GATCAACGTGTCACCGCCTATTCTA<D_LNA_T>TT<D_LNA_T>TTT<D_LNA_T>TGTAGCTCCA | 155 | B | C |
| HBV_PA10_5LNA_25_351_MIX | GATCAACGTGTCACCGCCTATTCTA<D_LNA_T>TT<D_LNA_T>TTT<D_LNA_T>TGTAGCTCCAA | 157 | B | E |
| HBV_PA_z_8pdU_25_351_MIX | GATCAACGTGTCACCGCCTATTCTATT<pdU>T<pdU>T<pdU>T<pdU>TGTAGC | 94 | C | C |
| HBV_PA_W_8PDU_25_351_MIX | GATCAACGTGTCACCGCCTATTCTAT<pdU>T<pdU>T<pdU>T<pdU>TTT<pdU>TGTAGCT | 117 | C | C |
| HBV_PA_V_8PDU_25_351_MIX | GATCAACGTGTCACCGCCTATTCTA<pdU>T<pdU>T<pdU>T<pdU>TTT<pdU>T<pdU>TGTAGCTC | 116 | C | B |
| HBV_PA_8PDU_351S2_MIX | GATCAACGTGTCACCGCCTTT<pdU>T<pdU>T<pdU>T<pdU>TTT<pdU>TGTAGCTCC | 151 | B | B |
| HBV_PA9_8PDU_351S2_MIX | GATCAACGTGTCACCGCCTTT<pdU>T<pdU>T<pdU>T<pdU>TTT<pdU>TGTAGCTCCA | 119 | B | A |
| HBV_PA10_8PDU_351S2_MIX | GATCAACGTGTCACCGCCTTT<pdU>T<pdU>T<pdU>T<pdU>TTT<pdU>TGTAGCTCCAA | 121 | A | A |
| HBV_PA11_8PDU_351S2_MIX | GATCAACGTGTCACCGCCTTT<pdU>T<pdU>T<pdU>T<pdU>TTT<pdU>TGTAGCTCCAAA | 123 | C | B |
| HBV_PA14_8PDU_351S2_MIX | GATCAACGTGTCACCGCCTTT<pdU>T<pdU>T<pdU>T<pdU>TTT<pdU>TGTAGCTCCAAATTC | 124 | | |

Example 10

Effect of Reverse Primer Modifications n Amplification of RNA

The HBV RNA poly-A target assay was designed using an RT primer (used as a reverse primer) as shown in FIGS. 1 and 2, with an HBV pgRNA target. The performance of the assay when the RT/reverse primer design was varied was ascertained, by way of PCR fluorescent signal on samples that were HBV RNA samples. The RT/reverse primers employed were SEQ ID NOs: 142, 161, 162, 163, 164, 165, 166, 167, 168, 169, 171, 172, 173, 174, 175, 176, 177, 178, 179, 180, 181, 182, 183, 184, 185, 186, 187, 188, 189, and 190; the forward primer employed was SEQ ID NO:387; the probe employed was SEQ ID NO:388; and the blocking oligonucleotide employed was SEQ ID NO:11.

The reactions were run on HBV RNA template (armored RNA) at 25 copies/rxn, in a background of 12.5 ng/rxn human DNA. Assays were run including a competitive blocking oligonucleotide.

The assay comparisons were run on an LC480 PCR instrument. Reagents used include Cobas® 6800/8800 generic PCR Master Mix, with the profile and conditions for use with the Cobas® 6800/8800, and using TaqMan® amplification and detection technology. Internal controls were also included. The results show amplicon production and fluorescent signal for all assays on RNA. However, there can be modest variations in Ct values depending on the number and arrangement of chemically modified bases included in the oligos, with some arrangements appearing to be more efficient in amplification of the target than others.

These results, shown in the table below, demonstrate the performance effects of adjusting the design of the RT/reverse primer and the inclusion of different chemical modifications in the primer. In the table, the ranges of Ct values obtained for each primer design were as follows:

A is Ct of 25-30
B is Ct of 30-32
C is Ct of 32-35
D is Ct>35
E is no reaction

TABLE 8

| PRIMER | SEQUENCE | SEQ ID NO: | HBV RNA Ct at 25 copies/rxn (12.5 ng hgDNA) |
|---|---|---|---|
| HBV_PA_8LNA_25_351S2 | GATCAACGTGTCACCGCCTT<D_LNA_T><D_LNA_T>T<D_LNA_T>T<D_LNA_T>T<D_LNA_T>T<D_LNA_T>T<D_LNA_T>T<D_LNA_T>TGAAGCTCC | 177 | C |
| HBV_PA_8LNA_25_351S2_MIX | GATCAACGTGTCACCGCCTT<D_LNA_T>T<D_LNA_T>T<D_LNA_T>T<D_LNA_T>T<D_LNA_T>T<D_LNA_T>T<D_LNA_T>TGTAGCTCC | 176 | C |
| HBV_PA_8LNAEND_25_351 | GATCAACGTGTCACCGCCTATTCTATTTT<D_LNA_T><D_LNA_T><D_LNA_T><D_LNA_T><D_LNA_T><D_LNA_T><D_LNA_T><D_LNA_T>GAAGCTCC | 173 | C |
| HBV_PA_8LNAEND_25_351_MIX | GATCAACGTGTCACCGCCTATTCTATTTT<D_LNA_T><D_LNA_T><D_LNA_T><D_LNA_T><D_LNA_T><D_LNA_T><D_LNA_T><D_LNA_T>GTAGCTCC | 172 | B |
| HBV_PA_4LNAEND_25_351 | GATCAACGTGTCACCGCCTATTCTATTTTTTTTTTTT<D_LNA_T><D_LNA_T><D_LNA_T><D_LNA_T>GAAGCTCC | 169 | C |
| HBV_PA_4LNAEND_25_351_MIX | GATCAACGTGTCACCGCCTATTCTATTTTTTTTTTTT<D_LNA_T><D_LNA_T><D_LNA_T><D_LNA_T>GTAGCTCC | 168 | C |
| HBV_PA9_8LNA_25_351S2 | GATCAACGTGTCACCGCCTT<D_LNA_T>T<D_LNA_T>T<D_LNA_T>T<D_LNA_T>T<D_LNA_T>T<D_LNA_T>T<D_LNA_T>T<D_LNA_T>TGAAGCTCC | 179 | B |
| HBV_PA9_8LNA_25_351S2_MIX | GATCAACGTGTCACCGCCTT<D_LNA_T>T<D_LNA_T>T<D_LNA_T>T<D_LNA_T>T<D_LNA_T>T<D_LNA_T>T<D_LNA_T>T<D_LNA_T>TGTAGCTCCA | 178 | C |
| HBV_PA9_8LNAEND_25_351 | GATCAACGTGTCACCGCCTATTCTATTTT<D_LNA_T><D_LNA_T><D_LNA_T><D_LNA_T><D_LNA_T><D_LNA_T><D_LNA_T><D_LNA_T>GAAGCTCCA | 175 | B |
| HBV_PA9_8LNAEND_25_351_MIX | GATCAACGTGTCACCGCCTATTCTATTTT<D_LNA_T><D_LNA_T><D_LNA_T><D_LNA_T><D_LNA_T><D_LNA_T><D_LNA_T><D_LNA_T>GTAGCTCCA | 174 | C |
| HBV_PA9_4LNAEND_25_351 | GATCAACGTGTCACCGCCTATTCTATTTTTTTTTTTT<D_LNA_T><D_LNA_T><D_LNA_T><D_LNA_T>GAAGCTCCA | 171 | B |
| HBV_PA9_4LNAEND_25_351_MIX | GATCAACGTGTCACCGCCTATTCTATTTTTTTTTTTT<D_LNA_T><D_LNA_T><D_LNA_T><D_LNA_T>GTAGCTCCA | 170 | B |
| HBV_PA-V_12PDU_351S2_MIX | GATCAACGTGTCACCGCC<pdU><pdU><pdU><pdU><pdU><pdU><pdU><pdU><pdU><pdU><pdU><pdU>GTAGCTC | 186 | C |
| HBV_PA-V_12PDU_351S2 | GATCAACGTGTCACCGCC<pdU><pdU><pdU><pdU><pdU><pdU><pdU><pdU><pdU><pdU><pdU><pdU>GAAGCTC | 185 | C |
| HBV_PA_12PDU_351S2_MIX | GATCAACGTGTCACCGCC<pdU><pdU><pdU><pdU><pdU><pdU><pdU><pdU><pdU><pdU><pdU><pdU>GTAGCTCC | 142 | B |
| HBV_PA_12PDU_351 | GATCAACGTGTCACCGCC<pdU><pdU><pdU><pdU><pdU><pdU><pdU><pdU><pdU><pdU><pdU><pdU>GAAGCTCCA | 161 | B |

TABLE 8-continued

| PRIMER | SEQUENCE | SEQ ID NO: | HBV RNA Ct at 25 copies/rxn (12.5 ng hgDNA) |
|---|---|---|---|
| HBV_PA9_12PDU_351S2_MIX | GATCAACGTGTCACCGCC<pdU><pdU><pdU><pdU><pdU><pdU><pdU><pdU>GTAGCTCCA | 162 | B |
| HBV_PA9_8PDU_351S2_MIX_TBB | GATCAACGTGTCACCGCCTTT<pdU>T<pdU>T<pdU><pdU>T<pdU>TTT<pdU>T<pdU>TGTAGCTCC<t_BB_dA> | 165 | B |
| HBV_PA10_8PDU_351S2_MIX_TBB | GATCAACGTGTCACCGCCTTT<pdU>T<pdU>T<pdU>T<pdU><pdU>TTT<pdU>T<pdU>TGTAGCTCCA<t_BB_dA> | 166 | B |
| HBV_PA11_8PDU_351S2_MIX_TBB | GATCAACGTGTCACCGCCTTT<pdU>T<pdU>T<pdU>T<pdU><pdU>TTT<pdU>T<pdU>TGTAGCTCCAA<t_BB_dA> | 167 | B |
| HBV_PA10_12PDU_351S2_MIX | GATCAACGTGTCACCGCC<pdU><pdU><pdU><pdU><pdU><pdU><pdU><pdU>GAAGCTCCAA | 163 | A |
| HBV_PA10_12PDU_351S2 | GATCAACGTGTCACCGCC<pdU><pdU><pdU><pdU><pdU><pdU><pdU><pdU>GTAGCTCCAA | 164 | A |
| HBV_PA10_8LNAEND_25_351_MIX | GATCAACGTGTCACCGCCTATTCTATTTT<D_LNA_T><D_LNA_T><D_LNA_T><D_LNA_T><D_LNA_T><D_LNA_T><D_LNA_T><D_LNA_T>GTAGCTCCAA | 180 | B |
| HBV_PA10_8LNAEND_25_351 | GATCAACGTGTCACCGCCTATTCTATTTT<D_LNA_T><D_LNA_T><D_LNA_T><D_LNA_T><D_LNA_T><D_LNA_T><D_LNA_T><D_LNA_T>GAAGCTCCAA | 181 | B |
| HBV_PA10_8LNA_25_351S2_MIX | GATCAACGTGTCACCGCCTT<D_LNA_T>T<D_LNA_T>T<D_LNA_T>T<D_LNA_T>T<D_LNAT>T<D_LNA_T>T<D_LNA_T>T<D_LNA_T>TGTAGCTCCAA | 182 | C |
| HBV_PA10_8LNA_25_351S2 | GATCAACGTGTCACCGCCTT<D_LNA_T>T<D_LNA_T>T<D_LNA_T>T<D_LNA_T>T<D_LNA_T>T<D_LNA_T>T<D_LNA_T>T<D_LNA_T>TGAAGCTCCAA | 183 | C |
| HBV_PA10_8LNA_25_351_MIX | GATCAACGTGTCACCGCCTATTCTATTTTTT<D_LNA_T>TTT<D_LNA_T>T<D_LNA_T>T<D_LNA_T>T<D_LNA_T>TGTAGC | 184 | D |
| HBV_PA-Z_3LNA_25_351_MIX | GATCAACGTGTCACCGCCTATTCTATTCTATTTT<D_LNA_T><D_LNA_T><D_LNA_T>GTAGCTC | 187 | C |
| HBV_PA-V_8LNAEND_25_351_MIX | GATCAACGTGTCACCGCCTATTCTATTTT<D_LNA_T><D_LNA_T><D_LNA_T><D_LNA_T><D_LNA_T><D_LNA_T><D_LNA_T><D_LNA_T>GAAGCTC | 188 | D |
| HBV_PA-V_8LNA_25_351 | GATCAACGTGTCACCGCCTT<D_LNA_T>T<D_LNA_T>T<D_LNA_T>T<D_LNA_T>T<D_LNA_T>T<D_LNA_T>T<D_LNA_T>T<D_LNA_T>TGTAGCTC | 189 | C |
| HBV_PA-V_8LNA_25_351S2_MIX | GATCAACGTGTCACCGCCTT<D_LNA_T>T<D_LNA_T>T<D_LNA_T>T<D_LNA_T>T<D_LNA_T>T<D_LNA_T>T<D_LNA_T>T<D_LNA_T>TGTAGCTC | 190 | C |
| HBV_PA-V_8LNA_25_351S2 | GATCAACGTGTCACCGCCTT<D_LNA_T>T<D_LNA_T>T<D_LNA_T>T<D_LNA_T>T<D_LNA_T>T<D_LNA_T>T<D_LNA_T>T<D_LNA_T>TGAAGCTC | 190 | C |

Example 11

Effect of Reverse Primer Modifications on Amplification of RNA, on a Variant Template The HBV RNA poly-A target assay was designed using an RT primer (used as a reverse primer) as shown in FIGS. 1 and 2, with an HBV pgRNA target. The performance of the assay when the RT/reverse primer design was varied was ascertained, by way of PCR fluorescent signal on samples that were HBV RNA samples. The RT/Reverse Primer employed were SEQ ID NOs:141, 153, 157, 161, 163, 169, 171, 173, 175, 177, 179, 181, 183, 185, 188, and 190; the forward primer employed was SEQ ID NO:387; the probe employed was SEQ ID NO:388; and the blocking oligonucleotide employed was SEQ ID NO:11.

The reactions were run on HBV RNA template (armored RNA) at 25 copies/rxn, in a background of 12.5 ng/rxn human DNA. Assays were run including a competitive blocking oligonucleotide. In these experiments a variant HBV template was used which was different in sequence than in Example 10.

The assay comparisons were run on an LC480 PCR instrument. Reagents used include Cobas® 6800/8800 generic PCR Master Mix, with the profile and conditions for use with the Cobas® 6800/8800, and using TaqMan® amplification and detection technology. An internal control was also included. The results show amplicon production and fluorescent signal for all assays on RNA. However, there can be modest variations in Ct values depending on the number and arrangement of chemically modified bases included in the oligos, with some arrangements appearing to be more efficient in amplification of the target than others.

These results, shown in the table below, demonstrate the performance effects of adjusting the design of the RT/reverse primer and the inclusion of different chemical modifications in the primer. In the table, the ranges of Ct values obtained for each primer design were as follows:

A is Ct of 25-30
B is Ct of 30-32
C is Ct of 32-35
D is Ct>35
E is no reaction

TABLE 9

| PRIMER | SEQUENCE | SEQ ID NO: | HBV RNA Ct at 25 copies/nal (12.5 ng hgDNA) |
|---|---|---|---|
| HBV_PA-V_8LNA_25_351S2 | GATCAACGTGTCACCGCCCTT<D_LNA_T>T<D_LNA_T>T<D_LNA_T>T<D_LNA_T>T<D_LNA_T>T<D_LNA_T>T<D_LNA_T>T<D_LNA_T>TGAAGCTC | 190 | C |
| HBV_PA-V_8LNAEND_25_351 | GATCAACGTGTCACCGCCTATTCTATTTT<D_LNA_T><D_LNA_T><D_LNA_T><D_LNA_T><D_LNA_T><D_LNA_T><D_LNA_T>LNA_T>GAAGCTC | 188 | D |
| HBV_PA_8LNA_25_351S2 | GATCAACGTGTCACCGCCTT<D_LNA_T>T<D_LNA_T>T<D_LNA_T>T<D_LNA_T>T<D_LNA_T>T<D_LNA_T>T<D_LNA_T>T<D_LNA_T>TGAAGCTCC | 177 | C |
| HBV_PA_8LNAEND_25_351 | GATCAACGTGTCACCGCCTATTCTATTTT<D_LNA_T><D_LNA_T><D_LNA_T><D_LNA_T><D_LNA_T><D_LNA_T><D_LNA_T><D_LNA_T>GAAGCTCC | 173 | C |
| HBV_PA_4LNAEND_25_351 | GATCAACGTGTCACCGCCTATTCTATTTTTTTTTT<D_LNA_T><D_LNA_T><D_LNA_T><D_LNA_T>GAAGCTCC | 169 | C |
| HBV_PA9_8LNA_25_351S2 | GATCAACGTGTCACCGCCCTT<D_LNA_T>T<D_LNA_T>T<D_LNA_T>T<D_LNA_T>T<D_LNA_T>T<D_LNA_T>T<D_LNA_T>T<D_LNA_T>TGAAGCTCCA | 179 | C |
| HBV_PA9_8LNAEND_25_351 | GATCAACGTGTCACCGCCTATTCTATTTT<D_LNA_T><D_LNA_T><D_LNA_T><D_LNA_T><D_LNA_T><D_LNA_T><D_LNA_T><D_LNA_T>GAAGCTCCA | 175 | C |
| HBV_PA9_4LNAEND_25_351 | GATCAACGTGTCACCGCCTATTCTATTTTTTTTT<D_LNA_T><D_LNA_T><D_LNA_T><D_LNA_T>GAAGCTCCA | 171 | C |
| HBV_PA10_8LNA_25_351S2 | GATCAACGTGTCACCGCCCTT<D_LNA_T>T<D_LNA_T>T<D_LNA_T>T<D_LNA_T>T<D_LNA_T>T<D_LNA_T>T<D_LNA_T>T<D_LNA_T>TGAAGCTCCAA | 181 | C |
| HBV_PA10_8LNAEND_25_351 | GATCAACGTGTCACCGCCTATTCTATTTT<D_LNA_T><D_LNA_T><D_LNA_T><D_LNA_T><D_LNA_T><D_LNA_T><D_LNA_T>LNA_T>GAAGCTCCAA | 183 | C |
| HBV_PA10_4LNA_25_351S2 | GATCAACGTGTCACCGCC<pdU><pdU><pdU><pdU><pdU><pdU><pdU><pdU>GAAGCTC | 185 | C |
| HBV_PA-V_12PDU_351S2 | GATCAACGTGTCACCGCC<pdU><pdU><pdU><pdU><pdU><pdU><pdU><pdU><pdU><pdU><pdU><pdU>GAAGCTCC | 141 | C |
| HBV_PA9_12PDU_351S2 | GATCAACGTGTCACCGCC<pdU><pdU><pdU><pdU><pdU><pdU><pdU><pdU><pdU><pdU><pdU><pdU>GAAGCTCCA | 161 | B |
| HBV_PA10_12PDU_351S2 | GATCAACGTGTCACCGCC<pdU><pdU><pdU><pdU><pdU><pdU><pdU><pdU><pdU><pdU><pdU><pdU>GAAGCTCCAA | 163 | A |
| HBV_PA_5LNA_25_351_MIX | GATCAACGTGTCACCGCCTATTCTA<D_LNA_T>TTT<D_LNA_T>TTT<D_LNA_T>T<D_LNA_T>TGTAGCTCC | 153 | C |
| HBV_PA_5LNA_25_351 | GATCAACGTGTCACCGCCTATTCTA<D_LNA_T>TTT<D_LNA_T>TTT<D_LNA_T>T<D_LNA_T>TGAAGCTCC | 154 | C |

TABLE 9-continued

| PRIMER | SEQUENCE | SEQ ID NO: | HBV RNA Ct at 25 copies/nal (12.5 ng hgDNA) |
|---|---|---|---|

Example 12

Effect of Competitive Blocking Oligo Modifications on Amplification of DNA

The HBV RNA poly-A target assay was designed using an RT primer (used as a reverse primer) as shown in FIGS. 1 and 2, with an HBV pgRNA target. The assay utilizes a Competitive Blocking Oligonucleotide to improve the specificity of the assay against off-target amplification of HBV DNA. The performance of the assay when the blocker design primer design was varied was ascertained, by way of PCR fluorescent signal on samples that were HBV DNA samples.

The reaction was run on HBV DNA template at $1 \times 10^6$ copies/rxn. Assays were run including different competitive blocking oligonucleotides. In this experiment the RT/reverse primer used was HBV_PA_25_468 (SEQ ID NO:35), along with a forward primer (SEQ ID NO:387), and probe (SEQ ID NO:388). Here, the blocking oligonucleotides employed were SEQ ID NOs:1, 2, 3, 4, and 5.

The assay comparison was run on an LC480 PCR instrument. Reagents used include Cobas® 6800/8800 generic PCR Master Mix, with the profile and conditions for use with the Cobas® 6800/8800, and using TaqMan® amplification and detection technology. The results show amplicon production and fluorescent signal on high input levels of DNA, with delays in the Ct values from the inclusion of the blocking oligonucleotide. There are modest variations in Ct values depending on the number and arrangement of chemically modified bases included in the blocking oligos, with some arrangements appearing to be more efficient in competition (decreasing primer binding to the DNA target) than others.

These results, shown in the table below, demonstrate the performance effects of adjusting the design of the competitive blocking oligonucleotide and the inclusion of different chemical modifications in the blocking oligo. In the table, the ranges of Ct values obtained for each master mix were as follows:
A is Ct of 25-30
B is Ct of 30-32
C is Ct of 32-35
D is Ct>35
E is no reaction

Example 13

Effect of Competitive Blocking Oligo Modifications on Amplification of DNA

The HBV RNA poly-A target assay was designed using an RT primer (used as a reverse primer) as shown in FIGS. 1 and 2, with an HBV pgRNA target. The assay utilizes a Competitive Blocking Oligonucleotide to improve the specificity of the assay against off-target amplification of HBV DNA. The performance of the assay when the blocker design primer design was varied was ascertained, by way of PCR fluorescent signal on samples that were HBV DNA samples.

The reaction was run on HBV DNA template at $1 \times 10^7$ copies/rxn. Assays were run including different competitive blocking oligonucleotides. In this experiment the reverse primer used was different from that of Example 12. Here, the RT/reverse primer used was HBV_PA_25_351 (SEQ ID NO:34), along with a forward primer (SEQ ID NO:387), and probe (SEQ ID NO:388). Here, the blocking oligonucleotides employed were SEQ ID NO:2, 9, 10, 11, and 14.

The assay comparison was run on an LC480 PCR instrument. Reagents used include Cobas® 6800/8800 generic PCR Master Mix, with the profile and conditions for use with the Cobas® 6800/8800, and using TaqMan® amplification and detection technology. The results show amplicon production and fluorescent signal on high input levels of DNA, with delays in the Ct values from the inclusion of the blocking oligonucleotide. There are modest variations in Ct values depending on the number and arrangement of chemically modified bases included in the blocking oligos, with some arrangements (generally longer oligos and/or oligos with more modified bases) appearing to be more efficient in competition (decreasing primer binding to the DNA target) than others.

These results, shown in the table below, demonstrate the performance effects of adjusting the design of the competitive blocking oligonucleotide and the inclusion of different chemical modifications in the blocking oligo. In the table, the ranges of Ct values obtained for each master mix were as follows:
A is Ct of 25-30
B is Ct of 30-32
C is Ct of 32-35
D is Ct>35
E is no reaction

TABLE 10

| BLOCKER | SEQUENCE | SEQ ID NO: | HBV DNA at 1E6 copies/rxn |
|---|---|---|---|
| No blocker | N/A | | B |
| HBVPA_BLOCK1 | AACTCCACAGAAGCTCCAAATTC<Spc_C3> | 1 | C |
| HBVPA_BLOCK2 | AGAGTAACTCCACAGAAGCTCCAAATTC<Spc_C3> | 2 | E |
| HBVPA_BLOCK3 | GAGAGTAACTCCACAGAAGCTC<Spc_C3> | 3 | C |
| HBVPA_BLOCK5 | GAGAGTAACTCCACAGAAGC<Spc_C3> | 4 | D |
| HBVPA_BLOCK5L | G<LNA-A>GAGT<LNA-A>AC<LNA-T>CCACA<LNA-G>AA<LNA-G>C<Spc_C3> | 5 | C |

TABLE 11

| BLOCKER | SEQUENCE | SEQ ID NO: | HBV DNA at 1E7 copies/rxn |
|---|---|---|---|
| No blocker | | | A |
| HBVPA_BLOCK2 | AGAGTAACTCCACAGAAGCTCCAAATTC<Spc_C3> | 2 | B |
| HBVPA_BLOCK2-1 | AGAGTAAC<pdU>CCA<5_Me_dC>AGAAG<5_Me_dC>T<5_Me_dC>CAAA<pdU>TC<Spc_C3> | 9 | C |
| HBVPA_BLOCK2-2 | AGAG<pdU>AAC<pdU><5_Me_dC>CA<5_Me_dC>AGAAG<5_Me_dC><pdU><5_Me_dC><5_Me_dC>AAA<pdU>TC<Spc_C3> | 10 | C |
| HBVPA_BLOCK25-1 | GAGAG<pdU>AA<5_Me_dC><pdU><5_Me_dC><5_Me_dC>A<5_Me_dC>AGAAG<5_Me_dC>T<5_Me_dC>CAAA<pdU>TC<Spc_C3> | 11 | C |
| HBVPA_BLOCK7 | CAGAAGGCAAAAA<d_I>GAGAGTAACTCCACAGAAGCTCCAAATTCTTTATA<Spc_C3> | 14 | C |

Example 14

Effect of Competitive Blocking Oligo Modifications on Amplification of DNA

The HBV RNA poly-A target assay was designed using an RT primer (used as a reverse primer) as shown in FIGS. 1 and 2, with an HBV pgRNA target. The assay utilizes a Competitive Blocking Oligonucleotide to improve the specificity of the assay against off-target amplification of HBV DNA. The performance of the assay when the blocker design primer design was varied was ascertained, by way of PCR fluorescent signal on samples that were HBV DNA samples.

The reaction was run on HBV DNA template at $2 \times 10^6$ IU/rxn, in a background of 12.5 ng/rxn human DNA. Assays were run including different competitive blocking oligonucleotides. In this experiment the RT/reverse primer used was HBV_PA-V_5LNA_25_351 MIX (SEQ ID NO:151), along with a forward primer (SEQ ID NO:387) and probe (SEQ ID NO:388). Here, the blocking oligonucleotides were SEQ ID NOs:2, 10, 11, and 15.

The assay comparison was run on an LC480 PCR instrument. Reagents used include Cobas® 6800/8800 generic PCR Master Mix, with the profile and conditions for use with the Cobas® 6800/8800, and using TaqMan® amplification and detection technology. The results show amplicon production and fluorescent signal on high input levels of DNA, with delays in the Ct values from the inclusion of the blocking oligonucleotide. There are modest variations in Ct values depending on the number and arrangement of chemically modified bases included in the blocking oligos.

These results, shown in the table below, demonstrate several designs of the competitive blocking oligonucleotide differing in length and the inclusion of different chemical modifications. In the table, the ranges of Ct values obtained for each master mix were as follows:

A is Ct of 25-30
B is Ct of 30-32
C is Ct of 32-35
D is Ct>35
E is no reaction

TABLE 12

| BLOCKER | SEQUENCE | SEQ ID NO: | 2E8 IU/rxn HBV DNA in 12.5 ng hgDNA/rxn |
|---|---|---|---|
| HBVPA_BLOCK25-1 | GAGAG<pdU>AA<5_Me_dC><pdU><5_Me_dC><5_Me_dC>A<5_Me_dC>AGAAG<5_Me_dC>T<5_Me_dC>CAAA<pdU>TC<Spc_C3> | 11 | C |
| HBVPA_BLOCK2 | AGAGTAACTCCACAGAAGCTCCAAATTC<Spc_C3> | 2 | C |
| HBVPA_BLOCK2-2 | AGAG<pdU>AAC<pdU><5_Me_dC>CA<5_Me_dC>AGAAG<5_Me_dC><pdU><5_Me_dC><5_Me_dC>AAA<pdU>TC<Spc_C3> | 10 | C |
| HBVPA_BLOCK5L9 | G<LNA-A>G<LNA-A>G<LNA-T>A<LNA-A>C<LNA-T>C<LNA-C>A<LNA-C>A<LNA-G>AA<LNA-G>C<Spc_C3> | 15 | C |
| No blocker | N/A | | B |

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A method for detecting one or more target nucleic acids of Hepatitis B Virus (HBV) RNA in a sample, the method comprising:
   (a) providing a sample;
   (b) performing an amplification step comprising contacting the sample with one or more competitive blocking oligonucleotides and one or more set of primers, wherein the one or more set of primers comprises one or more forward primer and one or more reverse transcription (RT) primer that also functions as a reverse primer, to produce an amplification product, if the one or more target nucleic acids of HBV RNA is present in the sample, wherein the one or more competitive blocking oligonucleotides are characterized by being from 24 bases to 61 bases in length and/or by having modified stabilizing bases to increase melting temperature (Tm) and binding strength, and wherein the one or more RT primer contains HBV-specific sequence at its 3' end to reduce non-specific binding;
   (c) performing a hybridization step, comprising contacting the amplification product, if the one or more target nucleic acids of HBV RNA is present in the sample, with one or more probes; and
   (d) performing a detection step, comprising detecting the presence or absence of the amplification product, wherein the presence of the amplification product is indicative of the presence of the one or more target nucleic acids of HBV RNA in the sample, and wherein the absence of the amplification product is indicative of the absence of the one or more target nucleic acids of HBV RNA in the sample.

2. The method of claim 1, wherein the one or more competitive blocking oligonucleotides hybridizes to any homologous HBV DNA that may be present in the sample, thereby preventing the binding of the one or more set of primers to any homologous HBV DNA that may be present in the sample.

3. The method of claim 1, wherein the one or more target nucleic acids of HBV RNA is derived from covalently-closed circular double-stranded DNA (cccDNA).

4. The method of claim 3, wherein the cccDNA is HBV pre-genomic RNA (pgRNA).

5. The method of claim 1, wherein the one or more target nucleic acids of HBV RNA comprises a poly-A tail.

6. The method of claim 5, wherein the one or more reverse transcription (RT) primer that also functions as a reverse primer comprises a poly-T section to bind to the poly-A tail of the one or more target nucleic acids of HBV RNA.

7. The method of claim 1, wherein the sample is a biological sample.

8. The method of claim 7, wherein the biological sample is plasma.

9. The method of claim 7, wherein the biological sample is blood.

10. The method of any one of claims 1-9, wherein:
   (i) the one or more forward primer comprises a nucleic acid sequence of SEQ ID NO:387, or a complement thereof;
   (ii) the one or more reverse transcription (RT) primer that also functions as a reverse primer comprises one or more nucleic acid sequences of a group selected from SEQ ID NOs:34, 35, 43, 94, 96, 112, 116, 117, 119, 121, 123, 124, 141, 142, 151, 152, 153, 154, 155, 157, 161, 162, 163, 164, 165, 166, 167, 168, 169, 170, 171, 172, 173, 174, 175, 176, 177, 178, 179, 180, 181, 182, 183, 184, 185, 186, 187, 188, 189, and 190, or a complement thereof;
(iii) the one or more probes comprises a nucleic acid sequence of SEQ ID NO:388, or a complement thereof; and
(iv) the one or more competitive blocking oligonucleotides comprises a nucleic acid sequence of a group selected from SEQ ID NOs: 2, 5, 9, 10, 11, 14, and 15, or a complement thereof.

11. The method of claim 10, wherein
the one or more reverse transcription (RT) primer that also functions as a reverse comprises two nucleic sequences, wherein the two nucleic acid sequences comprise the nucleic acid sequences of SEQ ID NOs: 151 and 152, or complements thereof; and
the one or more competitive blocking oligonucleotides comprise one sequence comprising the nucleic acid sequence of SEQ ID NO:11, or a complement thereof.

12. The method of claim 10, wherein
the one or more reverse transcription (RT) primer that also functions as a reverse comprises the nucleic acid sequences of SEQ ID NO:96, or a complement thereof; and
the one or more competitive blocking oligonucleotides comprise one sequence comprising the nucleic acid sequence of SEQ ID NO:11, or a complement thereof.

13. The method of claim 10, wherein
the one or more reverse transcription (RT) primer that also functions as a reverse comprises the nucleic acid sequences of SEQ ID NO:43, or a complement thereof; and
the one or more competitive blocking oligonucleotides comprise one sequence comprising the nucleic acid sequence of SEQ ID NO:2, or a complement thereof.

14. The method of claim 10, wherein
the one or more reverse transcription (RT) primer that also functions as a reverse primer comprises one or more nucleic acid sequences of a group selected from SEQ ID NOs:96, 112, 116, and 117, or a complement thereof; and
the one or more competitive blocking oligonucleotides comprise one sequence comprising the nucleic acid sequence of SEQ ID NO:2, or a complement thereof.

15. The method of claim 10, wherein
the one or more reverse transcription (RT) primer that also functions as a reverse primer comprises one or more nucleic acid sequences of a group selected from SEQ ID NOs:94, 96, 116, 117, 119, 121, 123, 124, 151, 153, 155, and 157, or a complement thereof; and
the one or more competitive blocking oligonucleotides comprise one sequence comprising the nucleic acid sequence of SEQ ID NO:11, or a complement thereof.

16. The method of claim 10, wherein
the one or more reverse transcription (RT) primer that also functions as a reverse primer comprises one or more nucleic acid sequences of a group selected from SEQ ID NOs:142, 161, 162, 163, 164, 165, 166, 167, 168, 169, 171, 172, 173, 174, 175, 176, 177, 178, 179, 180, 181, 182, 183, 184, 185, 186, 187, 188, 189, and 190, or a complement thereof; and
the one or more competitive blocking oligonucleotides comprise one sequence comprising the nucleic acid sequence of SEQ ID NO:11, or a complement thereof.

17. The method of claim 10, wherein
the one or more reverse transcription (RT) primer that also functions as a reverse primer comprises one or more nucleic acid sequences of a group selected from SEQ ID NOs:141, 153, 157, 161, 163, 169, 171, 173, 175, 177, 179, 181, 183, 185, 188, and 190, or a complement thereof; and
the one or more competitive blocking oligonucleotides comprise one sequence comprising the nucleic acid sequence of SEQ ID NO:11, or a complement thereof.

18. The method of claim 10, wherein
the one or more reverse transcription (RT) primer that also functions as a reverse comprises the nucleic acid sequence of SEQ ID NO:35, or a complement thereof; and
the one or more competitive blocking oligonucleotides comprises one or more nucleic acid sequences of a group selected from SEQ ID NOs: 2, and 5, or a complement thereof.

19. The method of claim 10, wherein
the one or more reverse transcription (RT) primer that also functions as a reverse comprises the nucleic acid sequence of SEQ ID NO:34, or a complement thereof; and
the one or more competitive blocking oligonucleotides comprises one or more nucleic acid sequences of a group selected from SEQ ID NOs:2, 9, 10, 11, and 14, or a complement thereof.

20. The method of claim 10, wherein
the one or more reverse transcription (RT) primer that also functions as a reverse comprises the nucleic acid sequence of SEQ ID NO:151, or a complement thereof; and
the one or more competitive blocking oligonucleotides comprises one or more nucleic acid sequences of a group selected from SEQ ID NOs:2, 10, 11, and 15, or a complement thereof.

21. A method for detecting one or more target nucleic acids of Hepatitis B Virus (HBV) RNA in a sample, the method comprising:
(a) providing a sample;
(b) performing an amplification step comprising contacting the sample with one or more competitive blocking oligonucleotides and one or more set of primers, wherein the one or more set of primers comprises one or more forward primer and one or more one reverse transcription (RT) primer that also functions as a reverse primer, to produce an amplification product, if the one or more target nucleic acids of HBV RNA is present in the sample;
(c) performing a hybridization step, comprising contacting the amplification product, if the one or more target nucleic acids of HBV RNA is present in the sample, with one or more probes; and
(d) performing a detection step, comprising detecting the presence or absence of the amplification product, wherein the presence of the amplification product is indicative of the presence of the one or more target nucleic acids of HBV RNA in the sample, and wherein the absence of the amplification product is indicative of the absence of the one or more target nucleic acids of HBV RNA in the sample, and wherein:
the one or more set of primers comprises one or more one forward primer and one or more one reverse transcription (RT) primer that also functions as a reverse primer, and wherein:
(i) the one or more one forward primer comprises a nucleic acid sequence of SEQ ID NO:387, or a complement thereof;

(ii) the one or more one reverse transcription (RT) primer that also functions as a reverse primer comprises a poly-T section, and comprises one or more nucleic acid sequences of a group selected from SEQ ID NOs: 34, 35, 43, 94, 96, 112, 116, 117, 119, 121, 123, 124, 141, 142, 151, 152, 153, 154, 155, 157, 161, 162, 163, 164, 165, 166, 167, 168, 169, 170, 171, 172, 173, 174, 175, 176, 177, 178, 179, 180, 181, 182, 183, 184, 185, 186, 187, 188, 189, and 190, or a complement thereof;
(iii) the one or more probes comprises a nucleic acid sequence of SEQ ID NO:388, or a complement thereof; and
(iv) the one or more competitive blocking oligonucleotides comprises a nucleic acid of a group selected from SEQ ID NOs:2, 5, 9, 10, 11, 14, and 15, or a complement thereof.

22. The method of claim 21, wherein
the one or more reverse transcription (RT) primer that also functions as a reverse comprises two nucleic sequences, wherein the two nucleic acid sequences comprise the nucleic acid sequences of SEQ ID NOs: 151 and 152, or complements thereof; and
the one or more competitive blocking oligonucleotides comprise one sequence comprising the nucleic acid sequence of SEQ ID NO:11, or a complement thereof.

23. The method of claim 21, wherein
the one or more reverse transcription (RT) primer that also functions as a reverse comprises the nucleic acid sequences of SEQ ID NO:96, or a complement thereof; and
the one or more competitive blocking oligonucleotides comprise one sequence comprising the nucleic acid sequence of SEQ ID NO:11, or a complement thereof.

24. The method of claim 21, wherein
the one or more reverse transcription (RT) primer that also functions as a reverse comprises the nucleic acid sequences of SEQ ID NO:43, or a complement thereof; and
the one or more competitive blocking oligonucleotides comprise one sequence comprising the nucleic acid sequence of SEQ ID NO:2, or a complement thereof.

25. The method of claim 21, wherein
the one or more reverse transcription (RT) primer that also functions as a reverse primer comprises one or more nucleic acid sequences of a group selected from SEQ ID NOs:96, 112, 116, and 117, or a complement thereof; and
the one or more competitive blocking oligonucleotides comprise one sequence comprising the nucleic acid sequence of SEQ ID NO:2, or a complement thereof.

26. The method of claim 21, wherein
the one or more reverse transcription (RT) primer that also functions as a reverse primer comprises one or more nucleic acid sequences of a group selected from SEQ ID NOs:94, 96, 116, 117, 119, 121, 123, 124, 151, 153, 155, and 157, or a complement thereof; and
the one or more competitive blocking oligonucleotides comprise one sequence comprising the nucleic acid sequence of SEQ ID NO:11, or a complement thereof.

27. The method of claim 21, wherein
the one or more reverse transcription (RT) primer that also functions as a reverse primer comprises one or more nucleic acid sequences of a group selected from SEQ ID NOs:142, 161, 162, 163, 164, 165, 166, 167, 168, 169, 171, 172, 173, 174, 175, 176, 177, 178, 179, 180, 181, 182, 183, 184, 185, 186, 187, 188, 189, and 190, or a complement thereof; and
the one or more competitive blocking oligonucleotides comprise one sequence comprising the nucleic acid sequence of SEQ ID NO:11, or a complement thereof.

28. The method of claim 21, wherein
the one or more reverse transcription (RT) primer that also functions as a reverse primer comprises one or more nucleic acid sequences of a group selected from SEQ ID NOs:141, 153, 157, 161, 163, 169, 171, 173, 175, 177, 179, 181, 183, 185, 188, and 190, or a complement thereof; and
the one or more competitive blocking oligonucleotides comprise one sequence comprising the nucleic acid sequence of SEQ ID NO:11, or a complement thereof.

29. The method of claim 21, wherein
the one or more reverse transcription (RT) primer that also functions as a reverse comprises the nucleic acid sequence of SEQ ID NO:35, or a complement thereof; and
the one or more competitive blocking oligonucleotides comprises one or more nucleic acid sequences of a group selected from SEQ ID NOs: 2, and 5, or a complement thereof.

30. The method of claim 21, wherein
the one or more reverse transcription (RT) primer that also functions as a reverse comprises the nucleic acid sequence of SEQ ID NO:34, or a complement thereof; and
the one or more competitive blocking oligonucleotides comprises one or more nucleic acid sequences of a group selected from SEQ ID NOs:2, 9, 10, 11, and 14, or a complement thereof.

31. The method of claim 21, wherein
the one or more reverse transcription (RT) primer that also functions as a reverse comprises the nucleic acid sequence of SEQ ID NO:151, or a complement thereof; and
the one or more competitive blocking oligonucleotides comprises one or more nucleic acid sequences of a group selected from SEQ ID NOs:2, 10, 11, and 15, or a complement thereof.

32. The method of claim 21, wherein the one or more competitive blocking oligonucleotides hybridizes to any homologous HBV DNA that may be present in the sample, thereby preventing the binding of the one or more set of primers to any homologous HBV DNA that may be present in the sample.

33. The method of claim 21, wherein the one or more target nucleic acids of HBV RNA is derived from covalently-closed circular double-stranded DNA (cccDNA).

34. The method of claim 33, wherein the cccDNA is HBV pre-genomic RNA (pgRNA).

35. The method of claim 21, wherein the one or more target nucleic acids of HBV RNA comprises a poly-A tail.

36. The method of claim 35, wherein the one or more reverse transcription (RT) primer that also functions as a reverse primer comprises a poly-T section to bind to the poly-A tail of the one or more target nucleic acids of HBV RNA.

37. The method of claim 21, wherein the sample is a biological sample.

38. The method of claim 37, wherein the biological sample is plasma.

39. The method of claim 37, wherein the biological sample is blood.

40. A kit for detecting one or more target nucleic acids of Hepatitis B Virus (HBV) that may be present in a sample, the kit comprising amplification reagents comprising:

(a) a nucleic acid polymerase;
(b) nucleotide monomers;
(c) one or more set of primers, wherein the one or more set of primers comprises one or more forward primer and one or more reverse transcription (RT) primer that also functions as a reverse primer, wherein the one or more RT primer contains HBV-specific sequence at its 3' end to reduce non-specific binding; and
(d) one or more probes, and
(e) one or more competitive blocking oligonucleotides, characterized by being from 24 bases to 61 bases in length and/or by having modified stabilizing bases to increase melting temperature (Tm) and binding strength.

41. The kit of claim 40, wherein the one or more competitive blocking oligonucleotides hybridizes to any homologous HBV DNA that may be present in the sample, thereby preventing the binding of the one or more set of primers to any homologous HBV DNA that may be present in the sample.

42. The kit of claim 40, wherein the one or more target nucleic acids of HBV RNA is derived from covalently-closed circular double-stranded DNA (cccDNA).

43. The kit of claim 42, wherein the cccDNA is HBV pre-genomic RNA (pgRNA).

44. The kit of claim 40, wherein the one or more target nucleic acids of HBV RNA comprises a poly-A tail.

45. The kit of claim 44, wherein the one or more reverse transcription (RT) primer that also functions as a reverse primer comprises a poly-T section to bind to the poly-A tail of the one or more target nucleic acids of HBV RNA.

46. The kit of claim 40, wherein the sample is a biological sample.

47. The kit of claim 46, wherein the biological sample is plasma.

48. The kit of claim 46, wherein the biological sample is blood.

49. The kit of any one of claims 40-48, wherein:
(i) the one or more forward primer comprises a nucleic acid sequence of SEQ ID NO:387, or a complement thereof;
(ii) the one or more reverse transcription (RT) primer that also functions as a reverse primer comprises one or more nucleic acid sequences of a group selected from SEQ ID NOs: 34, 35, 43, 94, 96, 112, 116, 117, 119, 121, 123, 124, 141, 142, 151, 152, 153, 154, 155, 157, 161, 162, 163, 164, 165, 166, 167, 168, 169, 170, 171, 172, 173, 174, 175, 176, 177, 178, 179, 180, 181, 182, 183, 184, 185, 186, 187, 188, 189, and 190, or a complement thereof;
(iii) the one or more probes comprises a nucleic acid sequence of SEQ ID NO:388, or a complement thereof; and
(iv) the one or more competitive blocking oligonucleotides comprises a nucleic acid of a group selected from SEQ ID NOs: 2, 9, 10, 11, 14, and 15, or a complement thereof.

50. The kit of claim 49, wherein
the one or more reverse transcription (RT) primer that also functions as a reverse comprises two nucleic sequences, wherein the two nucleic acid sequences comprise the nucleic acid sequences of SEQ ID NOs: 151 and 152, or complements thereof; and
the one or more competitive blocking oligonucleotides comprise one sequence comprising the nucleic acid sequence of SEQ ID NO:11, or a complement thereof.

51. The kit of claim 49, wherein
the one or more reverse transcription (RT) primer that also functions as a reverse comprises the nucleic acid sequences of SEQ ID NO:96, or a complement thereof; and
the one or more competitive blocking oligonucleotides comprise one sequence comprising the nucleic acid sequence of SEQ ID NO:11, or a complement thereof.

52. The kit of claim 49, wherein
the one or more reverse transcription (RT) primer that also functions as a reverse comprises the nucleic acid sequences of SEQ ID NO:43, or a complement thereof; and
the one or more competitive blocking oligonucleotides comprise one sequence comprising the nucleic acid sequence of SEQ ID NO:2, or a complement thereof.

53. The kit of claim 49, wherein
the one or more reverse transcription (RT) primer that also functions as a reverse primer comprises one or more nucleic acid sequences of a group selected from SEQ ID NOs:96, 112, 116, and 117, or a complement thereof; and
the one or more competitive blocking oligonucleotides comprise one sequence comprising the nucleic acid sequence of SEQ ID NO:2, or a complement thereof.

54. The kit of claim 49, wherein
the one or more reverse transcription (RT) primer that also functions as a reverse primer comprises one or more nucleic acid sequences of a group selected from SEQ ID NOs:94, 96, 116, 117, 119, 121, 123, 124, 151, 153, 155, and 157, or a complement thereof; and
the one or more competitive blocking oligonucleotides comprise one sequence comprising the nucleic acid sequence of SEQ ID NO:11, or a complement thereof.

55. The kit of claim 49, wherein
the one or more reverse transcription (RT) primer that also functions as a reverse primer comprises one or more nucleic acid sequences of a group selected from SEQ ID NOs:142, 161, 162, 163, 164, 165, 166, 167, 168, 169, 171, 172, 173, 174, 175, 176, 177, 178, 179, 180, 181, 182, 183, 184, 185, 186, 187, 188, 189, and 190, or a complement thereof; and
the one or more competitive blocking oligonucleotides comprise one sequence comprising the nucleic acid sequence of SEQ ID NO:11, or a complement thereof.

56. The kit of claim 49, wherein
the one or more reverse transcription (RT) primer that also functions as a reverse primer comprises one or more nucleic acid sequences of a group selected from SEQ ID NOs:141, 153, 157, 161, 163, 169, 171, 173, 175, 177, 179, 181, 183, 185, 188, and 190, or a complement thereof; and
the one or more competitive blocking oligonucleotides comprise one sequence comprising the nucleic acid sequence of SEQ ID NO:11, or a complement thereof.

57. The kit of claim 49, wherein
the one or more reverse transcription (RT) primer that also functions as a reverse comprises the nucleic acid sequence of SEQ ID NO:35, or a complement thereof; and
the one or more competitive blocking oligonucleotides comprises one or more nucleic acid sequences of a group selected from SEQ ID NOs: 2, and 5, or a complement thereof.

58. The kit of claim 49, wherein
the one or more reverse transcription (RT) primer that also functions as a reverse comprises the nucleic acid sequence of SEQ ID NO:34, or a complement thereof; and
the one or more competitive blocking oligonucleotides comprises one or more nucleic acid sequences of a group selected from SEQ ID NOs:2, 9, 10, 11, and 14, or a complement thereof.

59. The kit of claim 49, wherein
the one or more reverse transcription (RT) primer that also functions as a reverse comprises the nucleic acid sequence of SEQ ID NO:151, or a complement thereof; and
the one or more competitive blocking oligonucleotides comprises one or more nucleic acid sequences of a group selected from SEQ ID NOs:2, 10, 11, and 15, or a complement thereof.

60. A kit for detecting Hepatitis B Virus (HBV) RNA in a sample, the method comprising:
(a) a nucleic acid polymerase;
(b) nucleotide monomers;
(c) one or more set of primers, wherein the one or more set of primers comprises one or more forward primer and one or more reverse transcription (RT) primer that also functions as a reverse primer;
(d) one or more probes; and
(e) one or more competitive blocking oligonucleotides; and
wherein:
(i) the one or more forward primer comprises a nucleic acid sequence of SEQ ID NO:387, or a complement thereof;
(ii) the one or more reverse transcription (RT) primer that also functions as a reverse primer comprises a poly-T section, and wherein the one or more reverse transcription primer that also functions as a reverse primer comprises one or more nucleic acid sequences of a group selected from SEQ ID NOs: 34, 35, 43, 94, 96, 112, 116, 117, 119, 121, 123, 124, 141, 142, 151, 152, 153, 154, 155, 157, 161, 162, 163, 164, 165, 166, 167, 168, 169, 170, 171, 172, 173, 174, 175, 176, 177, 178, 179, 180, 181, 182, 183, 184, 185, 186, 187, 188, 189, and 190, or a complement thereof;
(iii) the one or more probes comprises a nucleic acid sequence of SEQ ID NO:388, or a complement thereof; and
(iv) the one or more competitive blocking oligonucleotides comprises a nucleic acid of a group selected from SEQ ID NOs: 2, 5, 9, 10, 11, 14, and 15, or a complement thereof.

61. The kit of claim 60, wherein
the one or more reverse transcription (RT) primer that also functions as a reverse comprises two nucleic sequences, wherein the two nucleic acid sequences comprise the nucleic acid sequences of SEQ ID NOs: 151 and 152, or complements thereof; and
the one or more competitive blocking oligonucleotides comprise one sequence comprising the nucleic acid sequence of SEQ ID NO:11, or a complement thereof.

62. The kit of claim 60, wherein
the one or more reverse transcription (RT) primer that also functions as a reverse comprises the nucleic acid sequences of SEQ ID NO:96, or a complement thereof; and
the one or more competitive blocking oligonucleotides comprise one sequence comprising the nucleic acid sequence of SEQ ID NO:11, or a complement thereof.

63. The kit of claim 60, wherein
the one or more reverse transcription (RT) primer that also functions as a reverse comprises the nucleic acid sequences of SEQ ID NO:43, or a complement thereof; and
the one or more competitive blocking oligonucleotides comprise one sequence comprising the nucleic acid sequence of SEQ ID NO:2, or a complement thereof.

64. The kit of claim 60, wherein
the one or more reverse transcription (RT) primer that also functions as a reverse primer comprises one or more nucleic acid sequences of a group selected from of SEQ ID NOs:96, 112, 116, and 117, or a complement thereof; and
the one or more competitive blocking oligonucleotides comprise one sequence comprising the nucleic acid sequence of SEQ ID NO:2, or a complement thereof.

65. The kit of claim 60, wherein
the one or more reverse transcription (RT) primer that also functions as a reverse primer comprises one or more nucleic acid sequences of a group selected from SEQ ID NOs:94, 96, 116, 117, 119, 121, 123, 124, 151, 153, 155, and 157, or a complement thereof; and
the one or more competitive blocking oligonucleotides comprise one sequence comprising the nucleic acid sequence of SEQ ID NO:11, or a complement thereof.

66. The kit of claim 60, wherein
the one or more reverse transcription (RT) primer that also functions as a reverse primer comprises one or more nucleic acid sequences of a group selected from SEQ ID NOs:142, 161, 162, 163, 164, 165, 166, 167, 168, 169, 171, 172, 173, 174, 175, 176, 177, 178, 179, 180, 181, 182, 183, 184, 185, 186, 187, 188, 189, and 190, or a complement thereof; and
the one or more competitive blocking oligonucleotides comprise one sequence comprising the nucleic acid sequence of SEQ ID NO:11, or a complement thereof.

67. The kit of claim 60, wherein
the one or more reverse transcription (RT) primer that also functions as a reverse primer comprises one or more nucleic acid sequences of a group selected from SEQ ID NOs:141, 153, 157, 161, 163, 169, 171, 173, 175, 177, 179, 181, 183, 185, 188, and 190, or a complement thereof; and
the one or more competitive blocking oligonucleotides comprise one sequence comprising the nucleic acid sequence of SEQ ID NO:11, or a complement thereof.

68. The kit of claim 60, wherein
the one or more reverse transcription (RT) primer that also functions as a reverse comprises the nucleic acid sequence of SEQ ID NO:35, or a complement thereof; and
the one or more competitive blocking oligonucleotides comprises one or more nucleic acid sequences of a group selected from SEQ ID NOs: 2, and 5, or a complement thereof.

69. The kit of claim 60, wherein
the one or more reverse transcription (RT) primer that also functions as a reverse comprises the nucleic acid sequence of SEQ ID NO:34, or a complement thereof; and the one or more competitive blocking oligonucleotides comprises one or more nucleic acid sequences of a group selected from SEQ ID NOs:2, 9, 10, 11, and 14, or a complement thereof.

70. The kit of claim 60, wherein the one or more reverse transcription (RT) primer that also functions as a reverse comprises the nucleic acid sequence of SEQ ID NO:151, or a complement thereof; and the one or more competitive blocking oligonucleotides comprises one or more nucleic acid sequences of a group selected from SEQ ID NOs:2, 10, 11, and 15, or a complement thereof.

71. The kit of claim 60, wherein the one or more competitive blocking oligonucleotides hybridizes to any homologous HBV DNA that may be present in the sample, thereby preventing the binding of the one or more set of primers to any homologous HBV DNA that may be present in the sample.

72. The kit of claim 60, wherein the one or more target nucleic acids of HBV RNA is derived from covalently-closed circular double-stranded DNA (cccDNA).

73. The kit of claim 72, wherein the cccDNA is HBV pre-genomic RNA (pgRNA).

74. The kit of claim 60, wherein the one or more target nucleic acids of HBV RNA comprises a poly-A tail.

75. The kit of claim 74, wherein the one or more reverse transcription (RT) primer that also functions as a reverse primer comprises a poly-T section to bind to the poly-A tail of the one or more target nucleic acids of HBV RNA.

76. The kit of claim 60, wherein the sample is a biological sample.

77. The kit of claim 76, wherein the biological sample is plasma.

78. The kit of claim 76, wherein the biological sample is blood.

* * * * *